US008029775B2

(12) United States Patent
Bilsborough et al.

(10) Patent No.: US 8,029,775 B2
(45) Date of Patent: Oct. 4, 2011

(54) METHODS OF DETERMINING DOSE OF IL-31 AGONIST TO TREAT PULMONARY INFLAMMATION

(75) Inventors: Janine M. Bilsborough, Seattle, WA (US); Eric M. Chadwick, Bellevue, WA (US); Sherri L. Mudri, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 12/869,421

(22) Filed: Aug. 26, 2010

(65) Prior Publication Data

US 2011/0008820 A1    Jan. 13, 2011

Related U.S. Application Data

(62) Division of application No. 11/972,596, filed on Jan. 10, 2008, now Pat. No. 7,799,323.

(60) Provisional application No. 60/884,379, filed on Jan. 10, 2007.

(51) Int. Cl.
*A61K 38/20* (2006.01)
*A61K 38/16* (2006.01)
*C07K 14/00* (2006.01)
*C07K 14/54* (2006.01)

(52) U.S. Cl. ........ 424/85.2; 514/1.1; 514/1.7; 514/21.2; 530/350; 530/351

(58) Field of Classification Search ...................... None
See application file for complete search history.

(56) References Cited

U.S. PATENT DOCUMENTS

| | | | |
|---|---|---|---|
| 5,925,735 | A | 7/1999 | Baumgartner et al. |
| 7,064,186 | B2 | 6/2006 | Sprecher et al. |
| 7,425,325 | B2 | 9/2008 | Sprecher et al. |
| 7,459,293 | B2 | 12/2008 | Sprecher et al. |
| 7,494,804 | B2 | 2/2009 | Sprecher et al. |
| 7,507,795 | B2 | 3/2009 | Sprecher et al. |
| 7,514,077 | B2 | 4/2009 | Yao et al. |
| 7,531,636 | B2 | 5/2009 | Sprecher et al. |
| 7,531,637 | B2 | 5/2009 | Siadak et al. |
| 7,723,048 | B2 | 5/2010 | Bilsborough et al. |
| 7,740,834 | B2 | 6/2010 | Sprecher et al. |
| 2006/0182743 | A1 | 8/2006 | Bilsborough |
| 2006/0188499 | A1 | 8/2006 | Leung et al. |
| 2006/0188500 | A1 | 8/2006 | Leung et al. |
| 2006/0228329 | A1 | 10/2006 | Brady et al. |
| 2008/0260686 | A1 | 10/2008 | Bilsborough et al. |
| 2009/0149635 | A1 | 6/2009 | Sprecher et al. |
| 2009/0252732 | A1 | 10/2009 | Siadak et al. |

FOREIGN PATENT DOCUMENTS

| | | |
|---|---|---|
| WO | 03/060090 | 7/2003 |
| WO | 2004/003140 | 1/2004 |
| WO | 2006/081573 | 8/2006 |
| WO | 2006/122079 | 11/2006 |
| WO | 2008/028192 | 3/2008 |

OTHER PUBLICATIONS

Riken, 1999, (GenBank Acc. No. AV040649).
Riken, 1999, (GenBank Acc. No. AV044404).
Riken, 1999, (GenBank Acc. No. AV268991).
Riken, 1999, (GenBank Acc. No. AV280874).
National Cancer Institute, 1997, (GenBank Acc. No. BF152807).
Riken, 2001, (GenBank Acc. No. BB610257).
Riken, Accession No. AK005939, 1999.
Riken, Accession No. AK005939, Jul. 5, 2001.
National Institutes of Health, 1999, (GenBank Acc. No. CA464033).
Riken, 2002, (GenBank Acc. No. BY706076).
Washington University School of Medicine, 2002, (GenBank Acc. No. CF105870).
RZPD Deutsches Ressourcenzentrum fuer Genomforschung GmbH, 2003, (GenBank Acc. No. BX639332).
Whitehead Institute for Biomedical Research, Mouse Public Genomic Sequence TDB 3482986, Jan. 11, 2001.
Washington University Genome Sequencing Center, Mouse Public Genomic Sequence TDB 16727183, Feb. 24, 2001.
Whitehead Institute for Biomedical Research, Mouse Public Genomic Sequence TDB 10456006, Mar. 14, 2001.
Washington University Genome Sequencing Center, Mouse Public Genomic Sequence TDB 8480322, Jan. 13, 2001.
Whitehead Institute for Biomedical Research, Mouse Public Genomic Sequence TDB 49775248, Oct. 5, 2001.
Whitehead Institute for Biomedical Research, Mouse Public Genomic Sequence TDB 10005090, Mar. 10, 2001.
Whitehead Institute for Biomedical Research, Mouse Public Genomic Sequence TDB 20965871, Mar. 16, 2001.
Whitehead Institute for Biomedical Research, Mouse Public Genomic Sequence TDB 44835892, Sep. 20. 2001.
Washington University Genome Sequencing Center, Mouse Public Genomic Sequence TDB 50734527, Oct. 6, 2001.
Sanger Center, Mouse Public Genomic Sequence TDB 40505897, Aug. 31, 2001.
Sanger Center, Mouse Public Genomic Sequence TDB 1021719, Jan. 4, 2001.
Washington University Genome Sequencing Center, Mouse Public Genomic Sequence TDB 22973884, Apr. 16, 2001.
Abstract from the American Society of Human Genetics Meeting, Nov. 7, 2003 on Gene Structure and Function.
EMBL Accession No. AC048338, Apr. 2000. EMBL Accession No. AA381907, Apr. 1997.
Dillon et al., "Interleukin 31, a cytokine produced by activated T cells, induces dermatitis in mice," Nature Immunology 5(7):752-760, Jul. 2004.
Bilsborough et al., "IL-31 is associated with cutaneous lymphocyte antigen-positive skin homing T-cells in patients with atopic dermatitis", Journal of Allergy and Clinical Immunology, Mosby—Yearly Book, Inc., US 117(2): 418-425, Feb. 7, 2006.
Sonkoly et al., "IL-31: A new link between t-cells and pruritus in atopic skin inflammation", Journal of Allergy and Clinical Immunology, Mosby—Yearly Book, Inc., US 117(2): 411-417, Feb. 2006.

(Continued)

*Primary Examiner* — Christine J Saoud
*Assistant Examiner* — Jon M Lockard
(74) *Attorney, Agent, or Firm* — Brian J. Walsh; Robyn Adams

(57) ABSTRACT

Use of IL-31 agonists, including IL-31, are used to treat agonists are used to treat asthma, airway hyper-responsiveness or allergic rhinitis. The method comprise inhibiting, reducing, limiting or minimizing production of proinflammatory cytokines and include administration of the IL-31 agonist during sensitization or challenge resulting in the asthma, airway hyper-responsiveness or allergic rhinitis state.

12 Claims, 1 Drawing Sheet

OTHER PUBLICATIONS

Takaoka et al., "Involvement of IL-31 on scratching behavior in NC/Nga mice with atopic-like dermatitis", Experimental Dermatology, 15 (3): 161-167, Mar. 2006.

Takaoka et al., "Expression of IL-31 gene transcript in NC/Nga mice with atopic dermatitis", European Journal of Pharmacology, Amsterdam, NL, 516 (2): 180-181, May 31, 2005.

Goding, Journal of Immunological Methods vol. 39: 285-308, 1980.

Ständer et al., Hautarzt 54: 413-417, 2003.

Claudy, Pathologie et Biologie, L'Expansion Scientifique Francaise, Paris, FR 44(10): 888-894, 1996.

Leung et al., "New insights into atopic dermititis", Journal of Clinical Investigation 113(5): 651-657, Mar. 2004.

Boguniewics et al., "Atopic dermititis", J Allergy Clin Immunol, 117(2): S475-S480, Feb. 2006.

Castellani et al., "Interleukin-31: A new cytokine involved in inflammation of the skin", International Journal of Immunopathology and Pharmacology, 19(1): 1-4, Jan. 13, 2006.

"Monoclonal Anti-human IL-31 Antibody", R&D Systems, Inc., Apr. 18, 2006.

Presta et al., "Engineering of therapeutic antibodies to minimize immunogenicity and optimize function," Advanced Drug Delivery Reviews 58(5-6): 640-656, 2006.

Conti et al., "Modulation of autoimmunity by the latest interleukins (with special emphasis on IL-32)" Autoimmunity Reviews 6(3): 131-137, 2007.

EMBL Accession No. AK005939, Feb. 8, 2001.

Neis et al., "Enhanced expression levels of IL-31 correlate with IL-4 and IL-13 in atopic and allergic contact dermatitis," Journal of Allergy and Clinical Immunology, 118(4): 930-937, Oct. 1, 2006.

Wills-Karp, M., "The gene encoding inerleukin-13: a susceptibility locus for asthma and related traits," Respiratory Research, 1(1): 19-23, Jul. 17, 2000.

Dillon et al., "Transgenic mice overexpressing a novel cytokine (IL-31) develop a severe pruritic skin phenotype resembling atopic dermatitis," European Cytokine Network 14(3): 81, 2003.

Perrigoue et al., "IL-31-IL-31R interactions negatively regulate type 2 inflammation in the lung," Journal of Experimental Medicine 204(3): 481-487, Mar. 19, 2007.

Jawa et al., "Expression, regulation and signaling by interleukin 31 receptor alpha (IL-31RA) in bronchnopulmonary epithelial cells and pulmonary macrophages," Assocation for Academic Surgery and Society of University Surgeons, abstract, (2007).

Brusasco and Pellegrino, "Airway Hyperresponsiveness: From Molecules to Bedside," J. Appl. Physiol. 95: 1305-1313, 2003.

SEQUENCE LISTING

```
<160> NUMBER OF SEQ ID NOS: 16

<210> SEQ ID NO 1
<211> LENGTH: 904
<212> TYPE: DNA
<213> ORGANISM: Homo sapiens
<220> FEATURE:
<221> NAME/KEY: CDS
<222> LOCATION: (28)...(522)

<400> SEQUENCE: 1
ctgaagctgg ccttgctctc tctcgcc atg gcc tct cac tca ggc ccc tcg acg        54
                               Met Ala Ser His Ser Gly Pro Ser Thr
                                 1               5 tct gtg ctc ttt ctg ttc tgc tgc ctg gga ggc tgg ctg gcc tcc cac         102
Ser Val Leu Phe Leu Phe Cys Cys Leu Gly Gly Trp Leu Ala Ser His
 10              15                  20                  25 acg ttg ccc gtc cgt tta cta cga cca agt gat gat gta cag aaa ata         150
Thr Leu Pro Val Arg Leu Leu Arg Pro Ser Asp Asp Val Gln Lys Ile
                 30                  35                  40 gtc gag gaa tta cag tcc ctc tcg aag atg ctt ttg aaa gat gtg gag         198
Val Glu Glu Leu Gln Ser Leu Ser Lys Met Leu Leu Lys Asp Val Glu
             45                  50                  55 gaa gag aag ggc gtg ctc gtg tcc cag aat tac acg ctg ccg tgt ctc         246
Glu Glu Lys Gly Val Leu Val Ser Gln Asn Tyr Thr Leu Pro Cys Leu
         60                  65                  70 agc cct gac gcc cag ccg cca aac aac atc cac agc cca gcc atc cgg         294
Ser Pro Asp Ala Gln Pro Pro Asn Asn Ile His Ser Pro Ala Ile Arg
     75                  80                  85 gca tat ctc aag aca atc aga cag cta gac aac aaa tct gtt att gat         342
Ala Tyr Leu Lys Thr Ile Arg Gln Leu Asp Asn Lys Ser Val Ile Asp
 90                  95                 100
```

```
                   90                  95                 100                 105
gag atc ata gag cac ctc gac aaa ctc ata ttt caa gat gca cca gaa       390
Glu Ile Ile Glu His Leu Asp Lys Leu Ile Phe Gln Asp Ala Pro Glu
                    110                 115                 120 aca aac att tct gtg cca aca gac acc cat gaa tgt aaa cgc ttc atc       438
Thr Asn Ile Ser Val Pro Thr Asp Thr His Glu Cys Lys Arg Phe Ile
                    125                 130                 135 ctg act att tct caa cag ttt tca gag tgc atg gac ctc gca cta aaa       486
Leu Thr Ile Ser Gln Gln Phe Ser Glu Cys Met Asp Leu Ala Leu Lys
                    140                 145                 150 tca ttg acc tct gga gcc caa cag gcc acc act taa ggccatctct            532
Ser Leu Thr Ser Gly Ala Gln Gln Ala Thr Thr  *
                    155                 160 tcctttcgga ttggcaggaa cttaaggagc cttaaaaaga tgaccgacag ctaagtgtgg     592
gaactctgcc gtgattcctt aagtacattt ttccaatgaa taatctcagg gaccoctcat    652 atgggctagt cccgggaggg ctgagatgtg aatttgtgaa ttaccttgaa aaacattagg    712
ttattgttat tagtcttggt atttatggaa tgcttttctt ctgcaggctt aagtcttact    772
tattataccc tcgtgagggt gggaggtggc agctatgtta aatttattgat atttattgta    832 ctaagagttg tcaatgctcc ctgggggagc cctcggaatc tatttaataa attatattga    892 attttttctca ta                                                      904

<210> SEQ ID NO 2
<211> LENGTH: 164
<212> TYPE: PRT
<213> ORGANISM: Homo sapiens

<400> SEQUENCE: 2

Met Ala Ser His Ser Gly Pro Ser Thr Ser Val Leu Phe Leu Phe Cys
 1               5                  10                  15

Cys Leu Gly Gly Trp Leu Ala Ser His Thr Leu Pro Val Arg Leu Leu
                20                  25                  30

Arg Pro Ser Asp Asp Val Gln Lys Ile Val Glu Glu Leu Gln Ser Leu
            35                  40                  45

Ser Lys Met Leu Leu Lys Asp Val Glu Glu Glu Lys Gly Val Leu Val
        50                  55                  60

Ser Gln Asn Tyr Thr Leu Pro Cys Leu Ser Pro Asp Ala Gln Pro Pro
65                  70                  75                  80

Asn Asn Ile His Ser Pro Ala Ile Arg Ala Tyr Leu Lys Thr Ile Arg
                85                  90                  95

Gln Leu Asp Asn Lys Ser Val Ile Asp Glu Ile Ile Glu His Leu Asp
            100                 105                 110

Lys Leu Ile Phe Gln Asp Ala Pro Glu Thr Asn Ile Ser Val Pro Thr
        115                 120                 125

Asp Thr His Glu Cys Lys Arg Phe Ile Leu Thr Ile Ser Gln Gln Phe
    130                 135                 140

Ser Glu Cys Met Asp Leu Ala Leu Lys Ser Leu Thr Ser Gly Ala Gln
145                 150                 155                 160

Gln Ala Thr Thr

<210> SEQ ID NO 3
<211> LENGTH: 1235
<212> TYPE: DNA
<213> ORGANISM: Mus musculus
<220> FEATURE:
<221> NAME/KEY: CDS
<222> LOCATION: (482)...(973)
```

<400> SEQUENCE: 3

```
tgagaacgca aggacaaggg caggccctgg agcacagatg ccttctcctt atgccttccc      60
tgtgttcact agagccatcc ccctgcctcc ggaattccca cagatggatc gctctgtggc     120
ttcttaaaac ttccctgcag ggcactgacc ctcagcccct ctaagtcact tcttccccag     180
tgattgtact tttcaatcgg gcttcaaact ttcctctcat aaatcagca agcacttttcc    240 aagaaaagag agatgctcaa gatgccttcc tgtgtgccct gctttcccca ggccgagccg     300
aggctggcaa ccttttgaaa atgttttctg gagaaaagct gagcaatggt tttgccatgg     360
gcgggccttt gatctgcttc ctcatgacaa ccctttatat attgcctggt ggccatggcg     420
aacacaccag gctccagaga ccacaggcaa agcgggcctt cctcactctc ttaccgtcgc     480
```

```
c atg atc ttc cac aca gga aca acg aag cct acc ctg gtg ctg ctt tgc     529
  Met Ile Phe His Thr Gly Thr Thr Lys Pro Thr Leu Val Leu Leu Cys
   1               5                  10                  15 tgt ata gga acc tgg ctg gcc acc tgc agc ttg tcc ttc ggt gcc cca       577
Cys Ile Gly Thr Trp Leu Ala Thr Cys Ser Leu Ser Phe Gly Ala Pro
                 20                  25                  30 ata tcg aag gaa gac tta aga act aca att gac ctc ttg aaa caa gag       625
Ile Ser Lys Glu Asp Leu Arg Thr Thr Ile Asp Leu Leu Lys Gln Glu
         35                  40                  45 tct cag gat ctt tat aac aac tat agc ata aag cag gca tct ggg atg       673
Ser Gln Asp Leu Tyr Asn Asn Tyr Ser Ile Lys Gln Ala Ser Gly Met
     50                  55                  60 tca gca gac gaa tca ata cag ctg ccg tgt ttc agc ctg gac cgg gaa       721
Ser Ala Asp Glu Ser Ile Gln Leu Pro Cys Phe Ser Leu Asp Arg Glu
 65                  70                  75                  80 gca tta acc aac atc tcg gtc atc ata gca cat ctg gag aaa gtc aaa       769
Ala Leu Thr Asn Ile Ser Val Ile Ile Ala His Leu Glu Lys Val Lys
                 85                  90                  95 gtg ttg agc gag aac aca gta gat act tct tgg gtg ata aga tgg cta       817
Val Leu Ser Glu Asn Thr Val Asp Thr Ser Trp Val Ile Arg Trp Leu
                100                 105                 110 aca aac atc agc tgt ttc aac cca ctg aat tta aac att tct gtg cct       865
Thr Asn Ile Ser Cys Phe Asn Pro Leu Asn Leu Asn Ile Ser Val Pro
            115                 120                 125 gga aat act gat gaa tcc tat gat tgt aaa gtg ttc gtg ctt acg gtt       913
Gly Asn Thr Asp Glu Ser Tyr Asp Cys Lys Val Phe Val Leu Thr Val
        130                 135                 140 tta aag cag ttc tca aac tgc atg gca gaa ctg cag gct aag gac aat       961
Leu Lys Gln Phe Ser Asn Cys Met Ala Glu Leu Gln Ala Lys Asp Asn
145                 150                 155                 160 act aca tgc tga gtgatggggg ggggggggtg cagtgtcctc agcagtgcct          1013
Thr Thr Cys *
```

```
gtccttcgag ggctgagctt gcaacccagg acttaactcc aaagggactg tgcggtcatt    1073
actagtcatg ttatttatgt ttttattttg tccactgaaa tcttgttctg ctaccctgta    1133
gggactggaa gtggcagcta tatttattta tttatgtact gagtttgtta acgctccatg    1193
gaggagcctt cagagtctat ttaataaatt atattgacat ga                       1235
```

<210> SEQ ID NO 4
<211> LENGTH: 163
<212> TYPE: PRT
<213> ORGANISM: Mus musculus

<400> SEQUENCE: 4

```
Met Ile Phe His Thr Gly Thr Thr Lys Pro Thr Leu Val Leu Leu Cys
  1               5                  10                  15
```

```
Cys Ile Gly Thr Trp Leu Ala Thr Cys Ser Leu Ser Phe Gly Ala Pro
         20                  25                  30

Ile Ser Lys Glu Asp Leu Arg Thr Thr Ile Asp Leu Leu Lys Gln Glu
     35                  40                  45

Ser Gln Asp Leu Tyr Asn Asn Tyr Ser Ile Lys Gln Ala Ser Gly Met
 50                  55                  60

Ser Ala Asp Glu Ser Ile Gln Leu Pro Cys Phe Ser Leu Asp Arg Glu
 65                  70                  75                  80

Ala Leu Thr Asn Ile Ser Val Ile Ala His Leu Glu Lys Val Lys
             85                  90                  95

Val Leu Ser Glu Asn Thr Val Asp Thr Ser Trp Val Ile Arg Trp Leu
            100                 105                 110

Thr Asn Ile Ser Cys Phe Asn Pro Leu Asn Leu Asn Ile Ser Val Pro
            115                 120                 125

Gly Asn Thr Asp Glu Ser Tyr Asp Cys Lys Val Phe Val Leu Thr Val
        130                 135                 140

Leu Lys Gln Phe Ser Asn Cys Met Ala Glu Leu Gln Ala Lys Asp Asn
145                 150                 155                 160

Thr Thr Cys

<210> SEQ ID NO 5
<211> LENGTH: 2393
<212> TYPE: DNA
<213> ORGANISM: Homo sapiens
<220> FEATURE:
<221> NAME/KEY: CDS
<222> LOCATION: (66)...(2360)

<400> SEQUENCE: 5
tgtgtgtgca gtatgaaaat tgagacagga aggcagagtg tcagcttgtt ccacctcagc        60 tggga atg tgc atc agg caa ctc aag ttt ttc acc acg gca tgt gtc tgt       110
      Met Cys Ile Arg Gln Leu Lys Phe Phe Thr Thr Ala Cys Val Cys
        1               5                  10                  15 gaa tgt ccg caa aac att ctc tct ccc cag cct tca tgt gtt aac ctg        158
Glu Cys Pro Gln Asn Ile Leu Ser Pro Gln Pro Ser Cys Val Asn Leu
                 20                  25                  30 ggg atg atg tgg acc tgg gca ctg tgg atg ctc ccc tca ctc tgc aaa        206
Gly Met Met Trp Thr Trp Ala Leu Trp Met Leu Pro Ser Leu Cys Lys
             35                  40                  45 ttc agc ctg gca gct ctg cca gct aag cct gag aac att tcc tgt gtc        254
Phe Ser Leu Ala Ala Leu Pro Ala Lys Pro Glu Asn Ile Ser Cys Val
         50                  55                  60 tac tac tat agg aaa aat tta acc tgc act tgg agt cca gga aag gaa        302
Tyr Tyr Tyr Arg Lys Asn Leu Thr Cys Thr Trp Ser Pro Gly Lys Glu
 65                  70                  75 acc agt tat acc cag tac aca gtt aag aga act tac gct ttt gga gaa        350
Thr Ser Tyr Thr Gln Tyr Thr Val Lys Arg Thr Tyr Ala Phe Gly Glu
 80                  85                  90                  95 aaa cat gat aat tgt aca acc aat agt tct aca agt gaa aat cgt gct        398
Lys His Asp Asn Cys Thr Thr Asn Ser Ser Thr Ser Glu Asn Arg Ala
                100                 105                 110 tcg tgc tct ttt ttc ctt cca aga ata acg atc cca gat aat tat acc        446
Ser Cys Ser Phe Phe Leu Pro Arg Ile Thr Ile Pro Asp Asn Tyr Thr
            115                 120                 125 att gag gtg gaa gct gaa aat gga gat ggt gta att aaa tct cat atg        494
Ile Glu Val Glu Ala Glu Asn Gly Asp Gly Val Ile Lys Ser His Met
        130                 135                 140 aca tac tgg aga tta gag aac ata gcg aaa act gaa cca cct aag att        542
```

```
                                              -continued

Thr Tyr Trp Arg Leu Glu Asn Ile Ala Lys Thr Glu Pro Lys Ile
    145                 150                 155 ttc cgt gtg aaa cca gtt ttg ggc atc aaa cga atg att caa att gaa      590
Phe Arg Val Lys Pro Val Leu Gly Ile Lys Arg Met Ile Gln Ile Glu
160                 165                 170                 175 tgg ata aag cct gag ttg gcg cct gtt tca tct gat tta aaa tac aca      638
Trp Ile Lys Pro Glu Leu Ala Pro Val Ser Ser Asp Leu Lys Tyr Thr
                180                 185                 190 ctt cga ttc agg aca gtc aac agt acc agc tgg atg gaa gtc aac ttc      686
Leu Arg Phe Arg Thr Val Asn Ser Thr Ser Trp Met Glu Val Asn Phe
            195                 200                 205 gct aag aac cgt aag gat aaa aac caa acg tac aac ctc acg ggg ctg      734
Ala Lys Asn Arg Lys Asp Lys Asn Gln Thr Tyr Asn Leu Thr Gly Leu
        210                 215                 220 cag cct ttt aca gaa tat gtc ata gct ctg cga tgt gcg gtc aag gag      782
Gln Pro Phe Thr Glu Tyr Val Ile Ala Leu Arg Cys Ala Val Lys Glu
    225                 230                 235 tca aag ttc tgg agt gac tgg agc caa gaa aaa atg gga atg act gag      830
Ser Lys Phe Trp Ser Asp Trp Ser Gln Glu Lys Met Gly Met Thr Glu
240                 245                 250                 255 gaa gaa gct cca tgt ggc ctg gaa ctg tgg aga gtc ctg aaa cca gct      878
Glu Glu Ala Pro Cys Gly Leu Glu Leu Trp Arg Val Leu Lys Pro Ala
                260                 265                 270 gag gcg gat gga aga agg cca gtg cgg ttg tta tgg aag aag gca aga      926
Glu Ala Asp Gly Arg Arg Pro Val Arg Leu Leu Trp Lys Lys Ala Arg
            275                 280                 285 gga gcc cca gtc cta gag aaa aca ctt ggc tac aac ata tgg tac tat      974
Gly Ala Pro Val Leu Glu Lys Thr Leu Gly Tyr Asn Ile Trp Tyr Tyr
        290                 295                 300 cca gaa agc aac act aac ctc aca gaa aca atg aac act act aac cag     1022
Pro Glu Ser Asn Thr Asn Leu Thr Glu Thr Met Asn Thr Thr Asn Gln
    305                 310                 315 cag ctt gaa ctg cat ctg gga ggc gag agc ttt tgg gtg tct atg att     1070
Gln Leu Glu Leu His Leu Gly Gly Glu Ser Phe Trp Val Ser Met Ile
320                 325                 330                 335 tct tat aat tct ctt ggg aag tct cca gtg gcc acc ctg agg att cca     1118
Ser Tyr Asn Ser Leu Gly Lys Ser Pro Val Ala Thr Leu Arg Ile Pro
                340                 345                 350 gct att caa gaa aaa tca ttt cag tgc att gag gtc atg cag gcc tgc     1166
Ala Ile Gln Glu Lys Ser Phe Gln Cys Ile Glu Val Met Gln Ala Cys
            355                 360                 365 gtt gct gag gac cag cta gtg gtg aag tgg caa agc tct gct cta gac     1214
Val Ala Glu Asp Gln Leu Val Val Lys Trp Gln Ser Ser Ala Leu Asp
        370                 375                 380 gtg aac act tgg atg att gaa tgg ttt ccg gat gtg gac tca gag ccc     1262
Val Asn Thr Trp Met Ile Glu Trp Phe Pro Asp Val Asp Ser Glu Pro
    385                 390                 395 acc acc ctt tcc tgg gaa tct gtg tct cag gcc acg aac tgg acg atc     1310
Thr Thr Leu Ser Trp Glu Ser Val Ser Gln Ala Thr Asn Trp Thr Ile
400                 405                 410                 415 cag caa gat aaa tta aaa cct ttc tgg tgc tat aac atc tct gtg tat     1358
Gln Gln Asp Lys Leu Lys Pro Phe Trp Cys Tyr Asn Ile Ser Val Tyr
                420                 425                 430 cca atg ttg cat gac aaa gtt ggc gag cca tat tcc atc cag gct tat     1406
Pro Met Leu His Asp Lys Val Gly Glu Pro Tyr Ser Ile Gln Ala Tyr
            435                 440                 445 gcc aaa gaa ggc gtt cca tca gaa ggt cct gag acc aag gtg gag aac     1454
Ala Lys Glu Gly Val Pro Ser Glu Gly Pro Glu Thr Lys Val Glu Asn
        450                 455                 460 att ggc gtg aag acg gtc acg atc aca tgg aaa gag att ccc aag agt     1502
```

```
                Ile Gly Val Lys Thr Val Thr Ile Thr Trp Lys Glu Ile Pro Lys Ser
                    465                 470                 475 gag aga aag ggt atc atc tgc aac tac acc atc ttt tac caa gct gaa          1550
Glu Arg Lys Gly Ile Ile Cys Asn Tyr Thr Ile Phe Tyr Gln Ala Glu
480                 485                 490                 495 ggt gga aaa gga ttc tcc aag aca gtc aat tcc agc atc ttg cag tac          1598
Gly Gly Lys Gly Phe Ser Lys Thr Val Asn Ser Ser Ile Leu Gln Tyr
                500                 505                 510 ggc ctg gag tcc ctg aaa cga aag acc tct tac att gtt cag gtc atg          1646
Gly Leu Glu Ser Leu Lys Arg Lys Thr Ser Tyr Ile Val Gln Val Met
            515                 520                 525 gcc agc acc agt gct ggg gga acc aac ggg acc agc ata aat ttc aag          1694
Ala Ser Thr Ser Ala Gly Gly Thr Asn Gly Thr Ser Ile Asn Phe Lys
        530                 535                 540 aca ttg tca ttc agt gtc ttt gag att atc ctc ata act tct ctg att          1742
Thr Leu Ser Phe Ser Val Phe Glu Ile Ile Leu Ile Thr Ser Leu Ile
    545                 550                 555 ggt gga ggc ctt ctt att ctc att atc ctg aca gtg gca tat ggt ctc          1790
Gly Gly Gly Leu Leu Ile Leu Ile Ile Leu Thr Val Ala Tyr Gly Leu
560                 565                 570                 575 aaa aaa ccc aac aaa ttg act cat ctg tgt tgg ccc acc gtt ccc aac          1838
Lys Lys Pro Asn Lys Leu Thr His Leu Cys Trp Pro Thr Val Pro Asn
                580                 585                 590 cct gct gaa agt agt ata gcc aca tgg cat gga gat gat ttc aag gat          1886
Pro Ala Glu Ser Ser Ile Ala Thr Trp His Gly Asp Asp Phe Lys Asp
                595                 600                 605 aag cta aac ctg aag gag tct gat gac tct gtg aac aca gaa gac agg          1934
Lys Leu Asn Leu Lys Glu Ser Asp Asp Ser Val Asn Thr Glu Asp Arg
            610                 615                 620 atc tta aaa cca tgt tcc acc ccc agt gac aag ttg gtg att gac aag          1982
Ile Leu Lys Pro Cys Ser Thr Pro Ser Asp Lys Leu Val Ile Asp Lys
        625                 630                 635 ttg gtg gtg aac ttt ggg aat gtt ctg caa gaa att ttc aca gat gaa          2030
Leu Val Val Asn Phe Gly Asn Val Leu Gln Glu Ile Phe Thr Asp Glu
640                 645                 650                 655 gcc aga acg ggt cag gaa aac aat tta gga ggg gaa aag aat ggg tat          2078
Ala Arg Thr Gly Gln Glu Asn Asn Leu Gly Gly Glu Lys Asn Gly Tyr
                660                 665                 670 gtg acc tgc ccc ttc agg cct gat tgt ccc ctg ggg aaa agt ttt gag          2126
Val Thr Cys Pro Phe Arg Pro Asp Cys Pro Leu Gly Lys Ser Phe Glu
                675                 680                 685 gag ctc cca gtt tca cct gag att ccg ccc aga aaa tcc caa tac cta          2174
Glu Leu Pro Val Ser Pro Glu Ile Pro Pro Arg Lys Ser Gln Tyr Leu
            690                 695                 700 cgt tcg agg atg cca gag ggg acc cgc cca gaa gcc aaa gag cag ctt          2222
Arg Ser Arg Met Pro Glu Gly Thr Arg Pro Glu Ala Lys Glu Gln Leu
        705                 710                 715 ctc ttt tct ggt caa agt tta gta cca gat cat ctg tgt gag gaa gga          2270
Leu Phe Ser Gly Gln Ser Leu Val Pro Asp His Leu Cys Glu Glu Gly
720                 725                 730                 735 gcc cca aat cca tat ttg aaa aat tca gtg aca gcc agg gaa ttt ctt          2318
Ala Pro Asn Pro Tyr Leu Lys Asn Ser Val Thr Ala Arg Glu Phe Leu
                740                 745                 750 gtg tct gaa aaa ctt cca gag cac acc aag gga gaa gtc taa               2360
Val Ser Glu Lys Leu Pro Glu His Thr Lys Gly Glu Val *
                755                 760 atgcgaccat agcatgagac cctcggggcc tca                                  2393

<210> SEQ ID NO 6
<211> LENGTH: 764
```

<212> TYPE: PRT
<213> ORGANISM: Homo sapiens

<400> SEQUENCE: 6

Met Cys Ile Arg Gln Leu Lys Phe Phe Thr Thr Ala Cys Val Cys Glu
1               5                   10                  15

Cys Pro Gln Asn Ile Leu Ser Pro Gln Pro Ser Cys Val Asn Leu Gly
            20                  25                  30

Met Met Trp Thr Trp Ala Leu Trp Met Leu Pro Ser Leu Cys Lys Phe
        35                  40                  45

Ser Leu Ala Ala Leu Pro Ala Lys Pro Glu Asn Ile Ser Cys Val Tyr
    50                  55                  60

Tyr Tyr Arg Lys Asn Leu Thr Cys Thr Trp Ser Pro Gly Lys Glu Thr
65                  70                  75                  80

Ser Tyr Thr Gln Tyr Thr Val Lys Arg Thr Tyr Ala Phe Gly Glu Lys
                85                  90                  95

His Asp Asn Cys Thr Thr Asn Ser Ser Thr Ser Glu Asn Arg Ala Ser
            100                 105                 110

Cys Ser Phe Phe Leu Pro Arg Ile Thr Ile Pro Asp Asn Tyr Thr Ile
        115                 120                 125

Glu Val Glu Ala Glu Asn Gly Asp Gly Val Ile Lys Ser His Met Thr
    130                 135                 140

Tyr Trp Arg Leu Glu Asn Ile Ala Lys Thr Glu Pro Pro Lys Ile Phe
145                 150                 155                 160

Arg Val Lys Pro Val Leu Gly Ile Lys Arg Met Ile Gln Ile Glu Trp
                165                 170                 175

Ile Lys Pro Glu Leu Ala Pro Val Ser Ser Asp Leu Lys Tyr Thr Leu
            180                 185                 190

Arg Phe Arg Thr Val Asn Ser Thr Ser Trp Met Glu Val Asn Phe Ala
        195                 200                 205

Lys Asn Arg Lys Asp Lys Asn Gln Thr Tyr Asn Leu Thr Gly Leu Gln
    210                 215                 220

Pro Phe Thr Glu Tyr Val Ile Ala Leu Arg Cys Ala Val Lys Glu Ser
225                 230                 235                 240

Lys Phe Trp Ser Asp Trp Ser Gln Glu Lys Met Gly Met Thr Glu Glu
                245                 250                 255

Glu Ala Pro Cys Gly Leu Glu Leu Trp Arg Val Leu Lys Pro Ala Glu
            260                 265                 270

Ala Asp Gly Arg Arg Pro Val Arg Leu Leu Trp Lys Lys Ala Arg Gly
        275                 280                 285

Ala Pro Val Leu Glu Lys Thr Leu Gly Tyr Asn Ile Trp Tyr Tyr Pro
    290                 295                 300

Glu Ser Asn Thr Asn Leu Thr Glu Thr Met Asn Thr Thr Asn Gln Gln
305                 310                 315                 320

Leu Glu Leu His Leu Gly Gly Glu Ser Phe Trp Val Ser Met Ile Ser
                325                 330                 335

Tyr Asn Ser Leu Gly Lys Ser Pro Val Ala Thr Leu Arg Ile Pro Ala
            340                 345                 350

Ile Gln Glu Lys Ser Phe Gln Cys Ile Glu Val Met Gln Ala Cys Val
        355                 360                 365

Ala Glu Asp Gln Leu Val Val Lys Trp Gln Ser Ser Ala Leu Asp Val
    370                 375                 380

Asn Thr Trp Met Ile Glu Trp Phe Pro Asp Val Asp Ser Glu Pro Thr
385                 390                 395                 400

Thr Leu Ser Trp Glu Ser Val Ser Gln Ala Thr Asn Trp Thr Ile Gln
                405                 410                 415

Gln Asp Lys Leu Lys Pro Phe Trp Cys Tyr Asn Ile Ser Val Tyr Pro
            420                 425                 430

Met Leu His Asp Lys Val Gly Glu Pro Tyr Ser Ile Gln Ala Tyr Ala
        435                 440                 445

Lys Glu Gly Val Pro Ser Glu Gly Pro Glu Thr Lys Val Glu Asn Ile
    450                 455                 460

Gly Val Lys Thr Val Thr Ile Thr Trp Lys Glu Ile Pro Lys Ser Glu
465                 470                 475                 480

Arg Lys Gly Ile Ile Cys Asn Tyr Thr Ile Phe Tyr Gln Ala Glu Gly
                485                 490                 495

Gly Lys Gly Phe Ser Lys Thr Val Asn Ser Ser Ile Leu Gln Tyr Gly
            500                 505                 510

Leu Glu Ser Leu Lys Arg Lys Thr Ser Tyr Ile Val Gln Val Met Ala
        515                 520                 525

Ser Thr Ser Ala Gly Gly Thr Asn Gly Thr Ser Ile Asn Phe Lys Thr
    530                 535                 540

Leu Ser Phe Ser Val Phe Glu Ile Ile Leu Ile Thr Ser Leu Ile Gly
545                 550                 555                 560

Gly Gly Leu Leu Ile Leu Ile Ile Leu Thr Val Ala Tyr Gly Leu Lys
                565                 570                 575

Lys Pro Asn Lys Leu Thr His Leu Cys Trp Pro Thr Val Pro Asn Pro
            580                 585                 590

Ala Glu Ser Ser Ile Ala Thr Trp His Gly Asp Asp Phe Lys Asp Lys
        595                 600                 605

Leu Asn Leu Lys Glu Ser Asp Asp Ser Val Asn Thr Glu Asp Arg Ile
    610                 615                 620

Leu Lys Pro Cys Ser Thr Pro Ser Asp Lys Leu Val Ile Asp Lys Leu
625                 630                 635                 640

Val Val Asn Phe Gly Asn Val Leu Gln Glu Ile Phe Thr Asp Glu Ala
                645                 650                 655

Arg Thr Gly Gln Glu Asn Asn Leu Gly Gly Glu Lys Asn Gly Tyr Val
            660                 665                 670

Thr Cys Pro Phe Arg Pro Asp Cys Pro Leu Gly Lys Ser Phe Glu Glu
        675                 680                 685

Leu Pro Val Ser Pro Glu Ile Pro Pro Arg Lys Ser Gln Tyr Leu Arg
    690                 695                 700

Ser Arg Met Pro Glu Gly Thr Arg Pro Glu Ala Lys Glu Gln Leu Leu
705                 710                 715                 720

Phe Ser Gly Gln Ser Leu Val Pro Asp His Leu Cys Glu Glu Gly Ala
                725                 730                 735

Pro Asn Pro Tyr Leu Lys Asn Ser Val Thr Ala Arg Glu Phe Leu Val
            740                 745                 750

Ser Glu Lys Leu Pro Glu His Thr Lys Gly Glu Val
        755                 760

<210> SEQ ID NO 7
<211> LENGTH: 2903
<212> TYPE: DNA
<213> ORGANISM: Homo sapiens
<220> FEATURE:
<221> NAME/KEY: CDS
<222> LOCATION: (497)...(2485)

<400> SEQUENCE: 7

```
tgaaaagaca tgtgtgtgca gtatgaaaat tgagacagga aggcagagtg tcagcttgtt      60
ccacctcagc tgggaatgtg catcaggcaa ctcaagtttt tcaccacggc atgtgtctgt     120
gaatgtccgc aaaacattag tttcactctt gtcgccaggt tggagtacaa tggcacgatc     180
ttggctcact gcaacctctg cctcccgggt tcaagcgatt ctcctgcctc agcctcccga     240
gtagctggga ttacagttaa caataatgca atccatttcc cagcataagt gggtaagtgc     300
cactttgact tgggctgggc ttaaaagcac aagaaaagct cgcagacaat cagagtggaa     360
acactcccac atcttagtgt ggataaatta aagtccagat tgttcttcct gtcctgactt     420
gtgctgtggg aggtggagtt gcctttgatg caaatccttt gagccagcag aacatctgtg     480
gaacatcccc tgatac atg aag ctc tct ccc cag cct tca tgt gtt aac ctg    532
               Met Lys Leu Ser Pro Gln Pro Ser Cys Val Asn Leu
                 1               5                  10
```

```
ggg atg atg tgg acc tgg gca ctg tgg atg ctc cct tca ctc tgc aaa       580
Gly Met Met Trp Thr Trp Ala Leu Trp Met Leu Pro Ser Leu Cys Lys
         15                  20                  25 ttc agc ctg gca gct ctg cca gct aag cct gag aac att tcc tgt gtc       628
Phe Ser Leu Ala Ala Leu Pro Ala Lys Pro Glu Asn Ile Ser Cys Val
 30                  35                  40 tac tac tat agg aaa aat tta acc tgc act tgg agt cca gga aag gaa       676
Tyr Tyr Tyr Arg Lys Asn Leu Thr Cys Thr Trp Ser Pro Gly Lys Glu
 45                  50                  55                  60 acc agt tat acc cag tac aca gtt aag aga act tac gct ttt gga gaa       724
Thr Ser Tyr Thr Gln Tyr Thr Val Lys Arg Thr Tyr Ala Phe Gly Glu
             65                  70                  75 aaa cat gat aat tgt aca acc aat agt tct aca agt gaa aat cgt gct       772
Lys His Asp Asn Cys Thr Thr Asn Ser Ser Thr Ser Glu Asn Arg Ala
         80                  85                  90 tcg tgc tct ttt ttc ctt cca aga ata acg atc cca gat aat tat acc       820
Ser Cys Ser Phe Phe Leu Pro Arg Ile Thr Ile Pro Asp Asn Tyr Thr
     95                  100                 105 att gag gtg gaa gct gaa aat gga gat ggt gta att aaa tct cat atg       868
Ile Glu Val Glu Ala Glu Asn Gly Asp Gly Val Ile Lys Ser His Met
110                 115                 120 aca tac tgg aga tta gag aac ata gcg aaa act gaa cca cct aag att       916
Thr Tyr Trp Arg Leu Glu Asn Ile Ala Lys Thr Glu Pro Pro Lys Ile
125                 130                 135                 140 ttc cgt gtg aaa cca gtt ttg ggc atc aaa cga atg att caa att gaa       964
Phe Arg Val Lys Pro Val Leu Gly Ile Lys Arg Met Ile Gln Ile Glu
            145                 150                 155 tgg ata aag cct gag ttg gcg cct gtt tca tct gat tta aaa tac aca      1012
Trp Ile Lys Pro Glu Leu Ala Pro Val Ser Ser Asp Leu Lys Tyr Thr
        160                 165                 170 ctt cga ttc agg aca gtc aac agt acc agc tgg atg gaa gtc aac ttc      1060
Leu Arg Phe Arg Thr Val Asn Ser Thr Ser Trp Met Glu Val Asn Phe
        175                 180                 185 gct aag aac cgt aag gat aaa aac caa acg tac aac ctc acg ggg ctg      1108
Ala Lys Asn Arg Lys Asp Lys Asn Gln Thr Tyr Asn Leu Thr Gly Leu
    190                 195                 200 cag cct ttt aca gaa tat gtc ata gct ctg cga tgt gcg gtc aag gag      1156
Gln Pro Phe Thr Glu Tyr Val Ile Ala Leu Arg Cys Ala Val Lys Glu
205                 210                 215                 220 tca aag ttc tgg agt gac tgg agc caa gaa aaa atg gga atg act gag      1204
Ser Lys Phe Trp Ser Asp Trp Ser Gln Glu Lys Met Gly Met Thr Glu
            225                 230                 235 gaa gaa gct cca tgt ggc ctg gaa ctg tgg aga gtc ctg aaa cca gct      1252
Glu Glu Ala Pro Cys Gly Leu Glu Leu Trp Arg Val Leu Lys Pro Ala
        240                 245                 250
```

```
                                                        -continued gag gcg gat gga aga agg cca gtg cgg ttg tta tgg aag aag gca aga           1300
Glu Ala Asp Gly Arg Arg Pro Val Arg Leu Leu Trp Lys Lys Ala Arg
        255                 260                 265 gga gcc cca gtc cta gag aaa aca ctt ggc tac aac ata tgg tac tat           1348
Gly Ala Pro Val Leu Glu Lys Thr Leu Gly Tyr Asn Ile Trp Tyr Tyr
270                 275                 280 cca gaa agc aac act aac ctc aca gaa aca atg aac act act aac cag           1396
Pro Glu Ser Asn Thr Asn Leu Thr Glu Thr Met Asn Thr Thr Asn Gln
285                 290                 295                 300 cag ctt gaa ctg cat ctg gga ggc gag agc ttt tgg gtg tct atg att           1444
Gln Leu Glu Leu His Leu Gly Gly Glu Ser Phe Trp Val Ser Met Ile
            305                 310                 315 tct tat aat tct ctt ggg aag tct cca gtg gcc acc ctg agg att cca           1492
Ser Tyr Asn Ser Leu Gly Lys Ser Pro Val Ala Thr Leu Arg Ile Pro
        320                 325                 330 gct att caa gaa aaa tca ttt cag tgc att gag gtc atg cag gcc tgc           1540
Ala Ile Gln Glu Lys Ser Phe Gln Cys Ile Glu Val Met Gln Ala Cys
        335                 340                 345 gtt gct gag gac cag cta gtg gtg aag tgg caa agc tct gct cta gac           1588
Val Ala Glu Asp Gln Leu Val Val Lys Trp Gln Ser Ser Ala Leu Asp
350                 355                 360 gtg aac act tgg atg att gaa tgg ttt ccg gat gtg gac tca gag ccc           1636
Val Asn Thr Trp Met Ile Glu Trp Phe Pro Asp Val Asp Ser Glu Pro
365                 370                 375                 380 acc acc ctt tcc tgg gaa tct gtg tct cag gcc acg aac tgg acg atc           1684
Thr Thr Leu Ser Trp Glu Ser Val Ser Gln Ala Thr Asn Trp Thr Ile
            385                 390                 395 cag caa gat aaa tta aaa cct ttc tgg tgc tat aac atc tct gtg tat           1732
Gln Gln Asp Lys Leu Lys Pro Phe Trp Cys Tyr Asn Ile Ser Val Tyr
        400                 405                 410 cca atg ttg cat gac aaa gtt ggc gag cca tat tcc atc cag gct tat           1780
Pro Met Leu His Asp Lys Val Gly Glu Pro Tyr Ser Ile Gln Ala Tyr
        415                 420                 425 gcc aaa gaa ggc gtt cca tca gaa ggt cct gag acc aag gtg gag aac           1828
Ala Lys Glu Gly Val Pro Ser Glu Gly Pro Glu Thr Lys Val Glu Asn
        430                 435                 440 att ggc gtg aag acg gtc acg atc aca tgg aaa gag att ccc aag agt           1876
Ile Gly Val Lys Thr Val Thr Ile Thr Trp Lys Glu Ile Pro Lys Ser
445                 450                 455                 460 gag aga aag ggt atc atc tgc aac tac acc atc ttt tac caa gct gaa           1924
Glu Arg Lys Gly Ile Ile Cys Asn Tyr Thr Ile Phe Tyr Gln Ala Glu
            465                 470                 475 ggt gga aaa gga ttc tcc aag aca gtc aat ccc agc atc ttg cag tac           1972
Gly Gly Lys Gly Phe Ser Lys Thr Val Asn Ser Ser Ile Leu Gln Tyr
        480                 485                 490 ggc ctg gag tcc ctg aaa cga aag acc tct tac att gtt cag gtc atg           2020
Gly Leu Glu Ser Leu Lys Arg Lys Thr Ser Tyr Ile Val Gln Val Met
        495                 500                 505 gcc agc acc agt gct ggg gga acc aac ggg acc agc ata aat ttc aag           2068
Ala Ser Thr Ser Ala Gly Gly Thr Asn Gly Thr Ser Ile Asn Phe Lys
        510                 515                 520 aca ttg tca ttc agt gtc ttt gag att atc ctc ata act tct ctg att           2116
Thr Leu Ser Phe Ser Val Phe Glu Ile Ile Leu Ile Thr Ser Leu Ile
525                 530                 535                 540 ggt gga ggc ctt ctt att ctc att atc ctg aca gtg gca tat ggt ctc           2164
Gly Gly Gly Leu Leu Ile Leu Ile Ile Leu Thr Val Ala Tyr Gly Leu
            545                 550                 555 aaa aaa ccc aac aaa ttg act cat ctg tgt tgg ccc acc gtt ccc aac           2212
Lys Lys Pro Asn Lys Leu Thr His Leu Cys Trp Pro Thr Val Pro Asn
        560                 565                 570
```

```
cct gct gaa agt agt ata gcc aca tgg cat gga gat gat ttc aag gat       2260
Pro Ala Glu Ser Ser Ile Ala Thr Trp His Gly Asp Asp Phe Lys Asp
            575                 580                 585 aag cta aac ctg aag gag tct gat gac tct gtg aac aca gaa gac agg       2308
Lys Leu Asn Leu Lys Glu Ser Asp Asp Ser Val Asn Thr Glu Asp Arg
        590                 595                 600 atc tta aaa cca tgt tcc acc ccc agt gac aag ttg gtg att gac aag       2356
Ile Leu Lys Pro Cys Ser Thr Pro Ser Asp Lys Leu Val Ile Asp Lys
605                 610                 615                 620 ttg gtg gtg aac ttt ggg aat gtt ctg caa gaa att ttc aca gat gaa       2404
Leu Val Val Asn Phe Gly Asn Val Leu Gln Glu Ile Phe Thr Asp Glu
                625                 630                 635 gcc aga acg ggt cag gaa aac aat tta gga ggg gaa aag aat ggg act       2452
Ala Arg Thr Gly Gln Glu Asn Asn Leu Gly Gly Glu Lys Asn Gly Thr
        640                 645                 650 aga att ctg tct tcc tgc cca act tca ata taa gtgtggacta aaatgcgaga     2505
Arg Ile Leu Ser Ser Cys Pro Thr Ser Ile  *
655                 660 aaggtgtcct gtggtctatg caaattagaa aggacatgca gagttttcca actaggaaga    2565
ctgaatctgt ggccccaaga gaaccatctc tgaagactgg gtatgtggtc ttttccacac    2625
atggaccacc tacggatgca atctgtaatg catgtgcatg agaagtctgt tattaagtag    2685
agtgtgaaaa catggttatg gtaataggaa cagcttttaa aatgcttttg tatttgggcc    2745
tttcatacaa aaaagccata ataccatttt catgtaatgc tatacttcta tactattttc    2805
atgtaatact atacttctat actatttca tgtaatacta tacttctata ctattttcat     2865
gtaatactat acttctatat taaagtttta cccactca                            2903

<210> SEQ ID NO 8
<211> LENGTH: 662
<212> TYPE: PRT
<213> ORGANISM: Homo sapiens

<400> SEQUENCE: 8

Met Lys Leu Ser Pro Gln Pro Ser Cys Val Asn Leu Gly Met Met Trp
1               5                   10                  15

Thr Trp Ala Leu Trp Met Leu Pro Ser Leu Cys Lys Phe Ser Leu Ala
            20                  25                  30

Ala Leu Pro Ala Lys Pro Glu Asn Ile Ser Cys Val Tyr Tyr Tyr Arg
        35                  40                  45

Lys Asn Leu Thr Cys Thr Trp Ser Pro Gly Lys Glu Thr Ser Tyr Thr
    50                  55                  60

Gln Tyr Thr Val Lys Arg Thr Tyr Ala Phe Gly Glu Lys His Asp Asn
65                  70                  75                  80

Cys Thr Thr Asn Ser Ser Thr Ser Glu Asn Arg Ala Ser Cys Ser Phe
                85                  90                  95

Phe Leu Pro Arg Ile Thr Ile Pro Asp Asn Tyr Thr Ile Glu Val Glu
            100                 105                 110

Ala Glu Asn Gly Asp Gly Val Ile Lys Ser His Met Thr Tyr Trp Arg
        115                 120                 125

Leu Glu Asn Ile Ala Lys Thr Glu Pro Pro Lys Ile Phe Arg Val Lys
    130                 135                 140

Pro Val Leu Gly Ile Lys Arg Met Ile Gln Ile Glu Trp Ile Lys Pro
145                 150                 155                 160

Glu Leu Ala Pro Val Ser Ser Asp Leu Lys Tyr Thr Leu Arg Phe Arg
                165                 170                 175

Thr Val Asn Ser Thr Ser Trp Met Glu Val Asn Phe Ala Lys Asn Arg
```

```
                180                 185                 190
Lys Asp Lys Asn Gln Thr Tyr Asn Leu Thr Gly Leu Gln Pro Phe Thr
            195                 200                 205

Glu Tyr Val Ile Ala Leu Arg Cys Ala Val Lys Glu Ser Lys Phe Trp
210                 215                 220

Ser Asp Trp Ser Gln Glu Lys Met Gly Met Thr Glu Glu Ala Pro
225                 230                 235                 240

Cys Gly Leu Glu Leu Trp Arg Val Leu Lys Pro Ala Glu Ala Asp Gly
                245                 250                 255

Arg Arg Pro Val Arg Leu Leu Trp Lys Lys Ala Arg Gly Ala Pro Val
            260                 265                 270

Leu Glu Lys Thr Leu Gly Tyr Asn Ile Trp Tyr Tyr Pro Glu Ser Asn
        275                 280                 285

Thr Asn Leu Thr Glu Thr Met Asn Thr Thr Asn Gln Gln Leu Glu Leu
    290                 295                 300

His Leu Gly Gly Glu Ser Phe Trp Val Ser Met Ile Ser Tyr Asn Ser
305                 310                 315                 320

Leu Gly Lys Ser Pro Val Ala Thr Leu Arg Ile Pro Ala Ile Gln Glu
                325                 330                 335

Lys Ser Phe Gln Cys Ile Glu Val Met Gln Ala Cys Val Ala Glu Asp
            340                 345                 350

Gln Leu Val Val Lys Trp Gln Ser Ala Leu Asp Val Asn Thr Trp
        355                 360                 365

Met Ile Glu Trp Phe Pro Asp Val Asp Ser Gly Pro Thr Thr Leu Ser
    370                 375                 380

Trp Glu Ser Val Ser Gln Ala Thr Asn Trp Thr Ile Gln Gln Asp Lys
385                 390                 395                 400

Leu Lys Pro Phe Trp Cys Tyr Asn Ile Ser Val Tyr Pro Met Leu His
                405                 410                 415

Asp Lys Val Gly Glu Pro Tyr Ser Ile Gln Ala Tyr Ala Lys Glu Gly
            420                 425                 430

Val Pro Ser Glu Gly Pro Glu Thr Lys Val Glu Asn Ile Gly Val Lys
        435                 440                 445

Thr Val Thr Ile Thr Trp Lys Glu Ile Pro Lys Ser Glu Arg Lys Gly
    450                 455                 460

Ile Ile Cys Asn Tyr Thr Ile Phe Tyr Gln Ala Glu Gly Gly Lys Gly
465                 470                 475                 480

Phe Ser Lys Thr Val Asn Ser Ser Ile Leu Gln Tyr Gly Leu Glu Ser
                485                 490                 495

Leu Lys Arg Lys Thr Ser Tyr Ile Val Gln Val Met Ala Ser Thr Ser
            500                 505                 510

Ala Gly Gly Thr Asn Gly Thr Ser Ile Asn Phe Lys Thr Leu Ser Phe
        515                 520                 525

Ser Val Phe Glu Ile Ile Leu Ile Thr Ser Leu Ile Gly Gly Gly Leu
    530                 535                 540

Leu Ile Leu Ile Ile Leu Thr Val Ala Tyr Gly Leu Lys Lys Pro Asn
545                 550                 555                 560

Lys Leu Thr His Leu Cys Trp Pro Thr Val Pro Asn Pro Ala Glu Ser
                565                 570                 575

Ser Ile Ala Thr Trp His Gly Asp Asp Phe Lys Asp Lys Leu Asn Leu
            580                 585                 590

Lys Glu Ser Asp Asp Ser Val Asn Thr Glu Asp Arg Ile Leu Lys Pro
        595                 600                 605
```

```
Cys Ser Thr Pro Ser Asp Lys Leu Val Ile Asp Lys Leu Val Val Asn
        610                 615                 620
Phe Gly Asn Val Leu Gln Glu Ile Phe Thr Asp Glu Ala Arg Thr Gly
625                 630                 635                 640
Gln Glu Asn Asn Leu Gly Gly Glu Lys Asn Gly Thr Arg Ile Leu Ser
                645                 650                 655
Ser Cys Pro Thr Ser Ile
                660

<210> SEQ ID NO 9
<211> LENGTH: 975
<212> TYPE: DNA
<213> ORGANISM: Homo sapiens
<220> FEATURE:
<221> NAME/KEY: CDS
<222> LOCATION: (1)...(975)
<221> NAME/KEY: misc_feature
<222> LOCATION: (1)...(975)
<223> OTHER INFORMATION: soluble IL-31RA "long" form

<400> SEQUENCE: 9
```

| | | | | | | | | | | | | | | | | |
|---|---|---|---|---|---|---|---|---|---|---|---|---|---|---|---|---|
| atg | atg | tgg | acc | tgg | gca | ctg | tgg | atg | ctc | ccc | tca | ctc | tgc | aaa | ttc | 48 |
| Met | Met | Trp | Thr | Trp | Ala | Leu | Trp | Met | Leu | Pro | Ser | Leu | Cys | Lys | Phe | |
| 1 | | | | 5 | | | | | 10 | | | | | 15 | | |
| agc | ctg | gca | gct | ctg | cca | gct | aag | cct | gag | aac | att | tcc | tgt | gtc | tac | 96 |
| Ser | Leu | Ala | Ala | Leu | Pro | Ala | Lys | Pro | Glu | Asn | Ile | Ser | Cys | Val | Tyr | |
| | | | 20 | | | | | 25 | | | | | 30 | | | |
| tac | tat | agg | aaa | aat | tta | acc | tgc | act | tgg | agt | cca | gga | aag | gaa | acc | 144 |
| Tyr | Tyr | Arg | Lys | Asn | Leu | Thr | Cys | Thr | Trp | Ser | Pro | Gly | Lys | Glu | Thr | |
| | 35 | | | | | 40 | | | | | 45 | | | | | |
| agt | tat | acc | cag | tac | aca | gtt | aag | aga | act | tac | gct | ttt | gga | gaa | aaa | 192 |
| Ser | Tyr | Thr | Gln | Tyr | Thr | Val | Lys | Arg | Thr | Tyr | Ala | Phe | Gly | Glu | Lys | |
| 50 | | | | | 55 | | | | | 60 | | | | | | |
| cat | gat | aat | tgt | aca | acc | aat | agt | tct | aca | agt | gaa | aat | cgt | gct | tcg | 240 |
| His | Asp | Asn | Cys | Thr | Thr | Asn | Ser | Ser | Thr | Ser | Glu | Asn | Arg | Ala | Ser | |
| 65 | | | | | 70 | | | | | 75 | | | | | 80 | |
| tgc | tct | ttt | ttc | ctt | cca | aga | ata | acg | atc | cca | gat | aat | tat | acc | att | 288 |
| Cys | Ser | Phe | Phe | Leu | Pro | Arg | Ile | Thr | Ile | Pro | Asp | Asn | Tyr | Thr | Ile | |
| | | | | 85 | | | | | 90 | | | | | 95 | | |
| gag | gtg | gaa | gct | gaa | aat | gga | gat | ggt | gta | att | aaa | tct | cat | atg | aca | 336 |
| Glu | Val | Glu | Ala | Glu | Asn | Gly | Asp | Gly | Val | Ile | Lys | Ser | His | Met | Thr | |
| | | | 100 | | | | | 105 | | | | | 110 | | | |
| tac | tgg | aga | tta | gag | aac | ata | gcg | aaa | act | gaa | cca | cct | aag | att | ttc | 384 |
| Tyr | Trp | Arg | Leu | Glu | Asn | Ile | Ala | Lys | Thr | Glu | Pro | Pro | Lys | Ile | Phe | |
| | | 115 | | | | | 120 | | | | | 125 | | | | |
| cgt | gtg | aaa | cca | gtt | ttg | ggc | atc | aaa | cga | atg | att | caa | att | gaa | tgg | 432 |
| Arg | Val | Lys | Pro | Val | Leu | Gly | Ile | Lys | Arg | Met | Ile | Gln | Ile | Glu | Trp | |
| | 130 | | | | | 135 | | | | | 140 | | | | | |
| ata | aag | cct | gag | ttg | gcg | cct | gtt | tca | tct | gat | tta | aaa | tac | aca | ctt | 480 |
| Ile | Lys | Pro | Glu | Leu | Ala | Pro | Val | Ser | Ser | Asp | Leu | Lys | Tyr | Thr | Leu | |
| 145 | | | | | 150 | | | | | 155 | | | | | 160 | |
| cga | ttc | agg | aca | gtc | aac | agt | acc | agc | tgg | atg | gaa | gtc | aac | ttc | gct | 528 |
| Arg | Phe | Arg | Thr | Val | Asn | Ser | Thr | Ser | Trp | Met | Glu | Val | Asn | Phe | Ala | |
| | | | | 165 | | | | | 170 | | | | | 175 | | |
| aag | aac | cgt | aag | gat | aaa | aac | caa | acg | tac | aac | ctc | acg | ggg | ctg | cag | 576 |
| Lys | Asn | Arg | Lys | Asp | Lys | Asn | Gln | Thr | Tyr | Asn | Leu | Thr | Gly | Leu | Gln | |
| | | | 180 | | | | | 185 | | | | | 190 | | | |
| cct | ttt | aca | gaa | tat | gtc | ata | gct | ctg | cga | tgt | gcg | gtc | aag | gag | tca | 624 |
| Pro | Phe | Thr | Glu | Tyr | Val | Ile | Ala | Leu | Arg | Cys | Ala | Val | Lys | Glu | Ser | |
| | | 195 | | | | | 200 | | | | | 205 | | | | |
| aag | ttc | tgg | agt | gac | tgg | agc | caa | gaa | aaa | atg | gga | atg | act | gag | gaa | 672 |
| Lys | Phe | Trp | Ser | Asp | Trp | Ser | Gln | Glu | Lys | Met | Gly | Met | Thr | Glu | Glu | |

```
                     210                 215                 220
gaa gct cca tgt ggc ctg gaa ctg tgg aga gtc ctg aaa cca gct gag      720
Glu Ala Pro Cys Gly Leu Glu Leu Trp Arg Val Leu Lys Pro Ala Glu
225                 230                 235                 240 gcg gat gga aga agg cca gtg cgg ttg tta tgg aag aag gca aga gga      768
Ala Asp Gly Arg Arg Pro Val Arg Leu Leu Trp Lys Lys Ala Arg Gly
                245                 250                 255 gcc cca gtc cta gag aaa aca ctt ggc tac aac ata tgg tac tat cca      816
Ala Pro Val Leu Glu Lys Thr Leu Gly Tyr Asn Ile Trp Tyr Tyr Pro
            260                 265                 270 gaa agc aac act aac ctc aca gaa aca atg aac act act aac cag cag      864
Glu Ser Asn Thr Asn Leu Thr Glu Thr Met Asn Thr Thr Asn Gln Gln
        275                 280                 285 ctt gaa ctg cat ctg gga ggc gag agc ttt tgg gtg tct atg att tct      912
Leu Glu Leu His Leu Gly Gly Glu Ser Phe Trp Val Ser Met Ile Ser
    290                 295                 300 tat aat tct ctt ggg aag tct cca gtg gcc acc ctg agg att cca gct      960
Tyr Asn Ser Leu Gly Lys Ser Pro Val Ala Thr Leu Arg Ile Pro Ala
305                 310                 315                 320 att caa gaa aaa tag                                                  975
Ile Gln Glu Lys *

<210> SEQ ID NO 10
<211> LENGTH: 324
<212> TYPE: PRT
<213> ORGANISM: Homo sapiens

<400> SEQUENCE: 10

Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Ala Glu
```

```
                    225                 230                 235                 240
Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Asn Gln Gln
        275                 280                 285

Leu Glu Leu His Leu Gly Gly Glu Ser Phe Trp Val Ser Met Ile Ser
        290                 295                 300

Tyr Asn Ser Leu Gly Lys Ser Pro Val Ala Thr Leu Arg Ile Pro Ala
305                 310                 315                 320

Ile Gln Glu Lys

<210> SEQ ID NO 11
<211> LENGTH: 720
<212> TYPE: DNA
<213> ORGANISM: Homo sapiens
<220> FEATURE:
<221> NAME/KEY: CDS
<222> LOCATION: (1)...(720)
<221> NAME/KEY: misc_feature
<222> LOCATION: (1)...(720)
<223> OTHER INFORMATION: soluble IL-31RA "short" form

<400> SEQUENCE: 11 atg atg tgg acc tgg gca ctg tgg atg ctc ccc tca ctc tgc aaa ttc      48
Met Met Trp Thr Trp Ala Leu Trp Met Leu Pro Ser Leu Cys Lys Phe
 1               5                  10                  15 agc ctg gca gct ctg cca gct aag cct gag aac att tcc tgt gtc tac      96
Ser Leu Ala Ala Leu Pro Ala Lys Pro Glu Asn Ile Ser Cys Val Tyr
             20                  25                  30 tac tat agg aaa aat tta acc tgc act tgg agt cca gga aag gaa acc     144
Tyr Tyr Arg Lys Asn Leu Thr Cys Thr Trp Ser Pro Gly Lys Glu Thr
         35                  40                  45 agt tat acc cag tac aca gtt aag aga act tac gct ttt gga gaa aaa     192
Ser Tyr Thr Gln Tyr Thr Val Lys Arg Thr Tyr Ala Phe Gly Glu Lys
     50                  55                  60 cat gat aat tgt aca acc aat agt tct aca agt gaa aat cgt gct tcg     240
His Asp Asn Cys Thr Thr Asn Ser Ser Thr Ser Glu Asn Arg Ala Ser
 65                  70                  75                  80 tgc tct ttt ttc ctt cca aga ata acg atc cca gat aat tat acc att     288
Cys Ser Phe Phe Leu Pro Arg Ile Thr Ile Pro Asp Asn Tyr Thr Ile
                 85                  90                  95 gag gtg gaa gct gaa aat gga gat ggt gta att aaa tct cat atg aca     336
Glu Val Glu Ala Glu Asn Gly Asp Gly Val Ile Lys Ser His Met Thr
            100                 105                 110 tac tgg aga tta gag aac ata gcg aaa act gaa cca cct aag att ttc     384
Tyr Trp Arg Leu Glu Asn Ile Ala Lys Thr Glu Pro Pro Lys Ile Phe
        115                 120                 125 cgt gtg aaa cca gtt ttg ggc atc aaa cga atg att caa att gaa tgg     432
Arg Val Lys Pro Val Leu Gly Ile Lys Arg Met Ile Gln Ile Glu Trp
    130                 135                 140 ata aag cct gag ttg gcg cct gtt tca tct gat tta aaa tac aca ctt     480
Ile Lys Pro Glu Leu Ala Pro Val Ser Ser Asp Leu Lys Tyr Thr Leu
145                 150                 155                 160 cga ttc agg aca gtc aac agt acc agc tgg atg gaa gtc aac ttc gct     528
Arg Phe Arg Thr Val Asn Ser Thr Ser Trp Met Glu Val Asn Phe Ala
                165                 170                 175 aag aac cgt aag gat aaa aac caa acg tac aac ctc acg ggg ctg cag     576
Lys Asn Arg Lys Asp Lys Asn Gln Thr Tyr Asn Leu Thr Gly Leu Gln
            180                 185                 190
```

```
cct ttt aca gaa tat gtc ata gct ctg cga tgt gcg gtc aag gag tca      624
Pro Phe Thr Glu Tyr Val Ile Ala Leu Arg Cys Ala Val Lys Glu Ser
        195                 200                 205 aag ttc tgg agt gac tgg agc caa gaa aaa atg gga atg act gag gaa      672
Lys Phe Trp Ser Asp Trp Ser Gln Glu Lys Met Gly Met Thr Glu Glu
    210                 215                 220 gaa ggc aag cta ctc cct gcg att ccc gtc ctg tct gct ctg gtg tag      720
Glu Gly Lys Leu Leu Pro Ala Ile Pro Val Leu Ser Ala Leu Val  *
225                 230                 235

<210> SEQ ID NO 12
<211> LENGTH: 239
<212> TYPE: PRT
<213> ORGANISM: Homo sapiens

<400> SEQUENCE: 12

Met Met Trp Thr Trp Ala Leu Trp Met Leu Pro Ser Leu Cys Lys Phe
 1               5                  10                  15

Ser Leu Ala Ala Leu Pro Ala Lys Pro Glu Asn Ile Ser Cys Val Tyr
             20                  25                  30

Tyr Tyr Arg Lys Asn Leu Thr Cys Thr Trp Ser Pro Gly Lys Glu Thr
         35                  40                  45

Ser Tyr Thr Gln Tyr Thr Val Lys Arg Thr Tyr Ala Phe Gly Glu Lys
     50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                 85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Gly Lys Leu Leu Pro Ala Ile Pro Val Leu Ser Ala Leu Val
225                 230                 235

<210> SEQ ID NO 13
<211> LENGTH: 1989
<212> TYPE: DNA
<213> ORGANISM: Mus musculus
<220> FEATURE:
<221> NAME/KEY: CDS
<222> LOCATION: (1)...(1989)

<400> SEQUENCE: 13 atg ctg agc agc cag aag gga tcc tgc agc cag gaa cca ggg gca gcc       48
Met Leu Ser Ser Gln Lys Gly Ser Cys Ser Gln Glu Pro Gly Ala Ala
 1               5                  10                  15
```

```
cac gtc cag cct ctg ggt gtg aac gct gga ata atg tgg acc ttg gca       96
His Val Gln Pro Leu Gly Val Asn Ala Gly Ile Met Trp Thr Leu Ala
         20                  25                  30 ctg tgg gca ttc tct ttc ctc tgc aaa ttc agc ctg gca gtc ctg ccg      144
Leu Trp Ala Phe Ser Phe Leu Cys Lys Phe Ser Leu Ala Val Leu Pro
             35                  40                  45 act aag cca gag aac att tcc tgc gtc ttt tac ttc gac aga aat ctg      192
Thr Lys Pro Glu Asn Ile Ser Cys Val Phe Tyr Phe Asp Arg Asn Leu
 50                  55                  60 act tgc act tgg aga cca gag aag gaa acc aat gat acc agc tac att      240
Thr Cys Thr Trp Arg Pro Glu Lys Glu Thr Asn Asp Thr Ser Tyr Ile
 65                  70                  75                  80 gtg act ttg act tac tcc tat gga aaa agc aat tat agt gac aat gct      288
Val Thr Leu Thr Tyr Ser Tyr Gly Lys Ser Asn Tyr Ser Asp Asn Ala
                 85                  90                  95 aca gag gct tca tat tct ttt ccc cgt tcc tgt gca atg ccc cca gac      336
Thr Glu Ala Ser Tyr Ser Phe Pro Arg Ser Cys Ala Met Pro Pro Asp
            100                 105                 110 atc tgc agt gtt gaa gta caa gct caa aat gga gat ggt aaa gtt aaa      384
Ile Cys Ser Val Glu Val Gln Ala Gln Asn Gly Asp Gly Lys Val Lys
        115                 120                 125 tct gac atc aca tat tgg cat tta atc tcc ata gca aaa acc gaa cca      432
Ser Asp Ile Thr Tyr Trp His Leu Ile Ser Ile Ala Lys Thr Glu Pro
130                 135                 140 cct ata att tta agt gtg aat cca att tgt aat aga atg ttc cag ata      480
Pro Ile Ile Leu Ser Val Asn Pro Ile Cys Asn Arg Met Phe Gln Ile
145                 150                 155                 160 caa tgg aaa ccg cgt gaa aag act cgt ggg ttt cct tta gta tgc atg      528
Gln Trp Lys Pro Arg Glu Lys Thr Arg Gly Phe Pro Leu Val Cys Met
                165                 170                 175 ctt cgg ttc aga act gtc aac agt agc cgc tgg acg gaa gtc aat ttt      576
Leu Arg Phe Arg Thr Val Asn Ser Ser Arg Trp Thr Glu Val Asn Phe
            180                 185                 190 gaa aac tgt aaa cag gtc tgc aac ctc aca gga ctt cag gct ttc aca      624
Glu Asn Cys Lys Gln Val Cys Asn Leu Thr Gly Leu Gln Ala Phe Thr
        195                 200                 205 gaa tat gtc ctg gct cta cga ttc agg ttc aat gac tca aga tat tgg      672
Glu Tyr Val Leu Ala Leu Arg Phe Arg Phe Asn Asp Ser Arg Tyr Trp
    210                 215                 220 agc aag tgg agc aaa gaa gaa acc aga gtg act atg gag gaa gtt cca      720
Ser Lys Trp Ser Lys Glu Glu Thr Arg Val Thr Met Glu Glu Val Pro
225                 230                 235                 240 cat gtc ctg gac ctg tgg aga att ctg gaa cca gca gac atg aac gga      768
His Val Leu Asp Leu Trp Arg Ile Leu Glu Pro Ala Asp Met Asn Gly
                245                 250                 255 gac agg aag gtg cga ttg ctg tgg aag aag gca aga gga gcc ccc gtc      816
Asp Arg Lys Val Arg Leu Leu Trp Lys Lys Ala Arg Gly Ala Pro Val
            260                 265                 270 ttg gag aaa aca ttt ggc tac cac ata cag tac ttt gca gag aac agc      864
Leu Glu Lys Thr Phe Gly Tyr His Ile Gln Tyr Phe Ala Glu Asn Ser
        275                 280                 285 act aac ctc aca gag ata aac aac atc acc acc cag cag tat gaa ctg      912
Thr Asn Leu Thr Glu Ile Asn Asn Ile Thr Thr Gln Gln Tyr Glu Leu
    290                 295                 300 ctt ctg atg agc cag gca cac tct gtg tcc gtg act tct ttt aat tct      960
Leu Leu Met Ser Gln Ala His Ser Val Ser Val Thr Ser Phe Asn Ser
305                 310                 315                 320 ctt ggc aag tcc caa gag acc atc ctg agg atc cca gat gtc cat gag     1008
Leu Gly Lys Ser Gln Glu Thr Ile Leu Arg Ile Pro Asp Val His Glu
                325                 330                 335
```

```
aag acc ttc cag tac att aag agc atg cag gcc tac ata gcc gag ccc    1056
Lys Thr Phe Gln Tyr Ile Lys Ser Met Gln Ala Tyr Ile Ala Glu Pro
        340                 345                 350 ctg ttg gtg gtg aac tgg caa agc tcc att cct gcg gtg gac act tgg    1104
Leu Leu Val Val Asn Trp Gln Ser Ser Ile Pro Ala Val Asp Thr Trp
355                 360                 365 ata gtg gag tgg ctc cca gaa gct gcc atg tcg aag ttc cct gcc ctt    1152
Ile Val Glu Trp Leu Pro Glu Ala Ala Met Ser Lys Phe Pro Ala Leu
    370                 375                 380 tcc tgg gaa tct gtg tct cag gtc acg aac tgg acc atc gag caa gat    1200
Ser Trp Glu Ser Val Ser Gln Val Thr Asn Trp Thr Ile Glu Gln Asp
385                 390                 395                 400 aaa cta aaa cct ttc aca tgc tat aat ata tca gtg tat cca gtg ttg    1248
Lys Leu Lys Pro Phe Thr Cys Tyr Asn Ile Ser Val Tyr Pro Val Leu
                405                 410                 415 gga cac cga gtt gga gag ccg tat tca atc caa gct tat gcc aaa gaa    1296
Gly His Arg Val Gly Glu Pro Tyr Ser Ile Gln Ala Tyr Ala Lys Glu
            420                 425                 430 gga act cca tta aaa ggt cct gag acc agg gtg gag aac atc ggt ctg    1344
Gly Thr Pro Leu Lys Gly Pro Glu Thr Arg Val Glu Asn Ile Gly Leu
        435                 440                 445 agg aca gcc acg atc aca tgg aag gag att cct aag agt gct agg aat    1392
Arg Thr Ala Thr Ile Thr Trp Lys Glu Ile Pro Lys Ser Ala Arg Asn
450                 455                 460 gga ttt atc aac aat tac act gta ttt tac caa gct gaa ggt gga aaa    1440
Gly Phe Ile Asn Asn Tyr Thr Val Phe Tyr Gln Ala Glu Gly Gly Lys
465                 470                 475                 480 gaa ctc tcc aag act gtt aac tct cat gcc ctg cag tgt gac ctg gag    1488
Glu Leu Ser Lys Thr Val Asn Ser His Ala Leu Gln Cys Asp Leu Glu
                485                 490                 495 tct ctg aca cga agg acc tct tat act gtt tgg gtc atg gcc agc acc    1536
Ser Leu Thr Arg Arg Thr Ser Tyr Thr Val Trp Val Met Ala Ser Thr
            500                 505                 510 aga gct gga ggt acc aac ggg gtg aga ata aac ttc aag aca ttg tca    1584
Arg Ala Gly Gly Thr Asn Gly Val Arg Ile Asn Phe Lys Thr Leu Ser
        515                 520                 525 atc agt gtg ttt gaa att gtc ctt cta aca tct cta gtt gga gga ggc    1632
Ile Ser Val Phe Glu Ile Val Leu Leu Thr Ser Leu Val Gly Gly Gly
530                 535                 540 ctt ctt cta ctt agc atc aaa aca gtg act ttt ggc ctc aga aag cca    1680
Leu Leu Leu Leu Ser Ile Lys Thr Val Thr Phe Gly Leu Arg Lys Pro
545                 550                 555                 560 aac cgg ttg act ccc ctg tgt tgt cct gat gtt ccc aac cct gct gaa    1728
Asn Arg Leu Thr Pro Leu Cys Cys Pro Asp Val Pro Asn Pro Ala Glu
                565                 570                 575 agt agt tta gcc aca tgg ctc gga gat ggt ttc aag aag tca aat atg    1776
Ser Ser Leu Ala Thr Trp Leu Gly Asp Gly Phe Lys Lys Ser Asn Met
            580                 585                 590 aag gag act gga aac tct ggg aac aca gaa gac gtg gtc cta aaa cca    1824
Lys Glu Thr Gly Asn Ser Gly Asn Thr Glu Asp Val Val Leu Lys Pro
        595                 600                 605 tgt ccc gtc ccc gcg gat ctc att gac aag ctg gta gtg aac ttt gag    1872
Cys Pro Val Pro Ala Asp Leu Ile Asp Lys Leu Val Val Asn Phe Glu
610                 615                 620 aat ttt ctg gaa gta gtt ttg aca gag gaa gct gga aag ggt cag gcg    1920
Asn Phe Leu Glu Val Val Leu Thr Glu Glu Ala Gly Lys Gly Gln Ala
625                 630                 635                 640 agc att ttg gga gga gaa gcg aat gag tat atc tta tcc cag gaa cca    1968
Ser Ile Leu Gly Gly Glu Ala Asn Glu Tyr Ile Leu Ser Gln Glu Pro
                645                 650                 655
```

```
agc tgt cct ggc cat tgc tga                                    1989
Ser Cys Pro Gly His Cys *
            660
```

<210> SEQ ID NO 14
<211> LENGTH: 662
<212> TYPE: PRT
<213> ORGANISM: Mus musculus

<400> SEQUENCE: 14

```
Met Leu Ser Ser Gln Lys Gly Ser Cys Ser Gln Glu Pro Gly Ala Ala
 1               5                  10                  15

His Val Gln Pro Leu Gly Val Asn Ala Gly Ile Met Trp Thr Leu Ala
                20                  25                  30

Leu Trp Ala Phe Ser Phe Leu Cys Lys Phe Ser Leu Ala Val Leu Pro
            35                  40                  45

Thr Lys Pro Glu Asn Ile Ser Cys Val Phe Tyr Phe Asp Arg Asn Leu
        50                  55                  60

Thr Cys Thr Trp Arg Pro Glu Lys Glu Thr Asn Asp Thr Ser Tyr Ile
 65                  70                  75                  80

Val Thr Leu Thr Tyr Ser Tyr Gly Lys Ser Asn Tyr Ser Asp Asn Ala
                85                  90                  95

Thr Glu Ala Ser Tyr Ser Phe Pro Arg Ser Cys Ala Met Pro Pro Asp
            100                 105                 110

Ile Cys Ser Val Glu Val Gln Ala Gln Asn Gly Asp Gly Lys Val Lys
        115                 120                 125

Ser Asp Ile Thr Tyr Trp His Leu Ile Ser Ile Ala Lys Thr Glu Pro
    130                 135                 140

Pro Ile Ile Leu Ser Val Asn Pro Ile Cys Asn Arg Met Phe Gln Ile
145                 150                 155                 160

Gln Trp Lys Pro Arg Glu Lys Thr Arg Gly Phe Pro Leu Val Cys Met
                165                 170                 175

Leu Arg Phe Arg Thr Val Asn Ser Ser Arg Trp Thr Glu Val Asn Phe
            180                 185                 190

Glu Asn Cys Lys Gln Val Cys Asn Leu Thr Gly Leu Gln Ala Phe Thr
        195                 200                 205

Glu Tyr Val Leu Ala Leu Arg Phe Arg Phe Asn Asp Ser Arg Tyr Trp
    210                 215                 220

Ser Lys Trp Ser Lys Glu Glu Thr Arg Val Thr Met Glu Glu Val Pro
225                 230                 235                 240

His Val Leu Asp Leu Trp Arg Ile Leu Glu Pro Ala Asp Met Asn Gly
                245                 250                 255

Asp Arg Lys Val Arg Leu Leu Trp Lys Lys Ala Arg Gly Ala Pro Val
            260                 265                 270

Leu Glu Lys Thr Phe Gly Tyr His Ile Gln Tyr Phe Ala Glu Asn Ser
        275                 280                 285

Thr Asn Leu Thr Glu Ile Asn Asn Ile Thr Thr Gln Gln Tyr Glu Leu
    290                 295                 300

Leu Leu Met Ser Gln Ala His Ser Val Ser Val Thr Ser Phe Asn Ser
305                 310                 315                 320

Leu Gly Lys Ser Gln Glu Thr Ile Leu Arg Ile Pro Asp Val His Glu
                325                 330                 335

Lys Thr Phe Gln Tyr Ile Lys Ser Met Gln Ala Tyr Ile Ala Glu Pro
            340                 345                 350

Leu Leu Val Val Asn Trp Gln Ser Ser Ile Pro Ala Val Asp Thr Trp
```

```
                355                 360                 365
Ile Val Glu Trp Leu Pro Glu Ala Ala Met Ser Lys Phe Pro Ala Leu
370                 375                 380

Ser Trp Glu Ser Val Ser Gln Val Thr Asn Trp Thr Ile Glu Gln Asp
385                 390                 395                 400

Lys Leu Lys Pro Phe Thr Cys Tyr Asn Ile Ser Val Tyr Pro Val Leu
                405                 410                 415

Gly His Arg Val Gly Glu Pro Tyr Ser Ile Gln Ala Tyr Ala Lys Glu
            420                 425                 430

Gly Thr Pro Leu Lys Gly Pro Glu Thr Arg Val Glu Asn Ile Gly Leu
        435                 440                 445

Arg Thr Ala Thr Ile Thr Trp Lys Glu Ile Pro Lys Ser Ala Arg Asn
    450                 455                 460

Gly Phe Ile Asn Asn Tyr Thr Val Phe Tyr Gln Ala Glu Gly Gly Lys
465                 470                 475                 480

Glu Leu Ser Lys Thr Val Asn Ser His Ala Leu Gln Cys Asp Leu Glu
                485                 490                 495

Ser Leu Thr Arg Arg Thr Ser Tyr Thr Val Trp Val Met Ala Ser Thr
            500                 505                 510

Arg Ala Gly Gly Thr Asn Gly Val Arg Ile Asn Phe Lys Thr Leu Ser
        515                 520                 525

Ile Ser Val Phe Glu Ile Val Leu Leu Thr Ser Leu Val Gly Gly Gly
    530                 535                 540

Leu Leu Leu Leu Ser Ile Lys Thr Val Thr Phe Gly Leu Arg Lys Pro
545                 550                 555                 560

Asn Arg Leu Thr Pro Leu Cys Cys Pro Asp Val Pro Asn Pro Ala Glu
                565                 570                 575

Ser Ser Leu Ala Thr Trp Leu Gly Asp Gly Phe Lys Lys Ser Asn Met
            580                 585                 590

Lys Glu Thr Gly Asn Ser Gly Asn Thr Glu Asp Val Val Leu Lys Pro
        595                 600                 605

Cys Pro Val Pro Ala Asp Leu Ile Asp Lys Leu Val Val Asn Phe Glu
    610                 615                 620

Asn Phe Leu Glu Val Val Leu Thr Glu Glu Ala Gly Lys Gly Gln Ala
625                 630                 635                 640

Ser Ile Leu Gly Gly Glu Ala Asn Glu Tyr Ile Leu Ser Gln Glu Pro
                645                 650                 655

Ser Cys Pro Gly His Cys
            660

<210> SEQ ID NO 15
<211> LENGTH: 2940
<212> TYPE: DNA
<213> ORGANISM: Homo sapiens
<220> FEATURE:
<221> NAME/KEY: CDS
<222> LOCATION: (1)...(2940)

<400> SEQUENCE: 15 atg gct cta ttt gca gtc ttt cag aca aca ttc ttc tta aca ttg ctg    48
Met Ala Leu Phe Ala Val Phe Gln Thr Thr Phe Phe Leu Thr Leu Leu
 1               5                  10                  15 tcc ttg agg act tac cag agt gaa gtc ttg gct gaa cgt tta cca ttg    96
Ser Leu Arg Thr Tyr Gln Ser Glu Val Leu Ala Glu Arg Leu Pro Leu
             20                  25                  30 act cct gta tca ctt aaa gtt tcc acc aat tct acg cgt cag agt ttg   144
Thr Pro Val Ser Leu Lys Val Ser Thr Asn Ser Thr Arg Gln Ser Leu
```

-continued

```
             35                  40                  45
cac tta caa tgg act gtc cac aac ctt cct tat cat cag gaa ttg aaa       192
His Leu Gln Trp Thr Val His Asn Leu Pro Tyr His Gln Glu Leu Lys
 50                  55                  60 atg gta ttt cag atc cag atc agt agg att gaa aca tcc aat gtc atc       240
Met Val Phe Gln Ile Gln Ile Ser Arg Ile Glu Thr Ser Asn Val Ile
 65                  70                  75                  80 tgg gtg ggg aat tac agc acc act gtg aag tgg aac cag gtt ctg cat       288
Trp Val Gly Asn Tyr Ser Thr Thr Val Lys Trp Asn Gln Val Leu His
                     85                  90                  95 tgg agc tgg gaa tct gag ctc cct ttg gaa tgt gcc aca cac ttt gta       336
Trp Ser Trp Glu Ser Glu Leu Pro Leu Glu Cys Ala Thr His Phe Val
                 100                 105                 110 aga ata aag agt ttg gtg gac gat gcc aag ttc cct gag cca aat ttc       384
Arg Ile Lys Ser Leu Val Asp Asp Ala Lys Phe Pro Glu Pro Asn Phe
             115                 120                 125 tgg agc aac tgg agt tcc tgg gag gaa gtc agt gta caa gat tct act       432
Trp Ser Asn Trp Ser Ser Trp Glu Glu Val Ser Val Gln Asp Ser Thr
 130                 135                 140 gga cag gat ata ttg ttc gtt ttc cct aaa gat aag ctg gtg gaa gaa       480
Gly Gln Asp Ile Leu Phe Val Phe Pro Lys Asp Lys Leu Val Glu Glu
145                 150                 155                 160 ggc acc aat gtt acc att tgt tac gtt tct agg aac att caa aat aat       528
Gly Thr Asn Val Thr Ile Cys Tyr Val Ser Arg Asn Ile Gln Asn Asn
                 165                 170                 175 gta tcc tgt tat ttg gaa ggg aaa cag att cat gga gaa caa ctt gat       576
Val Ser Cys Tyr Leu Glu Gly Lys Gln Ile His Gly Glu Gln Leu Asp
             180                 185                 190 cca cat gta act gca ttc aac ttg aat agt gtg cct ttc att agg aat       624
Pro His Val Thr Ala Phe Asn Leu Asn Ser Val Pro Phe Ile Arg Asn
         195                 200                 205 aaa ggg aca aat atc tat tgt gag gca agt caa gga aat gtc agt gaa       672
Lys Gly Thr Asn Ile Tyr Cys Glu Ala Ser Gln Gly Asn Val Ser Glu
 210                 215                 220 ggc atg aaa ggc atc gtt ctt ttt gtc tca aaa gta ctt gag gag ccc       720
Gly Met Lys Gly Ile Val Leu Phe Val Ser Lys Val Leu Glu Glu Pro
225                 230                 235                 240 aag gac ttt tct tgt gaa acc gag gac ttc aag act ttg cac tgt act       768
Lys Asp Phe Ser Cys Glu Thr Glu Asp Phe Lys Thr Leu His Cys Thr
                 245                 250                 255 tgg gat cct ggg acg gac act gcc ttg ggg tgg tct aaa caa cct tcc       816
Trp Asp Pro Gly Thr Asp Thr Ala Leu Gly Trp Ser Lys Gln Pro Ser
             260                 265                 270 caa agc tac act tta ttt gaa tca ttt tct ggg gaa aag aaa ctt tgt       864
Gln Ser Tyr Thr Leu Phe Glu Ser Phe Ser Gly Glu Lys Lys Leu Cys
         275                 280                 285 aca cac aaa aac tgg tgt aat tgg caa ata act caa gac tca caa gaa       912
Thr His Lys Asn Trp Cys Asn Trp Gln Ile Thr Gln Asp Ser Gln Glu
 290                 295                 300 acc tat aac ttc aca ctc ata gct gaa aat tac tta agg aag aga agt       960
Thr Tyr Asn Phe Thr Leu Ile Ala Glu Asn Tyr Leu Arg Lys Arg Ser
305                 310                 315                 320 gtc aat atc ctt ttt aac ctg act cat cga gtt tat tta atg aat cct      1008
Val Asn Ile Leu Phe Asn Leu Thr His Arg Val Tyr Leu Met Asn Pro
                 325                 330                 335 ttt agt gtc aac ttt gaa aat gta aat gca aca aat gcc atc atg acc      1056
Phe Ser Val Asn Phe Glu Asn Val Asn Ala Thr Asn Ala Ile Met Thr
             340                 345                 350 tgg aag gtg cac tcc ata agg aat aat ttc aca tat ttg tgt cag att      1104
Trp Lys Val His Ser Ile Arg Asn Asn Phe Thr Tyr Leu Cys Gln Ile
```

```
                    355                 360                 365
gaa ctc cat ggt gaa gga aaa atg atg caa tac aat gtt tcc atc aag        1152
Glu Leu His Gly Glu Gly Lys Met Met Gln Tyr Asn Val Ser Ile Lys
370                 375                 380 gtg aac ggt gag tac ttc tta agt gaa ctg gaa cct gcc aca gag tac        1200
Val Asn Gly Glu Tyr Phe Leu Ser Glu Leu Glu Pro Ala Thr Glu Tyr
385                 390                 395                 400 atg gcg cga gta cgg tgt gct gat gcc agc cac ttc tgg aaa tgg agt        1248
Met Ala Arg Val Arg Cys Ala Asp Ala Ser His Phe Trp Lys Trp Ser
                405                 410                 415 gaa tgg agt ggt cag aac ttc acc aca ctt gaa gct gct ccc tca gag        1296
Glu Trp Ser Gly Gln Asn Phe Thr Thr Leu Glu Ala Ala Pro Ser Glu
            420                 425                 430 gcc cct gat gtc tgg aga att gtg agc ttg gag cca gga aat cat act        1344
Ala Pro Asp Val Trp Arg Ile Val Ser Leu Glu Pro Gly Asn His Thr
        435                 440                 445 gtg acc tta ttc tgg aag cca tta tca aaa ctg cat gcc aat gga agg        1392
Val Thr Leu Phe Trp Lys Pro Leu Ser Lys Leu His Ala Asn Gly Lys
450                 455                 460 atc ctg ttc tat aat gta gtt gta gaa aac cta gac aaa cca tcc agt        1440
Ile Leu Phe Tyr Asn Val Val Val Glu Asn Leu Asp Lys Pro Ser Ser
465                 470                 475                 480 tca gag ctc cat tcc att cca gca cca gcc aac agc aca aaa cta atc        1488
Ser Glu Leu His Ser Ile Pro Ala Pro Ala Asn Ser Thr Lys Leu Ile
                485                 490                 495 ctt gac agg tgt tcc tac caa atc tgc gtc ata gcc aac aac agt gtg        1536
Leu Asp Arg Cys Ser Tyr Gln Ile Cys Val Ile Ala Asn Asn Ser Val
            500                 505                 510 ggt gct tct cct gct tct gta ata gtc atc tct gca gac ccc gaa aac        1584
Gly Ala Ser Pro Ala Ser Val Ile Val Ile Ser Ala Asp Pro Glu Asn
        515                 520                 525 aaa gag gtt gag gaa gaa aga att gca ggc aca gag ggt gga ttc tct        1632
Lys Glu Val Glu Glu Glu Arg Ile Ala Gly Thr Glu Gly Gly Phe Ser
530                 535                 540 ctg tct tgg aaa ccc caa cct gga gat gtt ata ggc tat gtt gtg gac        1680
Leu Ser Trp Lys Pro Gln Pro Gly Asp Val Ile Gly Tyr Val Val Asp
545                 550                 555                 560 tgg tgt gac cat acc cag gat gtg ctc ggt gat ttc cag tgg aag aat        1728
Trp Cys Asp His Thr Gln Asp Val Leu Gly Asp Phe Gln Trp Lys Asn
                565                 570                 575 gta ggt ccc aat acc aca agc aca gtc att agc aca gat gct ttt agg        1776
Val Gly Pro Asn Thr Thr Ser Thr Val Ile Ser Thr Asp Ala Phe Arg
            580                 585                 590 cca gga gtt cga tat gac ttc aga att tat ggg tta tct aca aaa agg        1824
Pro Gly Val Arg Tyr Asp Phe Arg Ile Tyr Gly Leu Ser Thr Lys Arg
        595                 600                 605 att gct tgt tta tta gag aaa aaa aca gga tac tct cag gaa ctt gct        1872
Ile Ala Cys Leu Leu Glu Lys Lys Thr Gly Tyr Ser Gln Glu Leu Ala
610                 615                 620 cct tca gac aac cct cac gtg ctg gtg gat aca ttg aca tcc cac tcc        1920
Pro Ser Asp Asn Pro His Val Leu Val Asp Thr Leu Thr Ser His Ser
625                 630                 635                 640 ttc act ctg agt tgg aaa gat tac tct act gaa tct caa cct ggt ttt        1968
Phe Thr Leu Ser Trp Lys Asp Tyr Ser Thr Glu Ser Gln Pro Gly Phe
                645                 650                 655 ata caa ggg tac cat gtc tat ctg aaa tcc aag gcg agg cag tgc cac        2016
Ile Gln Gly Tyr His Val Tyr Leu Lys Ser Lys Ala Arg Gln Cys His
            660                 665                 670 cca cga ttt gaa aag gca gtt ctt tca gat ggt tca gaa tgt tgc aaa        2064
Pro Arg Phe Glu Lys Ala Val Leu Ser Asp Gly Ser Glu Cys Cys Lys
```

```
                    675                 680                 685
tac aaa att gac aac ccg gaa gaa aag gca ttg att gtg gac aac cta    2112
Tyr Lys Ile Asp Asn Pro Glu Glu Lys Ala Leu Ile Val Asp Asn Leu
690                 695                 700 aag cca gaa tcc ttc tat gag ttt ttc atc act cca ttc act agt gct    2160
Lys Pro Glu Ser Phe Tyr Glu Phe Phe Ile Thr Pro Phe Thr Ser Ala
705                 710                 715                 720 ggt gaa ggc ccc agt gct acg ttc acg aag gtc acg act ccg gat gaa    2208
Gly Glu Gly Pro Ser Ala Thr Phe Thr Lys Val Thr Thr Pro Asp Glu
                725                 730                 735 cac tcc tcg atg ctg att cat atc cta ctg ccc atg gtt ttc tgc gtc    2256
His Ser Ser Met Leu Ile His Ile Leu Leu Pro Met Val Phe Cys Val
            740                 745                 750 ttg ctc atc atg gtc atg tgc tac ttg aaa agt cag tgg atc aag gag    2304
Leu Leu Ile Met Val Met Cys Tyr Leu Lys Ser Gln Trp Ile Lys Glu
        755                 760                 765 acc tgt tat cct gac atc cct gac cct tac aag agc agc atc ctg tca    2352
Thr Cys Tyr Pro Asp Ile Pro Asp Pro Tyr Lys Ser Ser Ile Leu Ser
770                 775                 780 tta ata aaa ttc aag gag aac cct cac cta ata ata atg aat gtc agt    2400
Leu Ile Lys Phe Lys Glu Asn Pro His Leu Ile Ile Met Asn Val Ser
785                 790                 795                 800 gac tgt atc cca gat gct att gaa gtt gta agc aag cca gaa ggg aca    2448
Asp Cys Ile Pro Asp Ala Ile Glu Val Val Ser Lys Pro Glu Gly Thr
                805                 810                 815 aag ata cag ttc cta ggc act agg aag tca ctc aca gaa acc gag ttg    2496
Lys Ile Gln Phe Leu Gly Thr Arg Lys Ser Leu Thr Glu Thr Glu Leu
            820                 825                 830 act aag cct aac tac ctt tat ctc ctt cca aca gaa aag aat cac tct    2544
Thr Lys Pro Asn Tyr Leu Tyr Leu Leu Pro Thr Glu Lys Asn His Ser
        835                 840                 845 ggc cct ggc ccc tgc atc tgt ttt gag aac ttg acc tat aac cag gca    2592
Gly Pro Gly Pro Cys Ile Cys Phe Glu Asn Leu Thr Tyr Asn Gln Ala
850                 855                 860 gct tct gac tct ggc tct tgt ggc cat gtt cca gta tcc cca aaa gcc    2640
Ala Ser Asp Ser Gly Ser Cys Gly His Val Pro Val Ser Pro Lys Ala
865                 870                 875                 880 cca agt atg ctg gga cta atg acc tca cct gaa aat gta cta aag gca    2688
Pro Ser Met Leu Gly Leu Met Thr Ser Pro Glu Asn Val Leu Lys Ala
                885                 890                 895 cta gaa aaa aac tac atg aac tcc ctg gga gaa atc cca gct gga gaa    2736
Leu Glu Lys Asn Tyr Met Asn Ser Leu Gly Glu Ile Pro Ala Gly Glu
            900                 905                 910 aca agt ttg aat tat gtg tcc cag ttg gct tca ccc atg ttt gga gac    2784
Thr Ser Leu Asn Tyr Val Ser Gln Leu Ala Ser Pro Met Phe Gly Asp
        915                 920                 925 aag gac agt ctc cca aca aac cca gta gag gca cca cac tgt tca gag    2832
Lys Asp Ser Leu Pro Thr Asn Pro Val Glu Ala Pro His Cys Ser Glu
930                 935                 940 tat aaa atg caa atg gca gtc tcc ctg cgt ctt gcc ttg cct ccc ccg    2880
Tyr Lys Met Gln Met Ala Val Ser Leu Arg Leu Ala Leu Pro Pro Pro
945                 950                 955                 960 acc gag aat agc agc ctc tcc tca att acc ctt tta gat cca ggt gaa    2928
Thr Glu Asn Ser Ser Leu Ser Ser Ile Thr Leu Leu Asp Pro Gly Glu
                965                 970                 975 cac tac tgc taa                                                    2940
His Tyr Cys *

<210> SEQ ID NO 16
<211> LENGTH: 979
```

<212> TYPE: PRT
<213> ORGANISM: Homo sapiens

<400> SEQUENCE: 16

```
Met Ala Leu Phe Ala Val Phe Gln Thr Thr Phe Phe Leu Thr Leu Leu
1               5                   10                  15

Ser Leu Arg Thr Tyr Gln Ser Glu Val Leu Ala Glu Arg Leu Pro Leu
            20                  25                  30

Thr Pro Val Ser Leu Lys Val Ser Thr Asn Ser Thr Arg Gln Ser Leu
        35                  40                  45

His Leu Gln Trp Thr Val His Asn Leu Pro Tyr His Gln Glu Leu Lys
    50                  55                  60

Met Val Phe Gln Ile Gln Ile Ser Arg Ile Glu Thr Ser Asn Val Ile
65                  70                  75                  80

Trp Val Gly Asn Tyr Ser Thr Thr Val Lys Trp Asn Gln Val Leu His
                85                  90                  95

Trp Ser Trp Glu Ser Glu Leu Pro Leu Glu Cys Ala Thr His Phe Val
            100                 105                 110

Arg Ile Lys Ser Leu Val Asp Asp Ala Lys Phe Pro Glu Pro Asn Phe
        115                 120                 125

Trp Ser Asn Trp Ser Ser Trp Glu Glu Val Ser Val Gln Asp Ser Thr
    130                 135                 140

Gly Gln Asp Ile Leu Phe Val Phe Pro Lys Asp Lys Leu Val Glu Glu
145                 150                 155                 160

Gly Thr Asn Val Thr Ile Cys Tyr Val Ser Arg Asn Ile Gln Asn Asn
                165                 170                 175

Val Ser Cys Tyr Leu Glu Gly Lys Gln Ile His Gly Glu Gln Leu Asp
            180                 185                 190

Pro His Val Thr Ala Phe Asn Leu Asn Ser Val Pro Phe Ile Arg Asn
        195                 200                 205

Lys Gly Thr Asn Ile Tyr Cys Glu Ala Ser Gln Gly Asn Val Ser Glu
    210                 215                 220

Gly Met Lys Gly Ile Val Leu Phe Val Ser Lys Val Leu Glu Glu Pro
225                 230                 235                 240

Lys Asp Phe Ser Cys Glu Thr Glu Asp Phe Lys Thr Leu His Cys Thr
                245                 250                 255

Trp Asp Pro Gly Thr Asp Thr Ala Leu Gly Trp Ser Lys Gln Pro Ser
            260                 265                 270

Gln Ser Tyr Thr Leu Phe Glu Ser Phe Ser Gly Glu Lys Lys Leu Cys
        275                 280                 285

Thr His Lys Asn Trp Cys Asn Trp Gln Ile Thr Gln Asp Ser Gln Glu
    290                 295                 300

Thr Tyr Asn Phe Thr Leu Ile Ala Glu Asn Tyr Leu Arg Lys Arg Ser
305                 310                 315                 320

Val Asn Ile Leu Phe Asn Leu Thr His Arg Val Tyr Leu Met Asn Pro
                325                 330                 335

Phe Ser Val Asn Phe Glu Asn Val Asn Ala Thr Asn Ala Ile Met Thr
            340                 345                 350

Trp Lys Val His Ser Ile Arg Asn Asn Phe Thr Tyr Leu Cys Gln Ile
        355                 360                 365

Glu Leu His Gly Glu Gly Lys Met Met Gln Tyr Asn Val Ser Ile Lys
    370                 375                 380

Val Asn Gly Glu Tyr Phe Leu Ser Glu Leu Glu Pro Ala Thr Glu Tyr
385                 390                 395                 400
```

-continued

```
Met Ala Arg Val Arg Cys Ala Asp Ala Ser His Phe Trp Lys Trp Ser
                405                 410                 415
Glu Trp Ser Gly Gln Asn Phe Thr Thr Leu Gly Ala Ala Pro Ser Glu
            420                 425                 430
Ala Pro Asp Val Trp Arg Ile Val Ser Leu Glu Pro Gly Asn His Thr
        435                 440                 445
Val Thr Leu Phe Trp Lys Pro Leu Ser Lys Leu His Ala Asn Gly Lys
    450                 455                 460
Ile Leu Phe Tyr Asn Val Val Glu Asn Leu Asp Lys Pro Ser Ser
465                 470                 475                 480
Ser Glu Leu His Ser Ile Pro Ala Pro Asn Ser Thr Lys Leu Ile
                485                 490                 495
Leu Asp Arg Cys Ser Tyr Gln Ile Cys Val Ile Ala Asn Asn Ser Val
            500                 505                 510
Gly Ala Ser Pro Ala Ser Val Ile Val Ile Ser Ala Asp Pro Glu Asn
        515                 520                 525
Lys Glu Val Glu Glu Arg Ile Ala Gly Thr Gly Gly Phe Ser
    530                 535                 540
Leu Ser Trp Lys Pro Gln Pro Gly Asp Val Ile Gly Tyr Val Val Asp
545                 550                 555                 560
Trp Cys Asp His Thr Gln Asp Val Leu Gly Asp Phe Gln Trp Lys Asn
                565                 570                 575
Val Gly Pro Asn Thr Thr Ser Thr Val Ile Ser Thr Asp Ala Phe Arg
            580                 585                 590
Pro Gly Val Arg Tyr Asp Phe Arg Ile Tyr Gly Leu Ser Thr Lys Arg
        595                 600                 605
Ile Ala Cys Leu Leu Glu Lys Lys Thr Gly Tyr Ser Gln Glu Leu Ala
610                 615                 620
Pro Ser Asp Asn Pro His Val Leu Val Asp Thr Leu Thr Ser His Ser
625                 630                 635                 640
Phe Thr Leu Ser Trp Lys Asp Tyr Ser Thr Glu Ser Gln Pro Gly Phe
                645                 650                 655
Ile Gln Gly Tyr His Val Tyr Leu Lys Ser Lys Ala Arg Gln Cys His
            660                 665                 670
Pro Arg Phe Glu Lys Ala Val Leu Ser Asp Gly Ser Glu Cys Cys Lys
        675                 680                 685
Tyr Lys Ile Asp Asn Pro Glu Glu Lys Ala Leu Ile Val Asp Asn Leu
    690                 695                 700
Lys Pro Glu Ser Phe Tyr Glu Phe Phe Ile Thr Pro Phe Thr Ser Ala
705                 710                 715                 720
Gly Glu Gly Pro Ser Ala Thr Phe Thr Lys Val Thr Thr Pro Asp Glu
                725                 730                 735
His Ser Ser Met Leu Ile His Ile Leu Leu Pro Met Val Phe Cys Val
            740                 745                 750
Leu Leu Ile Met Val Met Cys Tyr Leu Lys Ser Gln Trp Ile Lys Glu
        755                 760                 765
Thr Cys Tyr Pro Asp Ile Pro Asp Pro Tyr Lys Ser Ser Ile Leu Ser
    770                 775                 780
Leu Ile Lys Phe Lys Glu Asn Pro His Leu Ile Ile Met Asn Val Ser
785                 790                 795                 800
Asp Cys Ile Pro Asp Ala Ile Glu Val Val Ser Lys Pro Glu Gly Thr
                805                 810                 815
Lys Ile Gln Phe Leu Gly Thr Arg Lys Ser Leu Thr Glu Thr Glu Leu
            820                 825                 830
```

-continued

```
Thr Lys Pro Asn Tyr Leu Tyr Leu Leu Pro Thr Glu Lys Asn His Ser
        835                 840                 845

Gly Pro Gly Pro Cys Ile Cys Phe Glu Asn Leu Thr Tyr Asn Gln Ala
        850                 855                 860

Ala Ser Asp Ser Gly Ser Cys Gly His Val Pro Val Ser Pro Lys Ala
865                 870                 875                 880

Pro Ser Met Leu Gly Leu Met Thr Ser Pro Glu Asn Val Leu Lys Ala
                885                 890                 895

Leu Glu Lys Asn Tyr Met Asn Ser Leu Gly Glu Ile Pro Ala Gly Glu
                900                 905                 910

Thr Ser Leu Asn Tyr Val Ser Gln Leu Ala Ser Pro Met Phe Gly Asp
        915                 920                 925

Lys Asp Ser Leu Pro Thr Asn Pro Val Glu Ala Pro His Cys Ser Glu
        930                 935                 940

Tyr Lys Met Gln Met Ala Val Ser Leu Arg Leu Ala Leu Pro Pro Pro
945                 950                 955                 960

Thr Glu Asn Ser Ser Leu Ser Ser Ile Thr Leu Leu Asp Pro Gly Glu
                965                 970                 975

His Tyr Cys
```

METHODS OF DETERMINING DOSE OF IL-31 AGONIST TO TREAT PULMONARY INFLAMMATION

CROSS-REFERENCE TO RELATED APPLICATIONS

This application is a divisional of U.S. application Ser. No. 11/972,596, filed Jan. 10, 2008 now U.S. Pat. No. 7,799,323, which claims the benefit of U.S. Provisional Application Ser. No. 60/884,379, filed Jan. 10, 2007, both of which are herein incorporated by reference.

BACKGROUND OF THE INVENTION

Asthma is a chronic lung disease that affects more than 17 million Americans. Asthma is characterized by inflammation of the airways with intermittent bronchospasm, which is caused by the inflammation of the muscles surrounding the air passageways. Breathing may be so labored that an asthma attack becomes life-threatening. Asthma is a chronic disease and it requires continuous management and appropriate treatment.

Symptoms of asthma include cough, chest tightness, shortness of breath, and wheezing. Asthma can be triggered by a variety of irritations, such as allergens, tobacco smoke, strong odors, respiratory infections, weather changes, viral or sinus infections, exercise, stress, reflux disease (Stomach acid flowing back up the esophagus, or food pipe), medications, foods, and emotional anxiety.

Different classifications of asthma include: allergic asthma, caused by airway inflammation when exposed to allergens; exercised-induced asthma, where the airways narrow when triggered by vigorous activity; cough-variant asthma, a chronic, persistent cough without shortness of breath; and occupational asthma, which is related to working in a particular occupational environment.

Management of asthma involves several approaches, including preventing chronic and troublesome symptoms; maintaining "normal" breathing; maintain normal activity levels, including exercise; preventing recurrent asthma flare-ups, and minimize the need for emergency room visits or hospitalizations, and providing optimal medication therapy with no or minimal adverse effects. Asthma management includes using proper medications, or combinations of medications to prevent and control asthma symptoms and to reduce airway inflammation. Asthma medications are thus categorized into two general classes, quick-relief and long-term control medications. Quick-relief medications that are used to provide temporary relief of symptoms include bronchodilators, such as beta-agonists and anticholinergics, and corticosteroids. Long-term control medications are taken daily to control the airway inflammation in persistent asthma. This class includes inhaled corticosteroids to inhibit or prevent inflammation.

Thus, there is a need for additional treatment options in managing asthma and airway hyper-responsiveness. The present invention provides the use of a cytokine to aid in management of this disease.

DESCRIPTION OF THE INVENTION

Figure 1:
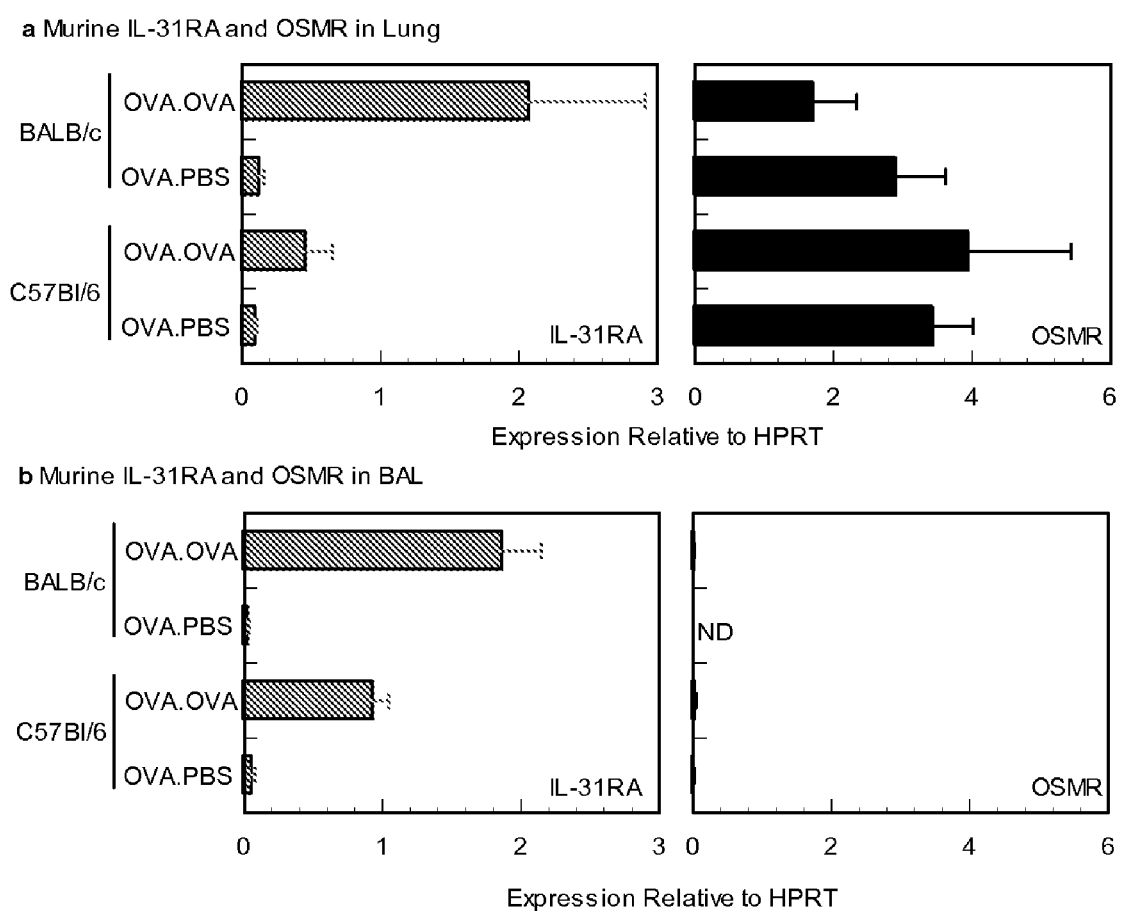
FIG. 1a shows quantitative RT-PCR analysis of IL-31RA and OSMR levels in lung tissue following sensitization with OVA and challenge with either OVA or PBS in BALB/c or C57B1/6 mice.
FIG. 1b shows quantitative RT-PCR analysis of IL-31RA and OSMR levels in cells from bronchial alveolar lavage fluid (BAL) following sensitization with OVA and challenge with either OVA or PBS in BALB/c or C57B1/6 mice.

The present invention is based in part upon the discovery that mice in a model of airway hyper-responsiveness (AHR) that were treated with IL-31 indicated exhibited less AHR compared to vehicle treated controls and that IL-31 treatment decreases disease pathogenesis in a murine model of allergic asthma, possibly through the down-regulation of IL-5 and IL-13. In addition, the invention teaches the unexpected findings that timing of the administration of IL-31 and dosage are important in using IL-31 to treat asthma and AHR. Thus the present invention encompasses the use of IL-31 to treat asthma, acute respiratory distress, chronic obstructive pulmonary disease, allergic rhinitis, and respiratory diseases.

IL-31 is the HUGO name for a cytokine that has been previously described as Zcyto17rlig in a published U.S. patent application (See published U.S. patent application number 20030224487, U.S. patent application Ser. No. 10/352,554, filed Jan. 21, 2003, now issued U.S. Pat. No. 7,064,186; Sprecher, Cindy et al., 2003, incorporated herein by reference). The heterodimeric receptor for IL-31 comprises a heterodimer formed between IL-31Ra and OncostatinM receptor beta (OSMRb). IL-31Ra is the HUGO name for a protein called zcytor17 in commonly-owned U.S. published patent application number 20030215838, U.S. patent application Ser. No. 10/351,157, filed Jan. 21, 2003, herein incorporated by reference. The polynucleotide and polypeptide sequences for human IL-31 are shown in SEQ ID NOs: 1 and 2, respectively. The polynucleotide and polypeptide sequences for murine IL-31 are shown in SEQ ID NOs: 3 and 4, respectively. As used herein the term, IL-31 shall mean zcytor17lig as used in U.S. patent publication number 20030224487, as shown above. IL-31Ra has been previously described in commonly-owned U.S. patent application Ser. No. 09/892,949 filed Jun. 26, 2001, which is herein incorporated by reference.

Cysteine mutants of IL-31 are described in U.S. Patent Publication 2006-0228329, published Oct. 12, 2006 and are also incorporated herein by reference. Molecules of the mature human IL-31 polypeptide can have disulfide bonds between the cysteine residues of the mature polypeptide amino acid sequence A mutation of any of these three cysteines results in a mutant form of the human IL-31 protein that will only form one disulfide bond. The cysteines in these positions can be mutated, for example, to a serine, alanine, threonine, valine, or asparagine.

The amino acid sequence for the OSMR, and IL-31RA receptors indicated that the encoded receptors belonged to the Class I cytokine receptor subfamily that includes, but is not limited to, the receptors for IL-2, IL-4, IL-7, Lif, IL-12, IL-15, EPO, TPO, GM-CSF and G-CSF (for a review see, Cosman, "The Hematopoietin Receptor Superfamily" in Cytokine 5(2): 95-106, 1993). The zcytor17 receptor is fully described in commonly-owned PCT Patent Application No. US01/20484 (WIPO publication No. WO 02/00721; herein incorporated by reference).

The present invention includes the use of IL-31 molecules, including agonists, variants and fragments, having IL-31 activity to treat asthma and/or AHR. The invention includes administering to a subject the IL-31 molecule and contemplates both human and veterinary therapeutic uses. Illustrative veterinary subjects include mammalian subjects, such as farm animals and domestic animals.

The native polynucleotide and polypeptide sequences for the "long" form of IL-31RA are shown in SEQ ID NOs: 5 and 6, respectively. The native polynucleotide and polypeptide sequences for the "short" form of IL-31RA are shown in SEQ ID NOs: 7 and 8, respectively. Additional truncated forms of IL-31RA polypeptide appear to be naturally expressed. Both forms encode soluble IL-31RA receptors. The "long" soluble IL-31RA polynucleotide and polypeptide sequences are shown in SEQ ID NOs: 9 and 10, respectively. The "short" soluble IL-31RA polynucleotide and polypeptide sequences are shown in SEQ ID NOs: 11 and 12, respectively. The native polynucleotide and polypeptide sequences for mouse IL-31RA are shown in SEQ ID NOs: 13 and 14, respectively. The native polynucleotide and polypeptide sequences for human OSMRbeta are shown in SEQ ID NOs: 15 and 16, respectively. See PCT applications WO 02/00721 and WO 04/003140, both of which are incorporated by reference.

In allergic asthma, inhalation of allergens leads to an inflammatory cascade in which CD4+ T lymphocytes are thought to play a central role. The key contributions of CD4+ T cells in the pathogenesis of asthma have been highlighted by studies of Th2-type cytokines, such as IL-4, IL5, IL-9 and IL-13. These cytokines can mediate upregulation of adhesion molecules and inflammatory chemokine production, and thereby immune-cell recruitment, degranulation of eosinophils, synthesis of IgE, and hyper-reactivity of smooth muscle (reviewed 1). IL-4 and IL-13 are structurally related molecules that share the common IL-4Rα chain in receptor complexes. See Lin J. et al., Immunity 2:331-9, 1995; Smerz-Bertling C., and Duschl A., J. Biol. Chem. 270:966-70, 1995; and Zurawski S. et al., J. Biol. Chem. 270:13869-78, 1995. Although they exhibit overlapping function and both are associated with allergic disease, studies in IL-4 deficient animals have demonstrated that IL-13 may be especially critical for the induction of AHR. See Grunig G. et al., Science 282:2261-3, 1998; Herrick C. et al., J. Immunol. 170:2488-95, 2003; and Wills-Karp M. et al., Science 282:2258-61, 1998. IL-5 is central to eosinophil maturation, differentiation, activation and survival. The development of airway eosinophilia is associated with increased IL-5 expression in the airway mucosa and elevated concentrations of IL-5 in the luminal fluid and serum (Liu L. et al., J. Allergy Clin. Immunol.: 106:1063-9, 2000; and Kelly E. et al., Am. J. Respir. Crit. Care Med. 156:1421-8, 1997). Additionally, studies in mice have indicated the role of IL-5 in eosinophilia through depletion in murine models of asthma (Saito H. et al., J. Immunol. 168:3017-23, 2002; Tanaka H. et al., Am. J. Respir. Cell Mol. Biol. 19:19, 2004; and Tomaki M. et al., Pulm. Pharmacol. Ther. 15:161-8, 2002). Therefore Th2 mediated cytokines play an important role in generating the inflammation that characterizes allergic diseases.

IL-31 has been found to be produced more predominantly by activated Th2 cells compared to Th1-skewed cells (Dillon et al., 2004). Subsequent analysis of lung tissue from mice exposed to a model of allergen-induced asthma showed an upregulation of the receptor for IL-31, IL-31RA, suggesting a possible association of IL-31 with allergy. In that study, RNA was isolated from human IL-31 treated A549 cells, IL-31 treated SK-LU-1 cells, and untreated control cells using a RNeasy Midi Kit (Qiagen, Valencia, Calif.) according to the manufactures instructions. Gene expression profiling of the cells treated with IL-31 and the respective control cells was carried out using GEArray Q series cDNA expression arrays (SuperArray Inc., Bethesda, Md.). The Q Series cDNA expression arrays contain up to 96 cDNA fragments associated with a specific biological pathway, or genes with similar functions or structural features. Comparison of arrays from treated and control cells allows for a determination of the up and down regulation of specific genes. Probe labeling, hybridization and detection were carried out according to the manufactures instructions. Chemiluminscent signal detection and data acquisition was carried out on a Lumi-Imager workstation (Roche, Indianapolis, Ind.). The resulting image data was analyzed using ImageQuant 5.2 (Amersham Biosciences, Inc., Piscataway, N.J.) and GEArray Analyzer 1.2 (SuperArray Inc., Bethesda, Md.) software. Analysis of the results from the Human Interleukin and Receptor Q series HS-014N arrays, showed, after normalization, an approximate 4.7 fold increase of IL13RA2 signal in the IL-31 treated human SK-LU-1 cells and an approximate 2.2 fold increase of the IL13RA2 signal in the IL-31 treated human A549 cells. These results indicate that IL-31 significantly up regulated IL13RA2 in the SK-LU-1 and A549 cells. Both of these are established cell lines derived from human lung carcinomas (Blobel et al., Virchows Arch B Cell Pathol Incl Mol. Pathol., 1984; 45(4):407-29). More specifically, A549 is characterized as a human pulmonary epithelial cell line (Lin, et al., J Pharm Pharmacol., 2002 September; 54(9):1271-8; Martinez et al., Toxicol Sci., 2002 October; 69(2):409-23).

Interleukin-13 (IL13), a cytokine secreted by activated T lymphocytes, has been demonstrated to be both necessary and sufficient for the expression of allergic asthma and for use in experimental models of asthma, which include airway hyper responsiveness, eosinophil recruitment, and mucus overproduction (Wills-Karp et al., Science, 1998; 282:2258-2261). It has been shown, that selective neutralization of IL13 will ameliorate the asthma phenotype (Grunig et al., Science, 1998; 282:2261-2263). It has also been reported that IL13 is involved in the up regulation of mucin gene MUC8 expression in human nasal polyp epithelium and cultured nasal epithelium (Kimm et al., Acta Otolaryngol., 2002; September; 122(6):638-643; Seong et al., Acta Otolaryngol., 2002; June; 122(4):401-407). MUC8, a major airway mucin glycoprotein, is implicated as playing a role in the pathogenesis of mucus hypersecretion in chronic sinusitis with polps (Seong et al., Acta Otolaryngol., 2002; June; 122(4):401-407).

Functionally, IL13 signals through a receptor complex consisting of the interleukin-13 receptor alpha-1 chain (IL13RA1) and IL-4 receptor alpha (IL4RA) (Daines and Hershey, J Biol. Chem., 2002; 22(12):10387-10393). It has also been shown, that the interleukin-13 receptor alpha-2 (IL13RA2) binds IL13 with high affinity, but by itself (Daines and Hershey, J Biol. Chem., 2002; 22(12):10387-10393). This receptor lacks, however, the cytoplasmic domain necessary for signaling and, therefore, is considered to be a decoy receptor. It has been shown that IL13RA2 is predominately an intracellular molecule that can be quickly mobilized from intracellular stores and surface expressed following cellular treatment with interferon (IFN)-gamma. The surface expression of IL13RA2 after IFN-gamma treatment does not involve protein synthesis and results in diminished IL13 signaling (Daines and Hershey, J Biol. Chem., 2002; 22(12): 10387-10393).

The results of the gene expression array analysis for IL-31 indicate the action of IL-31 to be novel to that of IFN-gamma in that the IL-31 treatment of lung epithelial derived cell lines resulted in a significant increase of IL13RA2 gene expression. Thus, IL-31 treatment can be beneficial in cases where long-term up regulation of IL13RA2 expression and down regulation of IL13 is desired such as in asthma, airway hyperactivity (AHR), and mucin regulation, including chronic sinusitis with polyps.

The bioactive antagonists or antibody conjugates described herein can be delivered intravenously, intraarterially or intraductally, subcutaneously, topically, or may be introduced locally at the intended site of action.

Within an aspect, the invention provides a method of treating asthma, airway hyper-responsiveness, allergic rhinitis, and chronic obstructive pulmonary disease (COPD) comprising administering an IL-31 agonist to a mammal Within an embodiment the IL-31 agonist is selected from the group consisting of: a) a polypeptide of at least 70% sequence identity to the polypeptide of SEQ ID NO: 2 from residue 27 to residue 164; b) a polypeptide comprising the sequence of SEQ ID NO: 2 from residue 27 to residue 164; c) analogues of b); d) derivatives of b); e) variants of b); and f) fragments of b). Within an embodiment the inflammation is inhibited, minimized, prevented or neutralized.

The invention provides a method of treating asthma, airway hyper-responsiveness, allergic rhinitis, comprising administering an IL-31 agonist to a mammal. In an embodiment, the IL-31 agonist is selected from the group consisting of: a) a polypeptide of at least 90% sequence identity to the polypeptide of SEQ ID NO: 2 from residue 27 to residue 164; and b) a polypeptide comprising the sequence of SEQ ID NO: 2 from residue 27 to residue 164. In an embodiment, inflammation is inhibited, minimized, or neutralized. Within an embodiment the IL-31 agonist is produced in mammalian cells. In another embodiment the IL-31 agonist is produced in *E. coli*. In an embodiment, the cysteine residues of the amino acid sequence of the IL-31 agonist are mutated to produce homogenous preparations of IL-31.

Within an aspect the invention provides a method of treating asthma, airway hyper-responsiveness, allergic rhinitis, comprising administering an IL-31 agonist to a mammal wherein the IL-31 agonist is administered during sensitization or challenge. Within an embodiment the IL-31 agonist is not administered as a pre-treatment to the asthma, airway hyper-responsiveness or allergic rhinitis Within an embodiment production of proinflammatory cytokines in the lung and BAL fluid is inhibited, minimized, or neutralized. In an embodiment the proinflammatory cytokines are IL-5 or IL-13. In an embodiment the proinflammatory cytokines are IL-5 and IL-13.

Within an aspect the invention provides a method of inhibiting, minimizing, or neutralizing the production of proinflammatory cytokines in the lung and BAL fluid in a pulmonary inflammatory condition, comprising administering a polypeptide wherein the polypeptide is selected from the group consisting of: a) a polypeptide of comprising at least 90% sequence identity to the polypeptide of SEQ ID NO: 2 from residue 27 to residue 164; and b) a polypeptide comprising the sequence of SEQ ID NO: 2 from residue 27 to residue 164. In an embodiment, the polypeptide is produced in mammalian cells. In another aspect the polypeptide is produced in *E. coli*.

The invention provides a method for optimizing the dose of an IL-31 agonist used to treat asthma, airway hyper-responsiveness, or allergic rhinitis comprising determining the amount of the IL-31 agonist that produces a decrease in proinflammatory cytokines. In an embodiment, the proinflammatory cytokines are IL-5 or IL-13. In an aspect the proinflammatory cytokines are IL-5 and IL-13.

The invention provides a use of a pharmaceutical composition comprising an IL-31 agonist to treat, minimize, reduce or inhibit the symptoms of asthma, airway hyper-responsiveness or allergic rhinitis wherein the pharmaceutical composition is selected from the group consisting of: a) a polypeptide of comprising at least 90% sequence identity to the polypeptide of SEQ ID NO: 2 from residue 27 to residue 164; b) a polypeptide comprising amino acid residues 27 to 164 of SEQ ID NO: 2.

The invention provides a kit for determining the optimum dose for treating asthma, airway hyper-responsiveness or allergic rhinitis comprising: a) taking a sample of lung tissue or BAL fluid from a patient with asthma, airway hyper-responsiveness or allergic rhinitis; b) testing the sample in vitro to determine if an amount of an IL-31 agonist decreases proinflammatory cytokine production in the sample, wherein the amount of the proinflammatory cytokine is measured by determining the level of gene expression or protein; c) determining the dosage of the IL-31 agonist sufficient to reduce levels of the proinflammatory cytokine.

The invention provides a method of down-regulating the expression of IL-31Ra in a condition such as asthma, airway hyper-responsiveness or allergic rhinitis comprising administering an amount of an IL-31 agonist. In an embodiment, the IL-31 agonist is selected from the group consisting of: a) a polypeptide of at least 90% sequence identity to the polypeptide of SEQ ID NO: 2 from residue 27 to residue 164; and b) a polypeptide comprising the sequence of SEQ ID NO: 2 from residue 27 to residue 164. In an embodiment, inflammation is inhibited, minimized, or neutralized. In an embodiment., the IL-31 agonist is produced in mammalian cells. In another embodiment, the IL-31 agonist is produced in *E. coli*. In an embodiment the cysteine residues of the amino acid sequence of the IL-31 agonist are mutated to produce homogenous preparations of IL-31.

The invention is further illustrated by the following non-limiting examples.

EXAMPLES

Example 1

Analysis of IL-31 in Airway Hyper-responsiveness Murine Model

A) Sensitization and Airway Challenge

Female BALB/c and C57B1/6 mice 6 weeks of age were purchased from Charles River Laboratories and maintained under SPF conditions. Groups of mice 8 to 10 wks of age, were sensitized by intraperitoneal injection of 10 ug of OVA (Calbiochem) in 50% Imject Alum (Pierce) on days 0 and 7. Seven days later, mice were challenged on 2 consecutive days (days 14 and 15) with 20 ug of OVA in 50 ul PBS. Forty-eight hours following allergen challenge whole lung tissue, BAL cellular infiltrates, BAL fluid and serum from half the sensitized animals were collected for further analysis while the remaining mice were assessed for airway hyper responsiveness (AHR).

B) Bronchioalveolar Lavage

Bronchioalveolar lavage fluid was collected via intratracheal cannulation. Saline was slowly injected in the lung and withdrawn in 4×1 ml aliquots. The lavage fluids were centrifuged to isolate the BAL cells and the supernatant was frozen for later analysis. BAL cell pellets were resuspended at 2 million cells per ml and 150 ul was used for total and differential cell counts. Total BAL leukocyte counts were determined for each mouse via light microscopy using trypan blue exclusion. Differential cell counts in the lavage fluid of each animal were determined by H&E staining (DiffQuik; Merz & Dade, Dubingen, Switzerland) of air-dried and fixed cytospin slides. Cell counts were calculated by examining one hundred cells per cytospin (Phoenix Laboratories). The total number of different leukocytes was calculated from the data collection. Results are expressed as number of cells per lung.

C) Measurement of Airway Hyper-Responsiveness

Airway responsiveness was assessed as a change in airway function following challenge with aerosolized methacholine (MCh) using whole-body plethysmography (Buxco, Electronics, Shannon, Conn.) 14. Briefly, unrestrained, conscious mice were placed in a whole-body plethysmographic chamber and respiratory waveforms were measured for 5 min to obtain a basal line. After basal values were established, mice were challenged with aerosolized saline for the unchallenged control measurement and then increasing concentrations of MCh (0.075M to 0.3 M). Readings were taken over a 10 min period 3 min after each nebulization period. Data are expressed as fold increase above basal values using the dimensionless parameter PehnH.

D) RNA Isolation and Real-Time TaqMan PCR Analysis

Lung tissue and BAL cells were collected from animals 48 h following antigen challenge. Snap frozen whole tissue samples and BAL cell pellets, resuspended in RLT buffer, were stored at $-80°$ C. until processed for RNA isolation. Briefly, lung tissue was homogenized in RLT buffer (Qiagen) and extracted using the commercially available RNeasy kits as per the manufacturer's instructions (Qiagen, Valencia, Calif.). The RNA was transcribed into first strand cDNA using Taqman RT-PCR reagents (Applied Biosystems, Branchburk, N.J.), according to the manufacturer's protocol. Levels of murine IL-31, IL-31RA, IL-4, IL-5, IL-13, IFNg, TNFa, CD40, CD40L, Class II, Cathepsin L, IL-13Ra2, MIP-2, IL-8R, Eotaxin and OSMR mRNA were determined via multiplex real-time TaqMan PCR. Oligonucleotide primers and TaqMan probes were designed using the Primer Express software (PE Applied Biosystems, Foster City, Calif.) and were synthesized in house. Forward primer, reverse primer and probe sequences were generated. Levels of mRNA for each gene were calculated relative to the internal house-keeping gene, hypoxanthine-guanine-phosphoribosyl-transferase (HPRT) using the Comparative Ct method (User Bulletin # 2, PE Applied Biosystems).

E) BAL Fluid and Serum Cytokine Analysis

Cytokine levels in BAL fluid supernatants and serum samples were measured using the Mouse Cytokine LINCOplex kit (LINCO Research, St Charles, Miss.) and the Luminex100 plate reader (Luminex Corporation, Austin, Tex.) according to the manufacturer's instructions. Quantification of cytokines was performed by regression analysis from a standard curve generated from cytokine standards included in the kit. Lower limits of detection for IL-5 and IL-13 were 0.6 pg/ml and 4.7 pg/ml respectively.

F) IL-31 Administration by Osmotic Pump

Mouse IL-31 was delivered at a dose of 20 ug per day (approximately 1 mg/kg per day) for 14 days by an osmotic minipump (Alzet) implanted subcutaneously into the dorsum of BALB/c mice. PBS+0.1% BSA was included as the vehicle control. Pumps were implanted on day 3 to ensure IL-31 delivery throughout the course of the model.

G) Histopathology of Murine Lung

Lungs were fixed by inflation and immersion in 10% normal buffered formalin (NBF).

Immunohistochemistry of Human Lung 5 uM sections were incubated with primary antibodies diluted from 333 ng/ml to 1330 ng/ml for both IL31 and IL31RA for 60 min in ChemMate Antibody Dilution Buffer (part# ADB250, Ventana Medical systems). Tissues were washed twice in TBST, and then incubated for 45 min in biotinylated goat anti-rabbit Ab, 750 ng/ml in PBSB (catalog #BA-1000, Vector Labs). Slides were washed and incubated in Vectastain Elite ABC Reagent (catalog# PK-7100, Vector Labs) for 45 min and washed twice in TBST. Signals were developed with DAB+ (catalog# K-3468, DakoCytomation) for 10 min at room temperature. Tissue slides were then counterstained in hematoxylin (catalog# H-3401 Vector Labs), dehydrated and coverslipped in VectorMount (catalog# H-5000, Vector Labs).

Statistical Analysis

Analysis of variance (ANOVA) was used to determine the levels of difference between groups for BAL differentials, and serum IgE. Student's t test was performed to determine differences between groups for gene expression studies. The data are expressed as mean+SD. Differences were considered statistically significant when $p<0.05$.

Results:

Systemic delivery with IL-31 during a mouse model of allergic asthma results in decreased levels of IL-5 and IL-13 mRNA and protein. Preliminary analysis of lung tissue and BAL cellular infiltrates from animals in a mouse model of antigen-induced asthma showed that mRNA encoding IL-31RA, the receptor for IL-31, was up-regulated in both whole lung tissue and lung cellular infiltrates 48 h after airway antigen challenge (Dillon et al., 2004).

Purified IL-31 was delivered at 20 ug/day for 14 days during the course of the allergen-induced asthma model via subcutaneous insertion of a mini-osmotic pump. Forty-eight hours following allergen inhalation of sensitized mice we collected whole lung tissue, BAL cellular infiltrates, BAL fluid and serum. RNA isolated from lung tissue and BAL cells were analyzed via quantitative TaqMan PCR for expression of 16 genes, including IL-31RA, IL-31, IL-4, IL-5, IL-13, IFNg, TNFa, CD40, CD40L, Class II, Cathepsin L, IL-13Ra2, MIP-2, IL-8R, Eotaxin, and OSMR. Results from these studies showed significant down-regulation of IL-5 (p 0.013), IL-13 (p 0.003) and Cathepsin L (p 0.038) mRNA in whole lung tissue, and decreases in IL-4 (p 0.01), IL-5 (p 0.003), IL-13 (p<0.001), Cathepsin L (p 0.007), Class II (p 0.005), CD40 (p 0.011), and CD40L (p<0.001) in BAL cell mRNA from allergen sensitized and challenged animals treated with IL-31 compared to vehicle control treated animals. Analysis of BAL fluid for cytokines confirmed the down-regulation of both IL-5 and IL-13 (p<0.001). In addition, IL-31 treatment resulted in lower levels of IL-5 in the serum. Serum IL-13 could not be detected in either the control or IL-31-treated animals.

IL-31 treatment results in decreased lung inflammation and airway hyper-responsiveness following allergen sensitization and challenge. The classic triad of allergic asthma involves IgE production, airway hyper-responsiveness (AHR) and eosinophilic inflammation. AHR is a well-established characteristic of allergic asthma and is believed to be the result of airway mucosal inflammation. Clinical investigations have suggested a relationship between the presence of activated airway inflammatory cells, including T cells, mast cells, monocytes, eosinophils and neutrophils, morphologic changes in airway tissues, and the development of severity of AHR (See Bradley B., et al., J. Allergy Clin. Immunol 88:661-74, 1991; and Wardlaw A. et al., Am. Rev. Respir. Dis. 137:62-9, 1998). Analysis of airway infiltrating cells following allergen sensitization and challenge in the presence of daily IL-31 treatment resulted in significant decreases in lymphocytes (p 0.001), macrophages (p 0.029) and eosinophils (p 0.019) in BAL fluid. Histological analysis of formalin fixed lung tissue indicated that inflammatory cell infiltrates and goblet cell hyperplasia in lungs from mice treated with IL-31 were substantially less than vehicle controls, suggesting a beneficial effect of IL-31 in airway inflammation.

Analysis of AHR of IL-31-treated animals via whole body plethysmography indicated that mice treated with IL-31 exhibited less AHR compared to vehicle treated controls. No change was apparent in serum IgE levels between IL-31- or vehicle-treated mice. These data therefore indicate that IL-31 treatment decreases disease pathogenesis in a murine model of allergic asthma, possibly through the down-regulation of IL-5 and IL-13.

IL-31RA is expressed in human alveolar macrophages, type II pneumocytes and bronchiolar epithelium Immunohistochemical (IHC) analysis of IL-31RA expression in human asthmatic lung and normal tissues indicates IL-31RA is present on alveolar macrophages, type II pneumocytes (an epithelial derived cell type that is responsible for secretion of surfactant) and bronchiolar epithelium. Comparison between asthmatic lung and normal lung tissue showed no difference in the cellular staining pattern.

Example 2

Human Monocyte Staining

Whole blood (200 ml) was collected from a healthy human donor and mixed 1:1 with PBS in 50 ml conical tubes. Thirty ml of diluted blood was then underlayed with 15 ml of Ficoll Paque Plus (Amersham Pharmacia Biotech, Uppsala, Sweden). These gradients were centrifuged 30 min at 500 g and allowed to stop without braking. The RBC-depleted cells at the interface (PBMC) were collected and washed 3 times with PBS. The isolated human PBMC yield was $300 \times 10^6$ prior to selection described below.

The PBMCs were suspended in 3 ml MACS buffer (PBS, 0.5% BSA, 2 mM EDTA) and $1 \times 10^6$ cells were set aside for flow cytometric analysis. We next added 0.45 ml anti-human CD14 microbeads (Miltenyi Biotec) and the mixture was incubated for 20 min at 4 degrees C. These cells labeled with CD14 beads were washed with 30 ml MACS buffer, and then resuspended in 1.5 ml MACS buffer.

An LS column (Miltenyi) was prepared according to the manufacturer's instructions. The LS column was then placed in a MidiMACS magnetic field (Miltenyi). The column was equilibrated with 3 ml MACS buffer. The cells labeled with anti-human CD14 microbeads were then applied to the column. The CD14-negative cells were allowed to pass through. The column was rinsed with 10 ml ($2 \times 5$ ml) MACS buffer and the rinse was pooled with the CD14-negative flow-through cells. The column was then removed from the magnet and placed in a 15 ml falcon tube. CD14-positive cells were eluted by adding 5 ml MACS buffer twice to the column and bound cells flushed out using the plunger provided by the manufacturer. The yield of CD14+ selected human peripheral blood monocytes was $30 \times 10^6$ total cells. One million of these monocytes were set aside for flow cytometric analysis. The CD14-negative flow-through cells were counted and $1 \times 10^6$ cells were set aside for flow cytometric analysis.

The $1 \times 10^6$ PBMCs, CD14-positive and CD14-negative cells that had been set aside were stained and run on a fluorescence activated cell sorter (FACS) to assess the purity of the CD14+ selected human peripheral blood cells. A FITC-conjugated anti-human CD19 antibody, an anti-human CD56-PE Ab, an anti-human CD11b-CyChrome Ab, and an anti-human CD3-APC Ab (all from PharMingen) were used for staining the cells. The CD14+ selected cells were 88% CD14+. The PBMCs were 10% CD14+ and the CD14-negative cells were 0.1% CD14+.

The human CD14+ selected human peripheral blood monocytes were activated by incubating them at $2 \times 10^6$ cells/ml in RPMI+10% human ultraserum (Gemini Bioproducts, Calabasas, Calif.) with and without rhInterferon-gamma (IFNg) 10 ng/ml (R&D) for 4, 8, 12 or 24 hours at 37° C. in ultra low-attachment tissue culture plates (Corning/Costar). At each timepoint, the cells were harvested, pelleted, washed once with FACS stain buffer (PBS, 3% human ultraserum, 1% BSA, 10 mM HEPES) and counted.

The activated monocytes were stained by FACS as follows: $1 \times 10^6$ cells were combined with specific and non-specific antibody blocking reagents—soluble receptor IL-31RaCEE and zVen1CEE respectively—at 200 ug/ml or none. The cells were then combined with either 2.0 μg/mL of biotinylated mouse anti-human IL-31Ra or biotinylated mouse isotype negative control (Southern Biotechnology) or left unstained for 30 minutes on ice in FACS buffer. Cells were washed twice with FACS buffer and then stained with SA-PE (Jackson Immuno Laboratories) at 1:400 in combination with FITC-conjugated anti-human CD14 antibody at 1:100 (PharMingen) for 20 minutes on ice. Cells were then washed twice with FACS buffer and resuspended in 400 ul FACS buffer containing 7-aminoactinomycin D (Molecular Probes) at 1:800 and analyzed by FACS on a BD FACSCaliber using CellQuest software (Becton Dickinson, Mountain View, Calif.).

The biotinylation of mouse-anti-human IL-31Ra was done as follows: 205 μL of mouse anti-human IL-31Ra (clone#276.100.5.5) at 2.45 mg/mL was combined with 15 μL of 2 mg/mL EZ-link Sulfo-NHS-LC-biotin (Pierce, Rockford, Ill.) dissolved in ddH2O. This solution was incubated on a rocker for 30 minutes at room temperature. After biotinylation the solution was purified on a PD-10 column (Amersham Biosciences, Uppsala, Sweden).

Human CD14+ selected human peripheral blood monocytes activated with rhIFNg for 12 h and 24 h showed binding to the biotinylated mouse anti-human IL-31Ra reagent+SA-PE. The binding was most pronounced at the 12 h timepoint. This binding did not occur in cells initially combined with specific competitor protein IL-31. There was no staining with SA-PE alone or with the biotinylated mouse isotype negative control+SA-PE. No binding was observed with the biotinylated mouse anti-human IL-31Ra reagent+SA-PE on CD14+ selected human peripheral blood monocytes activated with rhIFNg for 4 h and 8 h.

Example 3

Effects of IL-31 on Allergen Induced Airway Hyper-Responsiveness 3.1 Materials and Methods
3.1.1 Mice.
Female BALB/c mice were purchased from Charles River Laboratories and maintained under SPF conditions. All experimental animals used were under a protocol approved by the Institutional Animal Care and Use Committee (IACUC) of ZymoGenetics. Mice were 11 weeks of age at onset of study.

Tg mice over-expressing murine IL31, driven by the lymphocyte-specific promoter/enhancer Eμ/lck, or the ubiquitous promoter EF1α were used to evaluate the effects of IL-31 in vivo. The serum of EF1μTg mice contained 0.3-1.1 ng/ml mIL-31, while the Eμ/lck Tg serum contained 10-43 ng/ml. Both types of IL-31 Tg mice develop a striking skin phenotype around 4-8 weeks of age, consisting of piloerection followed by mild to severe alopecia. The Tg skin is also highly pruritic, as evidenced by the scratching behavior of the mice, often excessive enough to induce excoriation and lesions of the skin.

3.1.2 Sensitization and Airway Challenge.

Mice between the age of 8 and 12 weeks were sensitized by 100 L intraperitoneal injection of 10 ug of OVA (Calbiochem) in 50% Imject Alum (Pierce) on days 0 and 7. One week later, mice were challenged intranasally on two consecutive days (days 14 and 15) with 20 g of OVA in 50 uL PBS. Forty-eight hours following intranasal challenge with OVA, whole lung tissue, bronchioalveolar lavage (BAL) cellular infiltrates, BAL fluid and serum were collected from animals. In some experiments, an extra group of animals were put on protocol and tested for airway hyper-responsiveness (AHR) by whole body plethysmography (WBP).

3.1.3 IL-31 Administration by Osmotic Pump.

Murine IL-31 was delivered for either 7 or 14 days by an osmotic mini-pump (Alzet) implanted subcutaneously into the dorsum of BALB/c mice. PBS+0.1% BSA was included as the vehicle control. The quantity of IL-31 delivered is outlined below. In general, delivery of IL-31 with a 14 day pump ensured that IL-31 was present in the circulation during both the allergen sensitization and challenges phases. The majority of experiments were performed with $E.\ coli$-derived IL-31 (SEQ ID NO: 17), however BHK-derived material (SEQ ID NO: 2) was shown to have a similar effect.

3.1.4 Measurement of Airway Hyper-Responsiveness.

Airway responsiveness was assessed as a change in airway function following challenge with aerosolized methacholine (MCh) using whole-body plethysmography (Buxco, Electronics, Shannon, Conn.). Briefly, unrestrained, conscious mice were placed in a whole-body plethysmographic chamber and respiratory waveforms were measured for 5 min to obtain a basal line. After basal values were established, mice were challenged with aerosolized PBS for the unchallenged control measurement and then increasing concentrations of MCh (0.075M to 0.3 M). Readings were taken over a 10 min period 3 min after each nebulization period. Data are expressed as fold increase above basal values using the dimensionless parameter Penh (enhanced pause).

3.1.5 Bronchoalveolar Lavage.

Bronchoalveolar lavage fluid was collected via intratracheal cannulation. PBS with 0.5% FBS was slowly injected in the lung and withdrawn in 3×1 ml aliquots. The lavage fluids were centrifuged to isolate the BAL cells and the supernatant was frozen for later analysis. BAL cell pellets were resuspended at 2 million cells per ml and 150 L was used for total and differential cell counts. Total BAL leukocyte counts were determined for each mouse via light microscopy using trypan blue exclusion. Differential cell counts in the lavage fluid of each animal were determined by H&E staining (DiffQuik; Merz & Dade, Dubingen, Switzerland) of air-dried and fixed cytospin slides. Cell counts were calculated by examining one hundred cells per cytospin (Phoenix Laboratories). The total number of different leukocytes was calculated from the data collection. Results are expressed number of total cells per lung.

3.1.6 RNA Isolation and Real-Time TaqMan PCR Analysis.

Lung tissue and BAL cells were collected from animals 48 h following antigen challenge. Lung tissues from animals were analyzed separately, whereas BAL cells from animals within a group were pooled, due to the small amount of material. Snap frozen whole tissue samples and BAL cell pellets, resuspended in RLT buffer, were stored at −80° C. until processed for RNA isolation. Briefly, lung tissue was homogenized in RLT buffer (Qiagen) and extracted using the commercially available RNeasy kits as per the manufacturer's instructions (Qiagen, Valencia, Calif.). The RNA was transcribed into first strand cDNA using TaqMan RT-PCR reagents (Applied Biosystems, Branchburk, N.J.), according to the manufacturer's protocol. Oligonucleotide primers and TaqMan probes were designed using the Primer Express software (PE Applied Biosystems, Foster City, Calif.) and were synthesized in house. Forward primer, reverse primer and probe sequences were prepared. Real-time PCR were run in triplicate in 384-well plates on ABI Prism 7900HT (Applied Biosystems). Real-time data were acquired and analyzed using SDS 2.0 software (Applied Biosystems) with manual adjustment of baseline and threshold parameters. Levels of mRNA for each gene were calculated relative to the internal housekeeping gene, hypoxanthine-guanine-phosphoribosyl-transferase (HPRT) using the Comparative Ct method (User Bulletin # 2, PE Applied Biosystems).

3.1.7 BAL Fluid Cytokine Analysis.

Cytokine levels in BAL fluid supernatants and serum samples were measured using a custom Mouse Cytokine LINCOplex kit (LINCO Research, St Charles, Miss.) and the Luminex100 plate reader (Luminex Corporation, Austin, Tex.) according to the manufacturer's instructions. Quantification of cytokines was performed by regression analysis from a standard curve generated from cytokine standards included in the kit.

3.1.8 Quantification of Serum IgE.

Serum levels of total IgE and OVA-specific IgE were measured by ELISA. ELISA microtiter plates (Nunc Maxisorb) were coated overnight with 100 ul/well of 2 ug/ml capture anti-IgE (Pharmingen cat#553413) in PBS at 4° C. Plates were then blocked with 200 ul/well SuperBlock (Pierce cat#37515) for 15 minutes RT, then washed with ELISA C. Diluted IgE standards (Pharmingen cat#557079) in ELISA B (PBS, 1% BSA) were plated serial 2 fold dilutions from 500 ng/ml. Serum samples diluted 1:50 in ELISA B were plated 100 ul/well. If measuring Ova-specific IgE concentrations, sera from mice that have been immunized and boosted with ova/alum was used as a positive reference and serum from naïve mice as a negative reference. Reference sera were diluted 1:50, same as sample sera. Plates were incubated overnight at 4° C. and then washed with ELISA C. Biotinylated detection anti-mouse IgE (Pharmingen cat#553419) at 2 ug/ml in ELISA B was then plated 100 ul/well, and incubated 60 minutes at RT. Washed plates in ELISA C, and then plated 100 ul/well of SA-HRP (Pharmingen cat#554066) diluted 1:1000 in ELISA B, and incubated 30 minutes at RT. After incubation, plates were washed with ELISA C, then developed using OPD (10 ml NaCitrate/citris acid pH5, 1 OPD tablet (Pierce, Cat#34006), 10 ul H2O2). Stopped development of ELISA plate with 0.1M H2SO4, and read on spectrophotometer at 490 nm.

Results 3.2.1 Expression of IL-31RA in Murine Airways 3.2.1.1 Regulation of IL-31RA and OSMR mRNA In initial studies of OVA sensitized and challenged mice, mRNA from lung tissues and cells from BAL were analyzed for expression of IL-31 receptor to determine the potential for IL-31 activity in allergen-induced airway inflammation. BALB/c and C57B1/6 mice were sensitized with OVA, then challenged intranasally with either OVA as the allergen or PBS as the control. Quantitative RT-PCR analysis of tissues suggested that IL-31Ra was significantly up-regulated in both lung tissue (FIG. 1) and in BAL cell infiltrates following allergen-challenge in sensitized mice. OSMR, the other subunit of the IL-31 receptor, was also found to be expressed in the lung, though expression did not appear to be regulated as a result of allergen sensitization. In contrast, in BAL cells OSMR levels were very low. These data suggest that IL-31 signaling may play a role in the development of airway inflammation following allergen sensitization.

3.2.1.2 IL-31RA Protein Expression

To determine where IL-31RA protein was expressed in murine lungs, we collected lungs from animals that had been sensitized with OVA and challenged intranasally with either OVA or PBS. We then analyzed expression of IL-31RA by immunohistochemistry and found that the major cell type expressing IL-31 appeared to be macrophages. We also noted staining in large monocytic cells that may represent resident monocytes. This was especially appreciated in the lung from PBS treated animals in which minimal inflammatory infiltrate was observed. It was also noted that the occasional positive staining macrophage was observed in the alveoli of these latter, "uninvolved" lungs.

3.2.2 Delivery of IL-31 in OVA-Induced Airway Hyper-Responsiveness 3.2.2.1 Experiment #1

To follow the observation that IL-31Ra was regulated during antigen-induced airway inflammation in mice, we studied the effect of IL-31 delivery on the development of airway inflammation. To this end, OVA-specific airway inflammation was generated in the presence or absence of circulating murine IL-31 in BALB/c animals. Briefly, BALB/c mice were sensitized intraperitoneally with 10 ug of OVA in Alum on day 0 and day 7. On day 3, five of the sensitized animals were implanted subcutaneously with an osmotic mini-pump that delivered murine IL-31 (BHK-derived) for 14 days at 20 ug of IL-31 per day (approximately 1 mg/kg per day). This rate of delivery resulted in approximately 20 ng/ml of IL-31 in the serum. Another group of five animals were implanted with pumps containing PBS+0.1% BSA as the vehicle control. Animals were then challenged intranasally on day 14 and 15 with OVA. A third group of animals were sensitized with OVA but challenged with PBS and were included as a baseline control (no inflammation). Forty-eight hours after the last intranasal challenge, tissues were collected for analysis. Lungs were lavaged for analysis of BAL cell infiltrates and mRNA was prepared from BAL cell infiltrates as well as whole lung homogenates for analysis of gene regulation. Serum was collected for analysis of cytokines and IgE levels.

3.2.2.1.1 Lung and BAL mRNA Analysis

Analysis of gene expression in lung with IL-31 delivery suggests that IL-31 can significantly decrease expression of genes that have been shown to be involved in the development of asthma and pulmonary inflammation, including IL-5, IL13 and Cathepsin L (p value 0.0137, 0.003 and 0.0381, respectively, BSA-treatment versus IL-31-treatment) (Table 1). There was also a trend towards decreases in the expression of IL-4, IL-31Ra, TNFa, CD40 and CD40L, though the results did not reach statistical significance. Interestingly, there was a significant increase in IL-8R gene expression following IL-31-treatment compared to vehicle-control animals and a trend towards increases in MIP-2, though this was not significant. MIP-2, and KC, are functional homologues of IL-8 in mice. MIP-2 and KC increase the functional activity of neutrophils including ingestion and killing of bacteria. The implications of these findings for IL-8R and MIP-2 are unclear but it is known that IL-8R is expressed on neutrophils and is required for neutrophil chemotaxis.

TABLE 1 mRNA Levels in Total Lung Homogenates from Vehicle- and IL-31-Treated Mice

| Gene | [a]Lung | | | Vehicle v IL-31 |
|---|---|---|---|---|
| | Vehicle-Treated | IL-31-Treated | PBS | p Value |
| IL-4 | 0.081 + 0.041 | 0.038 + 0.006 | 0.001 + 0.000 | NS (p = 0.0535) |
| IL-5 | 0.756 + 0.192 | 0.407 + 0.157 | 0.097 + 0.040 | p = 0.0137 |
| IL-13 | 0.236 + 0.043 | 0.099 + 0.026 | 0.002 + 0.001 | p = 0.003 |
| IL-31Ra | 1.276 + 0.597 | 0.605 + 0.332 | 0.053 + 0.008 | NS (p = 0.0591) |
| TNFa | 0.566 + 0.160 | 0.073 + 0.041 | 0.057 + 0.054 | NS |
| MIP-2 | 0.623 + 0.439 | 1.36 + 0.666 | 0.410 + 0.201 | NS |
| IL-8R | 3.148 + 0.452 | 7.998 + 4.20 | 3.595 + 0.489 | p = 0.0334 |
| BCL-6 | 4.645 + 0.487 | 4.962 + 0.632 | 2.409 + 0.279 | NS |
| CCL27 | 0.566 + 0.139 | 0.760 + 0.139 | 0.659 + 0.361 | NS |
| CCR10 | 0.418 + 0.052 | 0.569 + 0.388 | 0.444 + 0.027 | NS |
| TSLP | 1.844 + 0.344 | 1.982 + 0.310 | 1.844 + 1.029 | NS |
| Cathepsin L | 198.8 + 72.61 | 113.8 + 24.44 | 30.63 + 8.145 | p = 0.0381 |
| Class II | 23.10 + 7.489 | 18.02 + 8.432 | 10.73 + 1.605 | NS |
| CCL17 | 8.219 + 2.029 | 9.857 + 3.746 | 1.667 + 0.210 | NS |
| IL-13Ra | 0.604 + 0.468 | 0.568 + 0.833 | 0.004 + 0.002 | NS |
| Eotaxin-1 | 15.43 + 2.221 | 16.09 + 1.072 | 1.246 + 0.134 | NS |
| IL-10 | 0.182 + 0.049 | 0.179 + 0.045 | 0.016 + 0.009 | NS |
| CD40 | 8.469 + 2.745 | 5.830 + 1.366 | 3.501 + 0.294 | NS |
| CD40L | 0.747 + 0.241 | 0.493 + 0.123 | 0.479 + 0.054 | NS |

[a]Data are represented as mean + standard deviation of five animals per group. Statistical analysis was performed using an unpaired t-test comparing vehicle-treated groups with IL-31 treated animals. The PBS groups represent baseline values when animals have not challenged with OVA.

Analysis of gene expression in cells within the BAL showed genes that were similarly regulated to the lung tissues. IL-4, IL-5, IL-13, IL-31Ra, Cathepsin L, Class II, CCL17, IL-10, CD40, CD40L were all significantly down-regulated in mRNA from BAL cells pooled from animals within each group. Of note, IL-8R and MIP-2 showed a trend towards increased expression in the BAL cells, but the results were not statistically significant (Table 2).

TABLE 2 mRNA Levels in BAL Cell Homogenates from BSA- and IL-31-Treated Mice

| Gene | BAL | | | Vehicle v IL-31 |
| --- | --- | --- | --- | --- |
| | Vehicle-Treated | IL-31-Treated | PBS | p Value |
| IL-4 | 0.056 + 0.017 | 0.010 + 0.001 | ND | p = 0.0101 |
| IL-5 | 0.090 + 0.015 | 0.027 + 0.008 | 0.018 + 0.012 | p = 0.0032 |
| IL-13 | 0.080 + 0.006 | 0.018 + 0.003 | ND | p < 0.0001 |
| IL-31Ra | 2.28 + 0.179 | 1.41 + 0.227 | 0.008 + 0.006 | p = 0.0066 |
| TNFa | 0.469 + 0.073 | 0.542 + 0.035 | 2.166 + 0.249 | NS |
| MIP-2 | 3.782 ± 0.312 | 4.605 ± 0.488 | 3.335 + 0.221 | NS |
| IL-8R | 1.459 + 0.304 | 1.709 + 0.1244 | 0.161 + 0.037 | NS |
| BCL-6 | 1.983 + 0.694 | 0.652 + 0.0462 | 0.459 + 0.014 | p = 0.0295 |
| CCL27 | 0.103 + 0.048 | 0.058 + 0.015 | 0.025 + 0.006 | NS |
| CCR10 | 0.202 + 0.039 | 0.270 + 0.048 | 0.198 + 0.051 | NS |
| TSLP | 0.043 + 0.031 | 0.076 + 0.031 | 0.040 + 0.047 | NS |
| Cathepsin L | 731.3 + 69.52 | 426.5 + 80.06 | 42.60 + 4.661 | p = 0.0076 |
| Class II | 18.43 + 4.192 | 5.070 + 0.598 | 2.759 + 0.151 | p = 0.0054 |
| CCL17 | 10.89 + 1.584 | 8.236 + 0.306 | 0.347 + 0.048 | p = 0.0462 |
| IL-13Ra | 0.039 + 0.017 | 0.013 + 0.004 | ND | NS |
| Eotaxin-1 | 0.073 + 0.017 | 0.055 + 0.017 | 0.018 + 0.013 | NS |
| IL-10 | 0.326 + 0.046 | 0.130 + 0.019 | 0.009 + 0.008 | p = 0.0024 |
| CD40 | 0.493 + 0.116 | 0.190 + 0.022 | 0.045 + 0.015 | p = 0.0122 |
| CD40L | 0.780 + 0.028 | 0.214 + 0.100 | 0.060 + 0.012 | p = 0.0007 |

[a]Data are represented as mean + standard deviation of five animals per group. Statistical analysis was performed using an unpaired t-test comparing vehicle-treated groups with IL-31 treated animals. The PBS groups represent baseline values when animals have not challenged with OVA.

3.2.2.1.2 Serum Cytokines and IgE Levels

Analysis of serum cytokines showed significant decreases in circulating levels of IL-5 protein between vehicle-treated (110+15.7 pg/ml) and IL-31-treated mice (37+8.4 pg/ml) ($p<0.0001$). Although IL-6, IL-9, IL-10, IL-12, GM-CSF, MIP-1 and RANTES were detected, no differences were observed between treatment groups. IL-4 and IL-13 protein could not be detected in the serum of mice in this experiment.

No significant difference in circulating total IgE or OVA-specific IgE was noted between the two groups of animals.

3.2.2.1.3 BAL Differentials

Analysis of cellular differentials in the BAL showed significant decreases in the number of total lymphocytes in the BAL of IL-31-treated mice compared to vehicle-treated animals (p 0.0095) and a trend towards decreases in BAL eosinophils, though the differences were not statistically significant. The increased IL-8R mRNA expression in the lung and BAL tissues suggested there may be an increase in neutrophils in the BAL. Although there was a trend towards increased neutrophil numbers following IL-31-treatment, the results were not statistically significant due to the large variation within the groups and the small number of cells. It should also be noted that 48 hr is the optimal time-point for measurement of macrophage and eosinophil influx, not neutrophil infiltration. Analysis of earlier time-points for more precise assessment of neutrophil infiltration may be warranted.

3.2.2.2 Experiment #2

A repeat of Experiment #1 analyzing antigen-specific airway hyper-responsiveness, was performed in the presence or absence of circulating murine IL-31 in BALB/c animals.

3.2.2.2.1 Lung and BAL mRNA Levels

Only a subset of genes was analyzed in this experiment compared to Experiment #1. These genes included IL-4, IL-5, IL-13, IL-13Ra2, IL31RA, Cathepsin L and TNFa. A complete summary of levels of gene expression relative to the house-keeping control gene, HPRT are given in Table 3. In this experiment, significant decreases in gene expression for IL-13 and TNFa were observed for mice treated with IL-31 compared to vehicle control animals. Although there was a trend towards decreases in IL-5, IL-31RA and Cathepsin L mRNA, three genes which showed significant decreases in the first experiment, the differences between treatment groups were not statistically significant in this experiment. The results for the BAL mRNA are shown in Table 4 and show that similar genes to the first experiment were significantly down-regulated in this experiment upon IL-31-treatment. These genes include significant down-regulation of IL-5, IL-31RA and Cathepsin L. IL-13 levels were also significantly down-regulated but the levels of IL-13 mRNA detected for this analysis were at the lower limit of detection.

TABLE 3 mRNA Levels in Total Lung Homogenates from BSA- and IL-31-Treated Mice

| Gene | [a]Lung | | | [b]Vehicle v IL-31 |
| --- | --- | --- | --- | --- |
| | Vehicle-Treated | IL-31-Treated | PBS | p Value |
| IL-4 | 0.502 + 0.278 | 0.360 + 0.089 | 0.010 + 0.009 | NS |
| IL-5 | 1.345 + 0.480 | 0.807 + 0.347 | 0.204 + 0.06 | NS (p = 0.0772) |
| IL-13 | 0.084 + 0.046 | 0.033 + 0.017 | ND | p = 0.0492 |
| IL-31Ra | 2.178 + 0.607 | 1.849 + 0.691 | 0.211 + 0.066 | NS |
| TNFa | 2.028 + 0.427 | 1.355 + 0.435 | 1.749 + 0.924 | p = 0.0388 |

TABLE 3-continued mRNA Levels in Total Lung Homogenates from BSA- and IL-31-Treated Mice

| | [a]Lung | | | [b]Vehicle v IL-31 |
|---|---|---|---|---|
| Gene | Vehicle-Treated | IL-31-Treated | PBS | p Value |
| Cathepsin L | 534.7 + 208.8 | 349.2 + 81.03 | 240.1 + 19.82 | NS |
| IL-13Ra2 | 1.043 + 0.342 | 0.940 + 0.424 | 0.024 + 0.001 | NS |

[a]Data are represented as mean + standard deviation of five animals per group.
[b]Statistical analysis was performed using a unpaired t-test comparing vehicle-treated groups with IL-31 treated animals. The PBS groups represent baseline values when animals have not challenged with OVA.
NS = not significant,
ND = not detected

TABLE 4 mRNA Levels in BAL Cell Homogenates from BSA- and IL-31-Treated Mice

| | aBAL | | | bVehicle v IL-31 |
|---|---|---|---|---|
| Gene | Vehicle-Treated | IL-31-Treated | PBS | p Value |
| IL-4 | 0.064 + 0.029 | 0.056 + 0.003 | ND | NS |
| IL-5 | 0.106 + 0.006 | 0.048 + 0.001 | ND | p < 0.0001 |
| IL-13 | 0.009 + 0.001 | 0.002 + 0.001 | ND | p = 0.0007 |
| IL-31Ra | 2.198 + 0.189 | 1.536 + 0.180 | 0.006 + 0.002 | p = 0.0118 |
| TNFa | 1.138 + 0.281 | 2.047 + 0.836 | 2.546 + 0.278 | NS |
| Cathepsin L | 424.9 + 93.04 | 150.9 + 20.04 | 31.61 + 2.99 | p = 0.0076 |
| IL-13Ra2 | 0.033 + 0.010 | 0.027 + 0.011 | ND | NS | aData are represented as mean + standard deviation of five animals per group.
bStatistical analysis was performed using an unpaired t-test comparing vehicle-treated groups with IL-31 treated animals. The PBS groups represent baseline values when animals have not challenged with OVA.
NS = not significant,
ND = not detected

3.2.2.2.2 BAL Fluid Cytokines

Results of the analysis of cytokines in the BAL fluid are summarized in Table 5. Consistent with results for regulation of mRNA in the lung and BAL cells, analysis of protein levels in the BAL fluid show significant decreases in IL-5 (p<0.0001) and IL-13 (p<0.0001). In addition, significant increases in KC (p 0.0332) and MCP-1 (p 0.007) were observed in mice treated with IL-31. Although KC mRNA expression was not tested in this experiment, the previous experiment had shown evidence for KC up-regulation following IL-31 treatment. The detection of protein in the BAL fluid supports the finding that IL-31-treatment up-regulates KC levels in the lung. Levels of GM-CSF, IFN-g, IL-10, IL-12, IL-1b, IL-4, IL-6, IL-9 and RANTES were undetectable. MIP-1a and TNFa were detected but no difference were observed between IL-31-treated and untreated animals (Table 5).

TABLE 5

Cytokine Levels in BAL Fluid from BSA- and IL-31-Treated Mice

| | aBAL Fluid Cytokines | | Vehicle v IL-31 |
|---|---|---|---|
| Cytokine | Vehicle-Treated | IL-31-Treated | p Value |
| IL-13 | 18.61 + 1.93 | 5.23 + 1.30 | p < 0.0001 |
| IL-5 | 39.37 + 2.59 | 15.62 + 2.60 | p < 0.0001 |
| KC | 22.81 + 1.63 | 40.59 + 7.32 | p = 0.0032 |
| MCP-1 | 3.11 + 1.72 | 10.46 + 1.89 | p = 0.007 |
| MIP-1a | 6.11 + 0.59 | 7.17 + 1.68 | NS |
| TNFa | 1.11 + 1.20 | 1.70 + 1.15 | NS | aData are represented as mean + standard deviation of five animals per group. Statistical analysis was performed using an unpaired t-test comparing vehicle-treated groups with IL-31 treated animals. The PBS groups represent baseline values when animals have not challenged with OVA.

3.2.2.2.3 Serum Cytokines and IgE Levels

Analysis of serum cytokines suggested no statistically significant decreases in circulating levels of any of the cytokines detected including IL-5, IL-6, IL-9, IL-10, IL-12, IL-13, GM-CSF, MIP-1α and TNFa. IL-4 and RANTES protein could not be detected in the serum of mice in this experiment.

No statistically significant difference in circulating total IgE or OVA-specific IgE was noted between the two groups of animals.

3.2.2.2.4 BAL Differentials

Differential analysis of cells in the BAL suggested, similar to the findings in the first experiment, that IL-31 treatment resulted in a significant decrease in infiltrating eosinophils and a trend towards decreases in lymphocytes, though in this case, the differences for lymphocytes were not statistically significant. In this experiment, the observed increase in neutrophils with IL-31 treatment compared to vehicle control animals did reach significance only when tested in a unpaired t-tailed t-test (p=0.0203), and is consistent with the finding of increased KC in the BAL fluid. However, statistical analysis using a two-way ANOVA, to analyze all data and all parameters together, suggested that the differences in neutrophils between the two groups was not statistically significant.

3.2.2.3 Experiment #3

Similarly to the previous two experiments, analysis of antigen-specific airway hyper-responsiveness was performed in the presence or absence of circulating murine IL-31 in BALB/c animals.

3.2.2.3.1 Lung and BAL mRNA Levels

A complete summary of levels of gene expression relative to the house-keeping control gene, HPRT are given in Table 5. The significant decreases observed in IL-4, IL-5, IL-13 and IL-31Ra gene expression in mice treated with IL-31 compared to vehicle controls is consistent with the previous two experiments (Table 6). As seen in Experiment #1, there was also a trend towards increases in IL-8R gene expression in the IL-31-treated group compared to vehicle-treated mice however the differences were not statistically significant.

The results for the BAL mRNA are shown in Table 6 and reflect the results found for the lung. IL-31-treatment induces significant down-regulation of IL-4, IL-5, IL-13, and IL-31RA and increases in IL-8R mRNA expression in the BAL cells (Table 7).

vehicle control animals (p=0.0405 and p=0.0387, respectively) (Table 8). IL-1b, IL-10, MIP-1a and RANTES levels were below the limit of detection of the assay.

TABLE 8

Cytokine Levels in BAL Fluid from BSA- and IL-31-Treated Mice

| | [a]BAL Fluid Cytokines | | Vehicle v IL-31 |
|---|---|---|---|
| Cytokine | Vehicle-Treated | IL-31-Treated | p Value |
| IL-2 | 1.816 + 0.695 | 1.938 + 0.621 | NS |
| IL-4 | 3.19 + 0.627 | 3.891 + 3.339 | NS |
| IL-5 | 80.38 + 21.96 | 47.49 + 18.11 | p = 0.0133 |
| IL-6 | 2.104 + 1.478 | 2.658 + 1.531 | NS |
| IL-9 | 47.47 + 14.79 | 36.33 + 4.002 | NS |
| IL-12 | 12.76 + 2.038 | 13.25 + 2.976 | NS |
| IL-13 | 46.42 + 5.140 | 25.10 + 3.843 | p < 0.0001 |
| IFNg | 5.238 + 1.750 | 6.349 + 2.310 | NS |
| TNFa | 8.026 + 1.882 | 8.126 + 2.874 | NS |
| GM-CSF | 26.27 + 5.496 | 29.72 + 4.761 | NS |
| MCP-1 | 19.79 + 3.025 | 16.89 + 1.481 | p = 0.0387 |
| KC | 15.43 + 5.737 | 9.969 + 2.819 | p = 0.0405 |

[a]Data are represented as mean + standard deviation of five animals per group. Statistical analysis was performed using an unpaired t-test comparing vehicle-treated groups with IL-31 treated animals.

TABLE 6 mRNA Levels in Total Lung Homogenates from Vehicle- and IL-31-Treated Mice

| | [a]Lung | | | Vehicle v IL-31 |
|---|---|---|---|---|
| Gene | Vehicle-Treated | IL-31-Treated | PBS | p Value |
| IL-4 | 0.402 + 0.081 | 0.259 + 0.069 | 0.004 + 0.001 | p = 0.0266 |
| IL-5 | 1.677 + 0.521 | 0.617 + 0.081 | 0.172 + 0.022 | p = 0.0054 |
| IL-13 | 0.483 + 0.205 | 0.036 + 0.047 | ND | p = 0.0040 |
| IL-31Ra | 6.306 + 2.055 | 2.132 + 1.341 | 0.274 + 0.044 | p = 0.0102 |
| CCL17 | 44.18 + 18.62 | 55.13 + 26.47 | 4.72 + 1.89 | NS |
| IL-8R | 56.59 + 18.81 | 130.13 + 83.79 | 177.1 + 46.82 | NS (p = 0.0942) |
| IL-13Ra2 | 1.145 + 0.304 | 0.779 + 0.343 | 0.013 + 0.006 | NS |

[a]Data are represented as mean + standard deviation of five animals per group. Statistical analysis was performed using an unpaired t-test comparing vehicle-treated groups with IL-31 treated animals.

TABLE 7 mRNA Levels in BAL Cell Homogenates from BSA- and IL-31-Treated Mice

| | aBAL | | | Vehicle v IL-31 |
|---|---|---|---|---|
| Gene | Vehicle-Treated | IL-31-Treated | PBS | p Value |
| IL-4 | 0.426 + 0.021 | 0.344 + 0.015 | ND | p = 0.0055 |
| IL-5 | 0.573 + 0.176 | 0.188 + 0.019 | 0.009 + 0.004 | p = 0.0195 |
| IL-13 | 0.243 + 0.084 | 0.002 + 0.001 | ND | p = 0.0076 |
| IL-31Ra | 18.89 + 5.21 | 7.496 + 1.629 | 0.079 + 0.011 | p = 0.0224 |
| CCL17 | 84.89 + 7.725 | 99.12 + 9.007 | 4.557 + 0.266 | NS |
| IL-8R | 39.35 + 9.557 | 105.32 + 10.78 | 17.31 + 3.713 | p = 0.0014 |
| IL-13Ra2 | 0.143 + 0.064 | 0.193 + 0.090 | 0.005 + 0.008 | NS | aData are represented as mean + standard deviation of five animals per group. Statistical analysis was performed using an unpaired t-test comparing vehicle-treated groups with IL-31 treated animals.

3.2.2.3.2 BAL Fluid Cytokines

Results of the analysis of cytokines in the BAL fluid are summarized in Table 8. Similarly to the previous data, these data show significant decreases in IL-5 (p=0.0133) and IL-13 (p<0.0001) with IL-31 Treatment. However, in contrast to the previous experiments, analysis of KC and MCP-1 in the BAL showed decreased levels in IL31-treated mice compared to 3.2.2.3.3 Serum Analysis No significant difference in circulating total IgE or OVA-specific IgE was noted between the two groups of animals. Serum cytokines were not measured 3.2.2.3.4 BAL Differentials Differential analysis of cells in the BAL suggested that IL-31 treatment resulted in a significant decrease in infiltrat ing lymphocytes (p=0.0011), macrophages (p=0.0291) and eosinophils (p=0.0198), as has been observed in previous experiment. There was no statistical difference in the number of neutrophils found in BAL of mice in the two treatment groups.

3.2.2.4 Experiment #4

In order to determine the overall effect of IL-31 treatment on airway inflammation, this study was designed to include the collection of lung tissue for immunohistochemistry and to analyze the airway hyper-responsiveness of live mice to allergen challenge by WBP. The mice were sensitized and challenged with OVA and treated with IL-31 (*E. coli*-derived) or vehicle as previously described in the last three experiments. Forty-eight hours the after the last intranasal challenge, tissue was collected for analysis as before. In addition, a portion of the lung was collected and preserved in 10% buffered neutral formalin or in Zn TRIS fixative. The formalin fixed tissue was processed, embedded in paraffin, sectioned and the resulting slides stained with hematoxylin and eosin for microscopic evaluation.

3.2.2.4.1 Lung and BAL mRNA Levels

A complete summary of levels of gene expression relative to the house-keeping control gene, HPRT are given in Table 9. As expected, a significant decrease in IL-5 and IL-31Ra gene expression was observed in mice treated with IL-31 compared to vehicle-treated controls (Table 9). There was a trend towards decreases in IL-4, IL-13 and Cathepsin L and significant decreases in IFNg and CD40L, which has been observed previously. In addition, we once again observe a statistically significant increase in IL-8R expression in total lung homogenates (Table 9).

The gene expression levels in BAL cell infiltrates are summarized in Table 10 and indicate, similar to previous studies, that IL-31-treatment induces significant down-regulation of most of genes tested including IL-4, IL-5, IL-13 and Cathepsin L. There was a trend towards decreasing IL-31Ra expression, though not statistically significant. In this particular analysis we found a significant increase in MIP-2 and TNFa, both of which have shown trends towards an increase in BAL cell mRNA from previous experiments (i.e. Experiment #1 and/or Experiment #2). IL-8R was also significantly increased in BAL mRNA, suggesting a disassociation between regulation of genes in the BAL cells and total lung.

TABLE 9

Levels in Total Lung Homogenates from Vehicle- and IL-31-Treated Mice

| Gene | $^a$Lung | | | Vehicle v IL-31 |
| --- | --- | --- | --- | --- |
| | Vehicle-Treated | IL-31-Treated | PBS | p Value |
| IL-4 | 0.042 + 0.027 | 0.02 + 0.014 | 0.001 + 0.000 | NS |
| IL-5 | 0.298 + 0.056 | 0.097 + 0.048 | 0.029 + 0.010 | p = 0.0016 |
| IL-13 | 0.068 + 0.070 | 0.023 + 0.016 | ND | NS |
| IL-31Ra | 0.713 + 0.129 | 0.352 + 0.263 | 0.047 + 0.015 | p = 0.0484 |
| TNFa | 0.245 + 0.094 | 0.167 + 0.031 | 0.342 + 0.121 | NS |
| MIP-2 | 0.570 + 0.194 | 0.482 + 0.174 | 0.398 + 0.238 | NS |
| IL-8R | 1.369 + 0.672 | 10.85 + 6.129 | 6.162 + 1.876 | p = 0.0337 |
| IFNg | 0.135 + 0.019 | 0.069 + 0.034 | 0.033 + 0.008 | p = 0.0153 |
| CCL27 | 0.359 + 0.162 | 0.637 + 0.028 | 0.662 + 0.073 | p = 0.0146 |
| Cathepsin L | 86.49 + 39.68 | 37.90 + 33.67 | 18.59 + 1.48 | NS (p = 0.0670) |
| Class II | 23.73 + 9.840 | 17.25 + 6.162 | 7.195 + 0.347 | NS |
| IL-13Ra | ND | ND | ND | ND |
| Eotaxin | 5.696 + 2.416 | 5.073 + 3.232 | 0.317 + 0.057 | NS |
| IL-10 | 0.145 + 0.086 | 0.112 + 0.076 | 0.005 + 0.003 | NS |
| CD40 | 3.343 + 0.559 | 2.562 + 0.832 | 1.835 + 0.138 | NS |
| CD40L | 0.576 + 0.165 | 0.301 + 0.137 | 0.183 + 0.071 | p = 0.0426 |

$^a$Data are represented as mean + standard deviation of five animals per group. Statistical analysis was performed using an unpaired t-test comparing vehicle-treated groups with IL-31 treated animals. The PBS group represents baseline with no OVA challenge.

TABLE 10 mRNA Levels in BAL Cell Homogenates from Vehicle- and IL-31-Treated Mice

| Gene | $^a$BAL | | | Vehicle v IL-31 |
| --- | --- | --- | --- | --- |
| | Vehicle-Treated | IL-31-Treated | PBS | p Value |
| IL-4 | 0.0867 + 0.005 | 0.011 + 0.002 | ND | p < 0.0001 |
| IL-5 | 0.188 + 0.005 | 0.054 + 0.013 | ND | p < 0.0001 |
| IL-13 | 0.0352 + 0.001 | 0.0026 + 0.001 | ND | p < 0.0001 |
| IL-31Ra | 1.719 + 0.760 | 0.671 + 0.202 | 0.011 + 0.007 | NS |
| TNFa | 0.293 + 0.045 | 0.582 + 0.085 | 5.38 + 0.404 | p = 0.0065 |
| MIP-2 | 0.334 + 0.045 | 1.108 + 0.254 | 9.20 + 0.134 | p = 0.0065 |
| IL-8R | 1.99 + 0.139 | 0.616 + 0.023 | 1.33 + 0.095 | p < 0.0001 |
| IFNg | 0.196 + 0.011 | 0.0681 + 0.006 | 0.003 + 0.001 | p < 0.0001 |
| CCL27 | 0.094 + 0.006 | 0.057 + 0.02 | 0.030 + 0.003 | p = 0.0385 |
| Cathepsin L | 851.6 + 40.64 | 284.5 + 20.8 | 46.07 + 10.03 | p < 0.0001 |
| Class II | 27.69 + 3.34 | 5.41 + 0.476 | 1.265 + 0.043 | p = 0.0003 |
| Eotaxin | 0.011 + 0.003 | ND | ND | ND |
| IL-10 | 0.466 + 0.051 | 0.075 + 0.008 | 0.004 + 0.001 | p = 0.002 |

TABLE 10-continued mRNA Levels in BAL Cell Homogenates from Vehicle- and IL-31-Treated Mice

| | [a]BAL | | | Vehicle v IL-31 |
|---|---|---|---|---|
| Gene | Vehicle-Treated | IL-31-Treated | PBS | p Value |
| CD40 | 0.771 + 0.033 | 0.079 + 0.010 | 0.024 + 0.002 | P < 0.0001 |
| CD40L | 0.711 + 0.012 | 0.234 + 0.013 | 0.016 + 0.004 | p < 0.0001 |

[a]Data are represented as mean + standard deviation of five animals per group. Statistical analysis was performed using an unpaired t-test comparing vehicle-treated groups with IL-31 treated animals. The PBS group represents baseline with no OVA challenge.

3.2.2.4.2 Serum

Serum was analyzed for total and antigen-specific IgE in IL-31-treated and vehicle-treated OVA-sensitized mice. In this particular experiment we found a significant decrease in the level of OVA-specific IgE in IL-31 treated mice compared to vehicle-treated animals (p=0.0070). However, the differences in total IgE levels between the two treatment groups did not reach statistical significance.

Serum cytokines and cytokine levels in the BAL fluid were not analyzed in this experiment.

3.2.2.4.3 Lung Histology

Histological examination of the lungs from IL-31 treated and vehicle treated animals showed a number of microscopic changes associated with sensitization and challenge with OVA, including: 1) multifocal to diffuse peribronchial/perivascular subacute inflammation that was characterized by accumulations of eosinophils and/or neutrophils (segmented nucleus with eosinophilic cytoplasm) and large monocytic type cells along with some lymphocytes; 2) diffuse epithelial/goblet cell hyperplasia; and 3) multifocal macrophage infiltrate in the alveoli with some multinucleated giant cell formation.

In some areas of the lung, there was evidence of perivascular edema with or without variable amounts of inflammatory infiltrates as well as evidence of interstitial fibrosis. When compared with the lungs from vehicle-treated animals that were sensitized and challenged with OVA, the inflammatory changes in the IL-31-treated animals were substantially less severe suggesting a beneficial effect of IL-31. Representative images of lung from vehicle-treated and IL-31-treated animals are shown in.

The lung sections from vehicle-treated animals showing severe inflammation also showed an increased number of F4/80+ macrophage infiltrating the alveoli, peribronchial and perivascular subacute inflammatory area. Lung sections from IL-31-treated animal showed less inflammation and also showed significant lower number of F4/80+ macrophage infiltrate. Enumeration of F4/80+ macrophages showed that the F4/80+ cell density was significantly lower in IL31-treated animals compared to BSA-treated mice (p=0.0154, Unpaired-T test).

OVA-sensitized animals were challenged intranasally and measured for airway hyper-responsiveness by whole body plethysmography. Analysis of the dimensionless parameter enhanced pause (PenH) following challenge with increasing concentration of methacholine suggested that IL-31-treated animals were less sensitive to allergen challenge compared to vehicle-treated mice. This data support the histopathology findings and suggest that IL-31 treatment decreases airway inflammation to allergen.

BAL cell differentials were not performed in this experiment 3.2.2.5 Summary

The data presented suggest that IL-31 delivery during antigen sensitization and airway challenge in mice results in down-regulation of pulmonary inflammation, as assessed by histology and airway hyper-responsiveness via whole body plethysmography. Analysis of gene regulation in total lung homogenates and in mRNA from infiltrating cells in the lung suggest that IL-31 can consistently down-regulate genes that have been associated with pulmonary inflammation and asthma including, IL-5, IL-13 and Cathepsin L. Genes generally associated with inflammation were also found to be down-regulated and include IFNg, CD40 and CD40L. The IL-31 effect on gene down-regulation appeared to be more consistent in mRNA from BAL infiltrating cells compared to total lung mRNA. Moreover, when cytokine levels in the BAL fluid were tested, concordant down-regulation of protein was often observed. This down-regulation of Th2 and inflammatory genes often translated to decreases in BAL cell infiltrates, particularly eosinophils, macrophages and lymphocytes. Analysis of F4/80+ macrophage cell numbers in lungs of IL-31-treated animals via histomorphometry yielded quantitative data that confirmed the decrease in tissue macrophages in the lung. Furthermore, analysis of general pathology associated with pulmonary allergic inflammation showed decreases in severity of disease with delivery of IL-31. These data therefore suggest that delivery of IL-31 during allergen sensitization and challenge can reduce the severity of pulmonary inflammation through an as yet unknown mechanism.

3.2.3 Dose Response to IL-31

2.3.1 Experiment #1

We next decided to investigate the minimum dose of IL-31 required for the inhibitory effects on pulmonary inflammation following OVA sensitization and intranasal challenge in mice. In the first experiment, Alzet 14-day osmotic pumps were loaded with 10-fold decreasing concentrations of IL-31, from 20 ug/day to 0.02 ug/day, and implanted in mice during OVA allergen sensitization and challenge as previously described. Five animals per group were analyzed.

3.2.3.1.1 Lung and BAL Cell mRNA

Previous studies have shown that delivering 20 ug/day of IL-31 decreases expression of a number of genes in the lung following allergen sensitization and challenge. Results summarized in Table 11 show that for some of these genes, this effect of IL-31 is dose-dependant. Comparison of gene expression levels in the group of mice treated with 20 ug/day of IL-31 with those receiving 10-, 100- or 1000-fold less IL-31 shows significant differences. Genes including, IL-5, IL-13, IL-31Ra, TNFa, IFNg, Class II, IL-13Ra2, Eotaxin, IL-10, CD40 and CD40L, were more highly expressed at lower doses of IL-31, especially at the 0.2 and 0.02 ug/day doses. Cathepsin L and IL-4 showed trends towards increased expression with lower doses of IL-31, but these trends were not significant. Furthermore, IL-8R and MIP-2, which have been shown to be increased following 20 ug/day IL-31-treatment, also showed significant IL-31-dose dependency.

TABLE 11 mRNA Analysis of Lungs from IL-31-Treated Mice

| | [a]IL-31 Concentration in pump | | | |
|---|---|---|---|---|
| Gene | [b]20 ug/day | 2 ug/day | 0.2 ug/day | 0.02 ug/day |
| IL-4 | 0.025 + 0.017 | 0.047 + 0.025 | 0.041 + 0.006 | 0.042 + 0.005 |
| IL-5 | 0.094 + 0.033 | 0.195 + 0.115 | 0.292 + 0.131** | 0.251 + 0.035* |
| IL-13 | 0.012 + 0.007 | 0.057 + 0.030* | 0.036 + 0.016 | 0.077 + 0.041** |
| IL-31Ra | 0.294 + 0.157 | 0.543 + 0.208 | 0.826 + 0.312* | 0.988 + 0.287** |
| TNFa | 0.340 + 0.082 | 0.370 + 0.088 | 0.432 + 0.0804 | 0.656 + 0.204** |
| MIP-2 | 12.25 + 9.78 | 4.942 + 4.497 | 6.436 + 1.050 | 4.555 + 2.648 |
| IL-8R | 6.943 + 2.740 | 5.498 + 2.103 | 3.236 + 1.412* | 3.477 + 0.914* |
| IFNg | 0.084 + 0.026 | 0.150 + 0.052 | 0.279 + 0.154* | 0.229 + 0.125 |
| CCL27 | 1.114 + 0.184 | 0.834 + 0.130* | 0.993 + 0.152 | 0.914 + 0.129 |
| Cathepsin L | 49.32 + 12.92 | 68.84 + 14.57 | 98.11 + 49.52 | 78.10 + 31.41 |
| Class II | 30.70 + 7.802 | 41.56 + 7.701 | 50.62 + 8.797* | 52.79 + 31.41** |
| IL-13Ra2 | 0.068 + 0.044 | 0.095 + 0.035 | 0.116 + 0.026 | 0.172 + 0.032** |
| Eotaxin | 7.820 + 3.676 | 13.69 + 2.827** | 9.327 + 1.638 | 12.10 + 1.613* |
| IL-10 | 0.057 + 0.032 | 0.110 + 0.018* | 0.105 + 0.011* | 0.108 + 0.039* |
| CD40 | 5.606 + 1.180 | 5.616 + 1.180 | 9.194 + 1.910** | 6.772 + 2.000 |
| CD40L | 0.734 + 0.335 | 0.790 + 0.182 | 1.899 + 1.343* | 1.308 + 0.169 |

[a]Data a presented as mean + standard deviation of five animals per group.
[b]**p<0.01 and *p<0.05 using one-way ANOVA with Dunnett's post test, comparing IL-31-treatment at lower concentrations (2, 0.2 and 0.02 ug/day) to treatment the standard 20 ug/day used in previous experiments.

TABLE 12 mRNA Levels in BAL Cell Homogenates from Dose curve IL-31-Treated Mice

| | [a]IL-31 Concentration in pump (ug/day) | | | |
|---|---|---|---|---|
| Gene | [b]20 ug/day | 2 ug/day | 0.2 ug/day | 0.02 ug/day |
| IL-4 | 0.039 + 0.009 | 0.031 + 0.007 | 0.055 + 0.009 | 0.049 + 0.005 |
| IL-5 | 0.016 + 0.002 | 0.034 + 0.003* | 0.080 + 0.010** | 0.082 + 0.006** |
| IL-13 | 0.001 + 0.000 | 0.005 + 0.000** | 0.023 _ 0.001** | 0.015 + 0.000** |
| IL-31Ra | 0.850 + 0.250 | 1.286 + 0.079* | 1.605 + 0.129** | 1.420 + 0.100** |
| TNFa | 0.446 + 0.013 | 0.351 + 0.034* | 0.282 + 0.039** | 0.342 + 0.030** |
| MIP-2 | 5.041 + 1.058 | 4.983 + 0.582 | 1.771 + 0.212** | 1.304 + 0.095** |
| IL-8R | 4.269 + 0.308 | 2.244 + 0.246** | 2.678 + 0.138** | 3.114 + 0.202** |
| IFNg | 0.072 + 0.012 | 0.162 + 0.020** | 0.242 + 0.019** | 0.288 + 0.040** |
| Cathepsin L | 109.0 + 15.09 | 75.35 + 5.911** | 172.8 + 30.58 | 103.1 + 6.720 |
| Class II | 2.148 + 0.142 | 4.676 + 0.407** | 9.186 + 0.519** | 10.24 + 1.293** |
| IL-13Ra2 | ND | ND | ND | ND |
| IL-10 | 0.055 + 0.004 | 0.084 + 0.007* | 0.124 + 0.031** | 0.110 + 0.002** |
| CD40 | 0.066 + 0.008 | 0.071 + 0.006 | 0.124 + 0.006** | 0.171 + 0.027** |
| CD40L | 0.151 + 0.027 | 0.107 + 0.006 | 0.267 + 0.090 | 0.215 + 0.054 |

[a]Data a presented as mean + standard deviation of five animals per group.
[b]**p<0.01 and *p<0.05 using one-way ANOVA with Dunnett's post test, comparing IL-31-treatment at lower concentrations (2, 0.2 and 0.02 ug/day) to treatment the standard 20 ug/day used in previous experiments.

3.2.3.1.2 BAL Fluid Differentials

Analysis of BAL cell infiltrates also suggested that there is a dose dependant effect on the quantity and type of cellular infiltrates following intranasal challenge with allergen. Doses of IL-31 at 20 and 2 ug/day are more effective at inducing significant decreases in eosinophil, macrophage and lymphocyte numbers in the lung cell infiltrates compared to the lower doses of IL-31 (0.2 and 0.02 ug/day).

No statistical significance was observed in OVA-specific or total IgE (data not shown)

Serum, BAL fluid cytokines and airway hyper-responsiveness was not measured in this experiment.

3.2.3.2 Experiment #2

In the previous experiment, we demonstrated that the effect of IL-31 on airway inflammation was dose-dependant. Analysis of gene expression and BAL cell infiltrates suggested that a 10-fold lower dose of IL-31 (2 ug/day) was able to significantly inhibit the level of cellular infiltrate in the lung following intranasal challenge with the allergen. This experiment was designed to determine whether 2 ug/day and lower doses of IL-31 could decrease airway hyper-responsiveness following allergen sensitization and challenge.

Alzet 14-day osmotic pumps were loading with increasing concentrations of IL-31, from 0.005 ug/day to 2 ug/day, and implanted in mice during OVA allergen sensitization and challenge. Analysis was performed as previously described on 5 mice per group.

3.2.3.2.1 Lung and BAL cell mRNA

Analysis of lung mRNA from IL-31-treated animals, to determine the lowest effective concentration of the IL-31 for down-regulation of genes in the lung, demonstrated that although some genes like IL-4, IL-13, IFNg, IL-31Ra and TNFa showed a trend towards down-regulation of expression at increasing concentrations of IL-31 (maximum dose of 2 ug/ml), the differences were not statistically significant in most genes (Table 14). CD40L was the only gene tested that showed significant down-regulation of expression when only 2 ug or 0.2 ug/day of IL-31 was delivered. The PCR data for all genes tested in lung tissues are summarized in (Table 13).

TABLE 13 mRNA Analysis of Lungs from IL-31-Treated Mice

| Gene | 2 ug/day | 0.2 ug/day | 0.02 ug/day | 0.01 ug/day | 0.05 ug/day | None |
|---|---|---|---|---|---|---|
| IL-4 | 0.035_0.015 | 0.040 + 0.019 | 0.046 + 0.016 | 0.056 + 0.023 | 0.036 + 0.004 | 0.054 + 0.037 |
| IL-5 | 0.241 + 0.053 | 0.244 + 0.033 | 0.241 + 0.040 | 0.324 + 0.072 | 0.272 + 0.083 | 0.243 + 0.095 |
| IL-9 | 0.013 + 0.008 | 0.0130.005 | 0.016 + 0.006 | 0.007 + 0.023 | 0.023 + 0.005 | 0.018 + 0.008 |
| IL-13 | 0.086 + 0.030 | 0.117 + 0.038 | 0.123 + 0.052 | 0.275 + 0.047** | 0.169 + 0.042 | 0.135 + 0.051 |
| IL-31Ra | 0.872 + 0.418 | 0.853 + 0.241 | 1.130 + 0.6464 | 1.191 + 0.471 | 1.240 + 0.221 | 1.304 + 0.899 |
| TNFa | 0.193 + 0.054** | 0.239 + 0.063 | 0.260 + 0.072 | 0.244 + 0.046 | 0.341 + 0.035 | 0.324 + 0.050 |
| MIP-2 | 4.818 + 1.761 | 2.282 + 0.948* | 3.382 + 1.881 | 1.775 + 0.631** | 2.503 + 0.483 | 5.074 + 1.838 |
| IL-8R | 3.657 + 1.899 | 2.679 + 0.661 | 3.444 + 0.631 | 2.091 + 0.524 | 2.364 + 0.783 | 3.932 + 1.818 |
| IFNg | 0.092 + 0.047 | 0.113 + 0.036 | 0.123 + 0.051 | 0.143 + 0.027 | 0.192 + 0.039 | 0.222 + 0.165 |
| CCL27 | 0.750 + 0.140** | 0.427 + 0.086 | 0.551 + 0.113 | 0.395 + 0.072 | 0.478 + 0.019 | 0.531 + 0.072 |
| Cathepsin L | 13.25 + 5.586 | 9.994 + 2.637 | 12.10 + 3.106 | 13.73 + 1.771 | 11.05 + 2.332 | 14.76 + 8.488 |
| Class II | 50.43 + 9.632 | 48.27 + 7.995 | 59.24 + 13.30 | 51.49 + 14.45 | 50.48_7.952 | 54.05 + 13.57 |
| IL-13Ra2 | ND | ND | ND | ND | ND | ND |
| Eotaxin | 3.926 + 0.572 | 3.218 + 0.594 | 3.427 + 0.693 | 4.201 + 0.696 | 3.377 + 0.456 | 3.364 + 0.744 |
| IL-10 | 0.068 + 0.031 | 0.063 + 0.032 | 0.064 + 0.023 | 0.091 + 0.023 | 0.072 + 0.021 | 0.072 + 0.046 |
| TSLP | 1.110 + 0.164 | 0.854 + 0.173* | 1.010 + 0.231 | 0.846 + 0.191* | 1.164 + 0.057 | 1.317 + 0.484 |
| CD40 | 2.339 + 0.423 | 1.859 + 0.213 | 2.352 + 0.747 | 2.438 + 0.539 | 2.424 + 0.318 | 2.813 + 1.340 |
| CD40L | 0.532 + 0.099** | 0.514 + 0.107** | 0.660 + 0.165 | 0.641 + 0.118 | 0.855 + 0.087 | 1.007 + 0.184 |

[a]Data a presented as mean + standard deviation of five animals per group. Statistical analysis was a one-way ANOVA with Dunnett's post test, comparing IL-31-treatment versus vehicle control (no IL-31, grey column) (**p < 0.01 and *p < 0.05).

Table 14 shows the gene analysis for cells in the BAL fluid. Trends for gene regulation in the cells of the BAL were less obvious (Table 14). Consistent with previous studies, MIP-2 and IL-8R were up-regulated at 2 ug/ml but not at lower concentrations of IL-31 (Table 14). Interestingly, there appeared to be an up-regulation of some genes at some of the concentrations of IL-31 below 2 ug/day, suggesting a possible bell curve for IL-31 activity. This was particularly obvious for IL-5 and IL-13 (Table 14). The corresponding protein levels in the BAL fluid demonstrate a consistent pattern between gene regulation and protein levels in the BAL. KC, which is related to MIP-2, was also found to be up-regulated at 2 ug/ml of IL-31.

TABLE 14 mRNA Levels in BAL Cell Homogenates from Dose curve IL-31-Treated Mice

| Gene | 2 | 0.2 | 0.02 | 0.01 | 0.05 | None |
|---|---|---|---|---|---|---|
| IL-4 | 0.011 + 0.001 | 0.011 + 0.002 | 0.011 + 0.003 | 0.013 + 0.002* | 0.010 + 0.004 | 0.006 + 0.001 |
| IL-5 | 0.019 + 0.005* | 0.035 + 0.008* | 0.038 + 0.002* | 0.038 + 0.002* | 0.045 + 0.013** | 0.016 + 0.006 |
| IL-9 | ND | ND | ND | ND | ND | ND |
| IL-13 | 0.023 + 0.001 | 0.050 + 0.005** | 0.029 + 0.007 | 0.055 + 0.012** | 0.049 + 0.005** | 0.021 + 0.001 |
| IL-31Ra | 1.205 + 0.110 | 1.098 + 0.215 | 1.168 + 0.110 | 1.225 + 0.117 | 1.680 + 0.203** | 1.158 + 0.122 |
| TNFa | 0.758 + 0.159** | 0.338 + 0.050 | 0.361 + 0.077 | 0.357 + 0.050 | 0.260 + 0.110 | 0.267 + 0.037 |
| MIP-2 | 4.901 + 0.538** | 1.934 + 0.149* | 2.372 + 0.100** | 1.805 + 0.366 | 0.705 + 0.128 | 1.185 + 0.127 |
| IL-8R | 2.355 + 0.191** | 0.525 + 0.055 | 0.664 + 0.089 | 0.582 + 0.075 | 0.427 + 0.076 | 0.431 + 0.051 |
| IFNg | 0.093 + 0.014 | 0.141 + 0.033* | 0.089 + 0.031 | 0.174 + 0.029** | 0.129 + 0.017 | 0.073 + 0.006 |
| CCL27 | 0.036 + 0.009 | 0.046 + 0.011 | 0.034 + 0.017 | 0.050 + 0.021 | 0.036 + 0.002 | 0.031 + 0.004 |
| Cathepsin L | 52.81 + 7.474 | 33.19 + 4.310 | 38.888 + 2.105 | 41.04 + 3.475 | 52.63 + 15.13 | 38.57 + 11.56 |
| Class II | 9.518 + 1.338 | 19.62 + 3.453 | 12.92 + 0.597 | 19.26 + 1.987 | 13.84 + 12.15 | 17.61 + 14.401 |
| IL-13Ra2 | ND | ND | ND | ND | ND | ND |
| Eotaxin | 0.086 + 0.013 | 0.074 + 0.014 | 0.076 + 0.006 | 0.271 + 0.019** | 0.158 + 0.027** | 0.077 + 0.007 |
| IL-10 | 0.065 + 0.007 | 0.095 + 0.012* | 0.060 + 0.003 | 0.100 + 0.015** | 0.062 + 0.011 | 0.057 + 0.020 |
| TSLP | 0.023 + 0.011 | 0.026 + 0.011 | 0.029 + 0.004 | 0.095 + 0.025** | 0.038 + 0.018 | 0.025 + 0.016 |
| CD40 | 0.156 + 0.011** | 0.112 + 0.005* | 0.104 + 0.012 | 0.122 + 0.006** | 0.151 + 0.018** | 0.085 + 0.006 |
| CD40L | 0.183 + 0.033 | 0.304 + 0.060 | 0.284 + 0.021 | 0.330 + 0.068 | 0.229 + 0.039 | 0.249 + 0.040 |

[a]L-31 Delivery (ug/day)

[a]Data are presented of mean + standard deviation of triplicate wells of pooled BAL cells collected from five animals per group. Statistical analysis was performed using one-way ANOVA with Dunnett's post test, comparing IL-31-treatment to vehicle control treated animals (no IL-31, grey column) (**p < 0.01 and *p < 0.05).

3.2.3.2.2 BAL Fluid Cytokines

BAL fluid was analyzed for cytokines by a luminex multiplex assay. IL-4, IL-5. IL-9, IL-13 and KC were all detected in the BAL fluid. The levels of cytokines in the BAL fluid appeared to reflect the data collected for expression of the genes in the BAL, with the lower concentrations of IL-31 inducing significantly higher levels of IL-5 and IL-13 protein. IL-4 also appeared to be up-regulated at the lower concentrations but the difference between IL-31 treatment and no treatment did not reach statistical significance. KC was found to be up-regulated at 2 ug/day compared to no treatment. No TNFa, IFNg and MCP-1 was detected in the BAL fluid. MIP-2 was not tested.

3.2.3.2.3 BAL Fluid Differentials

Analysis of BAL differentials shows that there was a trend towards a decrease in eosinophil infiltrates in the BAL of mice treated with the maximum concentration of IL-31 in this study (2 ug/day) compared to those mice that were treated with the lower doses. Due to the large degree of variation, the data was not statistically significant. There was a significant decrease in macrophage numbers with 2 ug/day of IL-31. None of the other IL-31 concentrations seemed to be effective at decreasing macrophage numbers.

3.2.3.2.4 Serum IgE

Past experiments have indicated that the decreases in inflammatory parameters associated with IL-31 treatment at higher concentrations (20 ug/day) generally do not result in decreases in either total IgE or OVA-specific IgE (refer to section 1 of this report). Nevertheless, serum was analyzed for total and OVA-specific IgE following treatment with different concentrations of IL-31. In this experiment, although there were no differences in the levels of total IgE in the sera of these mice, there did appear to be an increase in OVA-specific IgE in the groups that were treated with 0.02 and 0.01 ug per day of IL-31 compared to either no IL-31 treatment or the lowest dose of IL-31 (0.005 ug/day). It is interesting to note here that 0.1 ug/day of IL-31 induced significant up-regulation of IL-5 and IL-13 mRNA and protein in BAL fluid (Table 15). This data might suggest that although high concentrations of IL-31 decrease pulmonary inflammation to airway allergens, low concentrations of IL-31 may have the opposite effect.

3.2.3.2.5 Whole Body Plethysmography

Mice were further analyzed by whole body plethysmography for airway hyper-responsiveness following intranasal challenge with OVA. IL-31 treatment at the concentrations tested in this experiment did not decrease airway hyper-responsiveness.

3.2.3.3 Experiment #3

Our data have so far indicated that the anti-inflammatory effect of IL-31 in a murine model of airway hyper-responsiveness requires delivery of at least 20 ug/day of IL-31. A 10-fold decrease in IL-31 concentration does not consistently reduce airway inflammation and does not result in reduce airway hyper-responsiveness to allergen challenge. Immunohistochemistry of the mouse lung indicates that the majority of IL-31RA is expressed on both resident and infiltrating macrophage in the lung and it is unknown at this point if IL-31 is acting directly on these cells to produce the anti-inflammatory effect or if there is another target cell type. In order to determine if IL-31 acts on a resident cell type to down-regulate that inflammation associated with antigen-challenge and sensitization we wished to determine whether IL-31 pre-treatment (IL-31 delivery prior to sensitization and challenge) would have the same effect as IL-31 delivery throughout both the sensitization and challenge phases of the model.

Mouse IL-31 was delivered at a dose of 20 g per day (approximately 1 mg/kg per day) by an osmotic mini-pump (Alzet) implanted subcutaneously into the dorsum of BALB/c mice. Mice were either implanted with 7-day pumps 7 days prior to the first OVA sensitization (IL-31 pre-treatment) or with 14-day pumps three days post-sensitization (IL-31 treatment) to compare treatment prior to sensitization and treatment during sensitization and challenge. As in all experiments so far, PBS+0.1% BSA was included as the vehicle control. Murine IL-31 derived from *E. coli*, was used to prepare IL-31 pumps.

3.2.3.3.1 Lung and BAL mRNA

Analysis of gene expression in total lung homogenates from vehicle-treated, IL-31 pre-treated and IL-31 treated mice are summarized in Table 15. Statistical analysis was performed by comparing the IL-31 groups (pre-treatment or treatment) to the vehicle control group.

The data clearly show that down-regulation of genes associated with inflammation mostly only occurs when IL-31 treatment is present throughout sensitization and challenge. Genes requiring the presence of IL-31 during the entire period of sensitization and challenge include IL-4, IL-5 and IL-31RA. A number of additional genes were down-regulated regardless of whether IL-31 was given as a pre-treatment or during sensitization and challenge. These genes include IL-9, TNFa, IFNg, Cathepsin L, IL-10, CD40 and CD40L.

Interestingly, IL-13 was found to be significantly increased compared to vehicle treated controls when IL-31 was given as a pre-treatment (Table 15). Of all the genes tested, IL-13 was the only gene that showed this pattern of expression. IL-13 has been shown to be involved in the manifestation of disease in this model.

TABLE 15

Levels in Total Lung Homogenates from Vehicle- and IL-31-Treated Mice

| Gene | IL-31 Pre-Treatment | IL-31 Treatment | Vehicle Control |
|---|---|---|---|
| IL-4 | 0.041 + 0.009 | 0.0270.009* | 0.048 + 0.012 |
| IL-5 | 0.357 + 0.074 | 0.242 + 0.172** | 0.557 + 0.156 |
| IL-9 | 0.009 + 0.007** | 0.003 + 0.002** | 0.112 + 0.075 |
| IL-13 | 0.207 + 0.055* | 0.082 + 0.038 | 0.100 + 0.052 |
| IL-31Ra | 1.452 + 0.433 | 0.612 + 0.243** | 2.034 + 0.6116 |
| TNFa | 0.219 + 0.049* | 0.229 + 0.083* | 0.439 + 0.174 |
| MIP-2 | 1.199 + 0.586 | 2.748 + 0.795 | 1.990 + 0.679 |
| IL-8R | 2.334 + 0.828 | 4.306 + 1.951 | 2.533 + 0.700 |
| IFNg | 0.158 + 0.055** | 0.125 + 0.058** | 0.586 + 0.263 |
| CCL27 | 0.474 + 0.56** | 0.687 + 0.061 | 0.823 + 0.170 |
| Cathepsin L | 14.82 + 3.574** | 13.537 + 5.252** | 29.53 + 10.56 |
| Class II | 54.04 + 9.134 | 45.30 + 12.71 | 46.16 + 6.801 |
| IL-13Ra2 | ND | ND | ND |
| Eotaxin | 5.060 + 1.166 | 4.205 + 2.007 | 3.648 + 0.654 |
| IL-10 | 0.106 + 0.018* | 0.067 + 0.027** | 0.196 + 0.079 |
| CD40 | 2.121 + 0.293** | 1.906 + 0.319** | 3.531 + 0.692 |
| CD40L | 0.773 + 0.190* | 0.721 + 0.208* | 1.245 + 0.421 |

<sup>a</sup>Data a presented as mean + standard deviation of five animals per group.
**p < 0.01 and *p < 0.05 using one-way ANOVA with Dunnett's post test, comparing IL-31 pre-treatment or IL-31-treatment with vehicle control (no IL-31).

Previous studies of gene regulation in mRNA from BAL cells has shown that IL-31 treatment can prevent the up-regulation of mRNA encoding asthma related genes such as IL-5 and IL-13. In this experiment, similar results were observed for IL-31 treated animals compared to vehicle treated controls (Table 16).

Once again, IL-31 treatment, when given during sensitization and challenge, significantly down-regulated IL-5, IL-13, IL-31Ra, IFNg, Cathepsin L, Class II, CD40 and CD40L gene expression in cells collected from the BAL. In striking contrast however, IL-31 pre-treatment appears to significantly increase the expression of many of these genes when compared to vehicle control animals including IL-5, IL-13, IFNg, Class II, CD40 and CD40L.

These data suggest that IL-31 pre-treatment may have an adverse effect on pulmonary inflammation compared to vehicle control mice and may indeed exacerbate the disease. We have seen in the previous experiments that IL-31 treatment down-regulates the expression of IL-31RA in both lung and BAL cellular infiltrates. IL-31 pre-treatment may down-regulate the receptor prior to sensitization so that Th2 responses are exacerbated.

Of note, IL-31 treatment up-regulated IL-8R and MIP-2 as has been previously observed, whereas IL-31 pre-treatment had no effect.

TABLE 16

Levels in BAL mRNA Homogenates from BSA- and IL-31-Treated Mice

| Gene | IL-31 Pre-Treatment | IL-31 Treatment | Vehicle Control |
|---|---|---|---|
| IL-4 | 0.019 + 0.004 | 0.009 + 0.002 | 0.013 + 0.004 |
| IL-5 | 0.127 + 0.021** | 0.027 + 0.008* | 0.069 + 0.019 |
| IL-9 | ND | ND | ND |
| IL-13 | 0.139 + 0.018** | 0.024 + 0.004* | 0.051 + 0.009 |
| IL-31Ra | 2.569 + 0.328 | 0.971 + 0.139** | 2.459 + 0.131 |
| TNFA | 0.260 + 0.021 | 0.433 + 0.041 | 0.274 + 0.014 |
| MIP-2 | 1.563 + 0.059 | 4.110 + 0.231** | 0.994 + 0.081 |
| IL-8R | 0.671 + 0.026 | 1.442 + 0.143** | 0.605 + 0.100 |
| IFNg | 0.336 + 0.022** | 0.118 + 0.015** | 0.245 + 0.016 |
| CCL27 | 0.059 + 0.009 | 0.045 + 0.013 | 0.062 + 0.021 |
| Cathepsin L | 60.79 + 4.704 | 43.76 + 4.628** | 83.75 + 20.88 |
| Class II | 54.09 + 5.045** | 10.173 + 0.608** | 37.65 + 1.466 |
| IL-13Ra2 | ND | ND | ND |
| Eotaxin | ND | ND | ND |
| IL-10 | 0.298 + 0.071 | 0.071 + 0.010** | 0.221 + 0.029 |
| CD40 | 0.202 + 0.023** | 0.053 + 0.001** | 0.137 + 0.013 |
| CD40L | 0.793 + 0.021** | 0.253 + 0.009** | 0.590 + 0.080 |

[a]Data are presented of mean + standard deviation of triplicate wells of pooled BAL cells collected from five animals per group.
**$p < 0.01$ and *$p < 0.05$ using one-way ANOVA with Dunnett's post test, comparing IL-31 pre-treatment or IL-31-treatment to vehicle control treated animals (no IL-31)

3.2.3.3.2 BAL Fluid Cytokines

The animals receiving IL-31 treatment showed a trend towards decreases in IL-4, IL-5 and IL-13 in the BAL fluid compared to the vehicle treated group, though the results were not statistically significant. Consistent with previous studies with IL-31-treated mice, this group also had significantly elevated KC levels. All other cytokines that were assayed were below the limit of detection.

In contrast to the IL-31 treated animals, cytokine analysis of BAL fluid from mice that were pre-treated with IL-31 showed significant increases in the levels of IL-5, IL-9, and IL-13 compared to vehicle treated mice. This data is consistent with the up-regulation of genes like IL-5 and IL-13 in mRNA from BAL cells following pre-treatment with IL-31 and suggest that IL-31 pre-treatment may exacerbate pulmonary inflammation.

3.2.3.3.3 BAL Fluid Differentials

Analysis of cell differentials showed a trend towards lower eosinophil infiltrates in the BAL of mice treated with IL-31 during OVA sensitization and challenge, which is consistent with previous studies. Pre-treatment of mice with IL-31 prior to sensitization and challenge did not appear to alter the type or number of cellular infiltrates significantly from vehicle-treated control animals.

3.2.3.3.4 Serum IgE

There was no significant difference between groups in either total IgE, or OVA-specific IgE levels.

3.2.3.3.5 Whole Body Plethysmography

Groups of mice that were pre-treated with IL-31, treated with IL-31 during sensitization and challenge, or treated with vehicle were analyzed for their sensitivity to airway hyper-responsiveness following intranasal allergen challenge. Results indicate that IL-31 pre-treatment does not affect airway hyper-responsiveness compared to a no IL-31 treatment control. In contrast however, IL-31 treatment throughout sensitization and challenge decreased airway hyper-responsiveness to levels comparable to those animals that had not received an allergen challenge.

This current study indicates that IL-31 pre-treatment is unsuccessful at decreasing airway hyper-responsiveness and although pre-treatment may increase IL-5, IL-13 and IL-9 levels in the BAL fluid, this does not appear to exacerbate airway hyper-responsiveness compared to no IL-31 treatment.

3.2.3.4 Summary

We have previously established that 20 ug/day of IL-31 delivered during OVA sensitization and challenge results in down-regulation of pulmonary inflammation. In this section we demonstrate that this effect is dose-dependent. Although concentrations of IL-31 as low as 2 ug/day can still reduce expression of genes that are important in the development of airway hyper-responsiveness, this low concentration was not sufficient to result in reduced airway hyper-responsiveness as measured by whole body plethysmography.

In addition, although the receptor for IL-31 appears to be expressed on both resident and infiltrating macrophages in the lung, pre-treatment with IL-31 immediately prior to allergen sensitization is not sufficient to achieve the anti-inflammatory effects of IL-31 we have so far observed. Moreover, it is possible that IL-31 pre-treatment may increase production of Th-2-type cytokines such as IL-5, IL-13 and IL-9. This finding may be in support of a recent finding suggesting that IL-31RA regulates Th-2-type inflammatory responses and that in the absence of IL-31RA receptor Th-2-type responses may be exacerbated (3). We know that delivery of IL-31 can down-regulate IL-31RA and we postulate that pre-treatment with IL-31 results in the effective absence of IL-31RA prior to antigen sensitization resulting in increased expression of IL-5, IL-13 and IL-9. In this particular experiment however, those increases in Th-2-type cytokines did not result in exacerbated airway hyper-responsiveness.

3.2.4 Airway Hyper-Responsiveness in IL-31 Transgenics
3.2.4.1 Experiment #1

IL-31 transgenic animals were sensitized and challenged with OVA as previously described and tested for airway hyper-responsiveness by whole body plethysmography. The data suggest that IL-31 transgenic animals were significantly less sensitive to OVA-induced airway hyper-responsiveness compared to wildtype control littermates.

3.2.4.2 Experiment #2

This experiment was to repeat the test of the sensitivity of IL-31 transgenic mice to allergen induced airway hyper-responsiveness. Analysis of the data show similar findings to the previous experiment. IL-31 transgenic animals appear less susceptible to pulmonary inflammation induced by a sensitizing allergen, especially at the highest dose of methacholine.

3.2.4.3 Experiment #3

Having established that IL-31 transgenic animals appear less sensitive to airway hyper-responsiveness as measured by whole body plethysmography, we analyzed the nature of the decreased inflammation in the lungs. Therefore, IL-31 transgenic animals and wildtype controls were sensitized with OVA and challenged via the airways with either OVA or PBS. Forty-eight hours following intranasal challenge, BAL fluid was collected for assessment of lung cellular infiltrates and lung was collected for mRNA and gene expression analysis.

Serum was also collected for analysis of total and OVA-specific IgE. In this experiment, cytokines in the BAL fluid and serum were not measured.

3.2.4.3.1 Lung and BAL mRNA

Lung mRNA was tested by quantitative RT-PCR for expression of a panel of genes that have been implicated in pulmonary inflammation. Two sets of comparisons were made between the four groups of animals. Table 17 shows data from the first analysis where IL-31 transgenic animals were directly compared to wildtype mice under conditions of either OVA or PBS sensitization. In general, there were no differences between IL-31 transgenic and control littermates when challenged with either OVA or PBS. For a number of genes there appeared to be lower expression in the lungs of IL-31 transgenics following OVA sensitization including IL-4, IL-5, IL-13 and IL-31RA, however these were not statistically significant (Table 17). One gene, IL-10, showed significantly higher expression in the lung of wildtype mice following OVA challenge, compared to IL-31 transgenic mice.

TABLE 17 mRNA Levels in Total Lung Homogenates from IL-31 Transgenic mice following Sensitization and Challenge with OVA - Comparison of Wildtype versus IL-31 Transgenic

| Gene | [a]OVA Challenge | | [a]PBS | |
| --- | --- | --- | --- | --- |
|  | IL-31 Tg | Wildtype | IL-31 Tg | Wildtype |
| IL-4 | 0.020 | 0.041 | 0.001 | 0.001 |
| IL-5 | 0.188 | 0.300 | 0.105 | 0.093 |
| IL-13 | 0.365 | 0.645 | 0.001 | 0.001 |
| IL-31Ra | 0.601 | 1.023 | 0.179 | 0.192 |
| IFNg | 0.318 | 0.324 | 0.110 | 0.136 |
| TNFa | 0.973 | 0.654 | 0.797 | 0.693 |
| MIP-2 | 0.946 | 1.878 | 1.302 | 0.539 |
| IL-8R | 3.666 | 4.136 | 4.205 | 3.696 |
| CCL27 | 0.511 | 0.528 | 0.806 | 0.814 |
| Cathepsin L | 34.840 | 43.339 | 45.421 | 55.763 |
| Class II | 49.180 | 50.207 | 24.050 | 33.128 |
| IL-13Ra2 | ND | ND | ND | ND |
| Eotaxin-1 | 2.267 | 2.729 | 0.267 | 0.182 |
| IL-10 | 0.033** | 0.049 | 0.009 | 0.008 |
| CD40 | 2.559 | 3.243 | 2.215 | 2.714 |
| CD40L | 0.747 | 0.873 | 0.382 | 0.494 |

[a]Statistical analysis for differences between groups was performed with one-way ANOVA with Tukey's post-comparison test of all groups (**p < 0.01)

When animals were compared based on OVA versus PBS challenge, the data suggest that wildtype mice are more likely to significantly increase gene levels following OVA challenge compared to IL-31 transgenic animals. Data show that the up-regulation of genes such as IL-4, IL-5, IL-13 and IL-31Ra were more significantly up-regulated in wildtypes OVA sensitized animals compared to PBS sensitized mice than transgenic OVA sensitized compared to transgenic PBS mice. Some genes like Eotaxin and Class II were equally well up-regulated in either the wildtype or IL-31 transgenic OVA sensitized animals compared to their PBS controls (Table 18).

TABLE 18 mRNA Levels in Total Lung Homogenates from IL-31 Transgenic mice following Sensitization and Challenge with OVA - Comparison of OVA versus PBS

| Gene | [a]IL-31 Tg | | [a]Wildtype | |
| --- | --- | --- | --- | --- |
|  | OVA | PBS | OVA | PBS |
| IL-4 | 0.020 | 0.001 | 0.041* | 0.001 |
| IL-5 | 0.188 | 0.105 | 0.300* | 0.093 |
| IL-13 | 0.365 | 0.001 | 0.645** | 0.001 |
| IL-31Ra | 0.601 | 0.179 | 1.023* | 0.192 |
| IFNg | 0.318 | 0.110 | 0.324 | 0.136 |
| TNFa | 0.973 | 0.797 | 0.654 | 0.693 |
| MIP-2 | 0.946 | 1.302 | 1.878 | 0.539 |
| IL-8R | 3.666 | 4.205 | 4.136 | 3.696 |
| CCL27 | 0.511*** | 0.806 | 0.528*** | 0.814 |
| Cathepsin L | 34.840* | 45.421 | 43.339** | 55.763 |
| Class II | 49.180*** | 24.050 | 50.207** | 33.128 |
| IL-13Ra2 | ND | ND | ND | ND |
| Eotaxin-1 | 2.267** | 0.267 | 2.729** | 0.182 |
| IL-10 | 0.033 | 0.009 | 0.049** | 0.008 |
| CD40 | 2.559 | 2.215 | 3.243 | 2.714 |
| CD40L | 0.747 | 0.382 | 0.873 | 0.494 |

[a]Statistical analysis for differences between groups was performed with one-way ANOVA with Tukey's post-comparison test of all groups (*P < 0.001, p < 0.01, *p < 0.05)

Analysis of mRNA from BAL cell infiltrates comparing IL-31 transgenic to wildtype controls under conditions of either OVA or PBS intranasal challenge suggests (i) three genes tested, TNFa, IL-8R and Class II, were expressed at significantly different levels in IL-31 transgenics compared to wildtypes in the absence of a antigen-specific challenge. TNFa and Class II were both lower in transgenics versus wildtypes where as IL-8R was expressed at higher levels. (ii) Following OVA intranasal challenge wildtype control mice up-regulated the expression of IL-4, IL-13, IL-8R, Class II, Cathepsin L, Eotaxin, IL-10 and CD40 significantly more than the IL-31 transgenic mice. (iii) IL-31 transgenic mice up-regulated CD40L following OVA challenge significantly more than wildtype littermate controls (Table 19).

TABLE 19 mRNA Levels in BAL mRNA from IL-31 Transgenic and Wildtype mice following Sensitization and Challenge with OVA - Comparison of Wildtype versus IL-31 Transgenic

| Gene | [a]OVA | | [a]PBS challenge | |
| --- | --- | --- | --- | --- |
|  | IL-31 Tg | Wildtype | IL-31 Tg | Wildtype |
| IL-4 | 0.011*** | 0.030 | ND | ND |
| IL-5 | 0.071 | 0.102 | 0.000 | 0.001 |
| IL-13 | 0.028*** | 0.044 | ND | ND |
| IL-31Ra | 0.480 | 0.520 | 0.010 | 0.017 |
| IFNg | 0.395 | 0.346 | 0.025 | 0.026 |
| TNFa | 0.522 | 0.451 | 1.924*** | 3.316 |
| MIP-2 | 0.991 | 1.031 | 4.960 | 5.278 |
| IL-8R | 0.736*** | 1.541 | 0.767*** | 0.350 |
| CCL27 | 0.176 | 0.168 | 0.165 | 0.200 |
| Cathepsin L | 42.517* | 55.496 | 16.574 | 24.384 |
| Class II | 23.420*** | 29.767 | 4.733** | 9.228 |
| IL-13Ra2 | ND | ND | ND | ND |
| Eotaxin-1 | 0.001*** | 0.005 | ND | ND |
| IL-10 | 0.050* | 0.066 | 0.008 | 0.003 |
| CD40 | 0.229** | 0.265 | 0.033 | 0.038 |
| CD40L | 0.707** | 0.538 | 0.052 | 0.075 |

[a]Statistical analysis for differences between groups was performed with one-way ANOVA with Tukey's post-comparison test of all groups (*p < 0.001, p < 0.01 and *p < 0.05)

Data in Table 20 clearly show that OVA intranasal challenge induces a number of genes in both IL-31 transgenic and wildtype OVA treated mice compared to PBS challenge groups. However, two genes, IL-8R and Eotaxin were not up-regulated in IL-31 transgenic OVA challenged mice compared to their PBS controls, whereas both genes were up-regulated in the wildtype mice challenged with OVA, compared to PBS controls (Table 20).

TABLE 20 mRNA Levels in BAL mRNA from IL-31 Transgenic mice following Sensitization and Challenge with OVA - Comparison of OVA versus PBS

| Gene | aIL-31 Transgenic | | aWildtype | |
|---|---|---|---|---|
|  | OVA | PBS | OVA | PBS |
| IL-4 | 0.011*** | ND | 0.030*** | ND |
| IL-5 | 0.071*** | 0.000 | 0.102*** | 0.001 |
| IL-13 | 0.028*** | ND | 0.044*** | ND |
| IL-31Ra | 0.480*** | 0.010 | 0.520*** | 0.017 |
| IFNg | 0.395*** | 0.025 | 0.346*** | 0.026 |
| TNFa | 0.522*** | 1.924 | 0.451*** | 3.316 |
| MIP-2 | 0.991*** | 4.960 | 1.031*** | 5.278 |
| IL-8R | 0.736 | 0.767 | 1.541*** | 0.350 |
| CCL27 | 0.176 | 0.165 | 0.168 | 0.200 |
| Cathepsin L | 42.517*** | 16.574 | 55.496*** | 24.384 |
| Class II | 23.420*** | 4.733 | 29.767*** | 9.228 |
| IL-13Ra2 | ND | ND | ND | ND |
| Eotaxin-1 | 0.001 | ND | 0.005*** | ND |
| IL-10 | 0.050*** | 0.008 | 0.066*** | 0.003 |
| CD40 | 0.229*** | 0.033 | 0.265*** | 0.038 |
| CD40L | 0.707* | 0.052 | 0.538* | 0.075 | aStatistical analysis for differences between groups was performed with one-way ANOVA with Tukey's post-comparison test of all groups (*$p < 0.001$, $p < 0.01$ and *$p < 0.05$)

3.2.4.3.2 BAL Cell Differentials

BAL cell infiltrates were collected and analyzed for cellular content. Although there was a trend towards decreased eosinophil numbers in the lung cell infiltrates of IL-31 Tg animals compared to wildtype control littermates, the data did not reach statistical significance due to variability within the test groups.

3.2.4.3.3 Serum OVA-Specific and Total IgE

Analysis of total IgE in the serum of IL-31 transgenic animals following OVA-sensitization showed significant decreases in the production of total IgE in the circulation of IL-31 transgenic animals compared to littermate wildtype controls ($p=0.048$, unpaired t test), however there were no statistical differences in the level of OVA-specific IgE detectible in the serum.

3.2.4.4 Summary

Given that IL-31 delivery decreases pulmonary inflammation following allergen sensitization and challenge, we hypothesized that IL-31 transgenic animals would also be less susceptible to allergen induced asthma. Indeed IL-31 transgenics appeared to develop less airway hyper-responsiveness to OVA sensitization and challenge when airway responsiveness was measured by whole body plethysmography. We found that IL-31 transgenics appeared to be more resistant to the up-regulation of Th-2-type genes following OVA sensitization and challenge compared to littermate controls. Moreover, there was a trend towards decreased numbers of eosinophils in the lungs OVA-challenged IL-31 transgenics versus wildtype controls. These data are consistent with our observations that IL-31 over-expression down-regulates pulmonary inflammation.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for determining the optimum dose of an IL-31 agonist to treat asthma, airway hyper-responsiveness or allergic rhinitis comprising:
   a) taking a first sample of lung tissue or BAL fluid from a patient with asthma, airway hyper-responsiveness or allergic rhinitis;
   b) measuring the level of proinflammatory cytokines expressed in the first sample;
   c) administering an amount of the IL-31 agonist to the patient, wherein the IL-31 agonist is a polypeptide comprising amino acid residues 27-164 of SEQ ID NO:2;
   d) taking a second sample of lung tissue or BAL fluid from the patient;
   e) measuring the level of proinflammatory cytokines expressed in the second sample;
   f) comparing the level of proinflammatory cytokines expressed in the first sample to the level of proinflammatory cytokines expressed in the second sample; and
   g) determining the level of the IL-31 agonist that is sufficient to reduce the level of proinflammatory cytokines in the second sample.

2. The method of claim 1, wherein the proinflammatory cytokines are IL-5 or IL-13.

3. The method of claim 1, wherein the proinflammatory cytokines are IL-5 and IL-13.

4. The method of claim 1, wherein the IL-31 agonist is administered in a pharmaceutical composition.

5. A method for determining if a dose of an IL-31 agonist is sufficient to treat asthma, airway hyper-responsiveness or allergic rhinitis comprising:
   a) taking a first sample of lung tissue or BAL fluid from a patient with asthma, airway hyper-responsiveness or allergic rhinitis;
   b) measuring the level of proinflammatory cytokines expressed in the first sample;
   c) administering an amount of the IL-31 agonist to the patient, wherein the IL-31 agonist is a polypeptide comprising amino acid residues 27-164 of SEQ ID NO:2;
   d) taking a second sample of lung tissue or BAL fluid from the patient;
   e) measuring the level of proinflammatory cytokines expressed in the second sample;
   f) comparing the level of proinflammatory cytokines expressed in the first sample to the level of proinflammatory cytokines expressed in the second sample such that the level of proinflammatory cytokines in the second sample are reduced compared to the level of proinflammatory cytokines in the first sample; and
   g) determining if the level of the IL-31 agonist that is sufficient to reduce the level of proinflammatory cytokines in the second sample.

6. The method of claim 5, wherein the proinflammatory cytokines are IL-5 or IL-13.

7. The method of claim 5, wherein the proinflammatory cytokines are IL-5 and IL-13.

8. The method of claim 5, wherein the IL-31 agonist is administered in a pharmaceutical composition.

9. A method for determining the optimum dose of an IL-31 agonist to treat asthma, airway hyper-responsiveness or allergic rhinitis comprising:
   a) taking a sample of lung tissue or BAL fluid from a patient with asthma, airway hyper-responsiveness or allergic rhinitis;
   b) measuring the level of proinflammatory cytokines expressed in the sample;
   c) administering an amount of the IL-31 agonist to the patient, wherein the IL-31 agonist is a polypeptide comprising amino acid residues 27-164 of SEQ ID NO:2;
   d) comparing the level of proinflammatory cytokines expressed in the sample to the level of proinflammatory cytokines expressed a standard control or reference number; and
   e) comparing the level of proinflammatory cytokines expressed in the first sample to the level of proinflammatory cytokines expressed in a standard control or reference number such that the level of proinflammatory cytokines in the sample are reduced compared to the level of proinflammatory cytokines in the control; and f) determining the level of the IL-31 agonist that is sufficient to reduce the level of proinflammatory cytokines in the second sample.

10. The method of claim 9, wherein the proinflammatory cytokines are IL-5 or IL-13.

11. The method of claim 9, wherein the proinflammatory cytokines are IL-5 and IL-13.

12. The method of claim 9, wherein the IL-31 agonist is administered in a pharmaceutical composition.

* * * * *